United States Patent
Zumsteg et al.

(10) Patent No.: US 12,024,556 B2
(45) Date of Patent: Jul. 2, 2024

(54) **ANTI-*STAPHYLOCOCCUS* ANTIBODIES AND USES THEREOF**

(71) Applicant: Regeneron Pharmaceuticals, Inc., Tarrytown, NY (US)

(72) Inventors: Anna Zumsteg, Elmsford, NY (US); Christos Kyratsous, Irvington, NY (US); Brinda Prasad, Princeton, NJ (US); Alida Coppi, Flushing, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 79 days.

(21) Appl. No.: 16/689,593

(22) Filed: Nov. 20, 2019

(65) Prior Publication Data

US 2020/0157193 A1    May 21, 2020

Related U.S. Application Data

(60) Provisional application No. 62/865,436, filed on Jun. 24, 2019, provisional application No. 62/822,029, filed on Mar. 21, 2019, provisional application No. 62/770,608, filed on Nov. 21, 2018.

(51) Int. Cl.
| | |
|---|---|
| *C07K 16/12* | (2006.01) |
| *A61K 39/00* | (2006.01) |
| *A61K 39/40* | (2006.01) |
| *A61K 45/06* | (2006.01) |
| *A61P 31/04* | (2006.01) |

(52) U.S. Cl.
CPC .......... *C07K 16/1271* (2013.01); *A61K 39/40* (2013.01); *A61K 45/06* (2013.01); *A61P 31/04* (2018.01); *A61K 2039/505* (2013.01); *A61K 2039/572* (2013.01); *C07K 2317/20* (2013.01); *C07K 2317/21* (2013.01); *C07K 2317/33* (2013.01); *C07K 2317/52* (2013.01); *C07K 2317/565* (2013.01); *C07K 2317/732* (2013.01); *C07K 2317/92* (2013.01); *C07K 2317/94* (2013.01)

(58) Field of Classification Search
CPC ............ C07K 16/1271; C07K 2317/20; C07K 2317/21; C07K 2317/33; C07K 2317/52; C07K 2317/565; C07K 2317/732; C07K 2317/94; A61P 31/04; A61K 39/40; A61K 45/06; A61K 2039/505; A61K 2039/572
See application file for complete search history.

(56) References Cited

U.S. PATENT DOCUMENTS

| | | | |
|---|---|---|---|
| 6,596,541 B2 | 7/2003 | Murphy et al. | |
| 7,488,807 B2 * | 2/2009 | Mach ...................... | A61P 31/04 530/388.4 |
| 8,246,995 B2 | 8/2012 | Dai et al. | |
| 8,257,740 B1 | 9/2012 | Sung et al. | |
| 8,697,396 B2 | 4/2014 | Dall'Acqua et al. | |
| 9,416,171 B2 | 8/2016 | Lydon | |
| 10,143,186 B2 | 12/2018 | Mcwhirter et al. | |
| 2004/0101920 A1 | 5/2004 | Radziejewski et al. | |
| 2006/0024298 A1 | 2/2006 | Azar et al. | |
| 2007/0280945 A1 | 12/2007 | Stevens et al. | |
| 2010/0331527 A1 | 12/2010 | Davis et al. | |
| 2014/0134162 A1 | 5/2014 | Stavenhagen et al. | |
| 2014/0171623 A1 | 6/2014 | Dall'Acqua et al. | |
| 2014/0243504 A1 | 8/2014 | Davis et al. | |
| 2016/0024147 A1 | 1/2016 | Tustian et al. | |

FOREIGN PATENT DOCUMENTS

| | | | | |
|---|---|---|---|---|
| WO | WO-03063772 A2 * | 8/2003 | ............. | A61K 39/40 |
| WO | 2010/151792 A1 | 12/2010 | | |
| WO | 2012/122533 A2 | 9/2012 | | |
| WO | 2014/043361 | 3/2014 | | |
| WO | 2016/197071 | 12/2016 | | |
| WO | 2017/134440 A2 | 8/2017 | | |
| WO | 2018/128973 A1 | 7/2018 | | |
| WO | 2018/226861 | 12/2018 | | |
| WO | 2019/067682 A1 | 4/2019 | | |

OTHER PUBLICATIONS

Sela-Culang et al. (Frontiers in Immunology vol. 4, article 302, pp. 1-13), 2013.*
Skolnick et al. (Trends in Biotechnology 18: 34-39, 2000).*
Greenspan et al. (Nature Biotechnology 7: 936-937, 1999).*
Giusti et al. (Proc. Natl. Acad. Sci. USA. May 1987; 84 (9): 2926-2930).*
Winkler et al (J. Imm., 265:4505-4514, 2000).*
Chien et al. (Proc. Natl. Acad. Sci. USA. Jul. 1989; 86 (14): 5532-5536).*
Caldas et al. (Mol. Immunol. May 2003; 39 (15): 941-952).*
Casadevall et al. (PNAS, vol. 109 No. 31, pp. 12272-12273), 2012.*
Tkaczyk et al. (2012) "Identification of Anti-Alpha Toxin Monoclonal Antibodies That Reduce the Severity of *Staphylococcus aureus* Dermonecrosis and Exhibit a Correlation Between Affinity and Potency," Clinical and Vaccine Immunology, pp. 377-385.
Abouelkhair et al., (2018) "Characterization of Recombinant Wild-type and Nontoxigenic Protein A from *Staphylococcus pseudintermedius*", Virulence, 9(1): 1050-1061.

(Continued)

*Primary Examiner* — Robert A Zeman
(74) *Attorney, Agent, or Firm* — FisherBroyles, LLP; Cara L. Crowley-Weber; Gabrielle Amodeo

(57) ABSTRACT

Speciated antibodies or antigen-binding fragments that bind staphylococcal antigens are provided, where the antibodies and antigen-binding fragments have attenuated Fc binding to Protein A or homologous protein. Compositions comprising the antibodies and methods of use are also provided. The antibodies and compositions are useful for treating staphylococcal infection, reducing serum or kidney bacterial titers, and treating symptoms associated with staphylococcal infection. The antibodies may also prevent the severity and/or duration of the primary disease.

4 Claims, 10 Drawing Sheets

Figure 1:
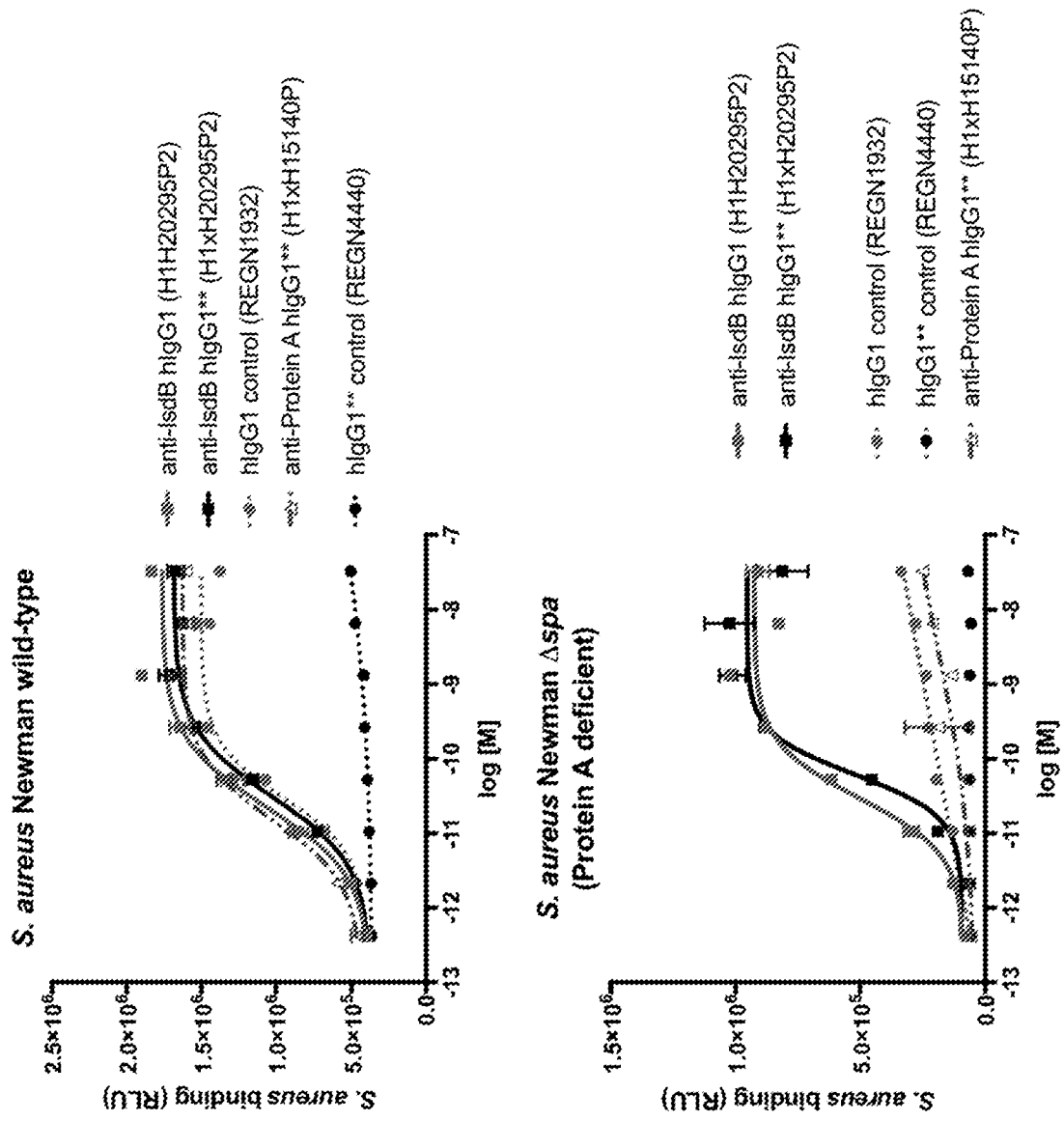

Specification includes a Sequence Listing.

(56) References Cited

OTHER PUBLICATIONS

Al-Lazikani et al., (1997) "Standard Conformations for the Canonical Structures of Immunoglobulins", J. Mol. Biol., 273:927-948.
Altschul et al., (1990) "Basic Local Alignment Search Tool", J. Mol. Biol., 215: 403-410.
Antibodies, Harlow and Lane (Cold Spring Harbor Press, Cold Spring Harbor, NY), 1988.
Arruebo et al., (2009) "Antibody-conjugated nanoparticles for biomedical applications", J. Nanomat. vol. 2009, Article ID 439389, 24 pages, doi: 10.1155/2009/439389.
Baba, et al., (2002) "Genome and virulence determinants of high virulence community-acquired MRSA", Lancet, 359 (9320):1819-27.
Balachandran et al., (2018) "Expression and Function of Protein A in *Staphylococcus pseudintermedius*", Virulence, 9(1): 390-401.
Bäumer et al., (2017) "Establishing a canine superficial pyoderma model", Journal of Applied Microbiology, 122(2): 331-337.
Bruhns, P. and F. Jonsson, (2015) "Mouse and human FcR effector functions", Immunol Rev, 268(1): 25-51.
Dobo et al., (2018) "Be on Target: Strategies of Targeting Alternative and Lectin Pathway Components in Complement-Mediated Diseases", Front Immunol, 9(1851):1-22.
Ehring, (1999) "Hydrogen Exchange/Electrospray Ionization Mass Spectrometry Studies of Structural Features of Proteins and Protein/Protein Interactions", Analytical Biochemistry, 267: 252-259.
Engen and Smith, (2001) "A powerful new approach that goes", Anal. Chem., 73: 256A-265A.
Gonnet et al. (1992) "Exhaustive Matching of the Entire Protein Sequence Database", Science, 256: 1443-1445.
Heidary et al., (2018) "Daptomycin", J Antimicrob Chemother, 73(1): 1-11.
Inganas, (1981) "Comparison of mechanisms of interaction between protein A from *Staphylococcus aureus* and human monoclonal IgG, IgA and IgM in relation to the classical FC gamma and the alternative F(ab')2 epsilon protein A interactions" Scand J Immunol, 13(4): 343-352.
International Search Report and Written Opinion for PCT/US2019/062370, dated Mar. 2, 2020, 19 pages.
Jendeberg et al., (1997) "Engineering of Fc1 and Fc3 from human immunoglobulin G to analyse subclass specificity for staphylococcal protein A", Journal of Immunological Methods, 201:25-34.
Junghans et al., (1990) "Anti-Tac-H, a Humanized Antibody to the Interleukin 2 Receptor with New Features for Immunotherapy in Malignant and Immune Disorders", Cancer Res., 50:1495-1502.
Kabat and Wu (1991) "Sequences of Proteins of Immunological Interest," National Institutes of Health, Bethesda, Md., 11 pages.
Kazane et al., (2013) "Self-Assembled Antibody Multimers through Peptide Nucleic Acid Conjugation" J. Am. Chem. Soc., 135:340-346.
Kim et al., (2010) "IsdA and IsdB antibodies protect mice against *Staphylococcus aureus* abscess formation and lethal challenge", Vaccine, 28(38):6382-6392.
Klein et al., (2012) "Progress in overcoming the chain association issue in bispecific heterodimeric IgG antibodies", mAbs, 4(6):653-663.
Kufer et al., (2004) "A revival of bispecific antibodies", Trends Biotechnol., 22:238-244.

Kuroda et al., (2001) "Whole genome sequencing of methicillin-resistant *Staphylococcus aureus*", Lancet, 357 (9264):1225-1240.
Langer (1990) "New Methods of Drug Delivery", Science, 249:1527-1533.
Lloyd (1999) The Art, Science and Technology of Pharmaceutical Compounding.
Lu et al., (2018) "Beyond binding: antibody effector functions in infectious diseases", Nat Rev Immunol, 18(1): 46-61.
Marone et al., (1987) "Mechanism of activation of human basophils by *Staphylococcus aureus* Cowan 1", Infect Immun, 55(3): 803-9.
Martin et al., (1989) "Modeling antibody hypervariable loops: A combined algorithm", Proc. Natl. Acad. Sci. USA, 86:9268-9272.
Padlan et al., (1995) "Identification of specificity-determining residues in antibodies", FASEB J., 9:133-139.
Pearson (1994) "Using the FASTA Program to Search Protein and DNA Sequence Databases", Methods Mol. Biol., 24: 307-331.
Powell et al., (1998) "Compendium of excipients for parenteral formulations", PDA J Pharm Sci Technol, 52:238-311.
Reineke (2004) "Antibody Epitope Mapping Using Arrays of Synthentic Peptides", Methods Mol. Biol., 248: 443-463.
Sasso et al., (1989) "Human IgM molecules that bind staphylococcal protein A contain VHIII H chains", J Immunol, 142(8): 2778-2783.
Shields et al., (2002) "Lack of Fucose on Human IgG1 N-Linked Oligosaccharide Improves Binding to Human FcγRIII and Antibody-dependent Cellular Toxicity", JBC, 277:26733-26740.
Silverman (1992) "Human antibody responses to bacterial antigens: studies of a model conventional antigen and a proposed model B cell superantigen", Int Rev Immunol, 9(1): 57-78.
Smith et al., (2015) "A novel, native-format bispecific antibody triggering T-cell killing of B-cells is robustly active in mouse tumor models and cynomolgus monkeys", Scientific Reports, 5:17943, 12 pages.
Thammavongsa et al., (2009) "*Staphylococcus aureus* synthesizes adenosine to escape host immune responses", J Exp Med., 206(11): 2417-2427.
Thammavongsa et al., (2015) "Staphylococcal manipulation of host immune responses", Nat Rev Microbiol, 13: 529-43.
Tomer et al., (2000) "Characterization of a discontinuous epitope of the human immunnodeficiency virus (HIV) core protein p24 by epitope excision and differential chemical modification followed by mass spectrometric peptide mapping analysis", Prot. Sci., 9: 487-496.
Tustian et al., (2016) "Development of purification processes for fully human bispecific antibodies based upon modification of protein A binding avidity", mAbs, 8(4):828-838.
Tutt et al., (1991) "Trispecific F(ab')3 Derivatives that use Cooperative Signaling via the TCR/CD3 Complex and CD2 to Activate and Redirect Resting Cytotoxic T Cells", J. Immunol., 147:60-69.
Van Loghem et al., (1982) "Staphylococcal Protein A and human IgG subclasses and allotypes", Scand. J. Immunol., 15, 275-278.
Vajdos et al., (2002) "Comprehensive Functional Maps of the Antigen-binding Site of an Anti-ErbB2 Antibody Obtained with Shotgun Scanning Mutagenesis", J Mol Biol, 320:415-428.
Wang and Lee, (2016), "Murine Models of Bacteremia and Surgical Wound Infection for the Evaluation of *Staphylococcus aureus* Vaccine Candidates", Methods Mol Biol, 1403: 409-418.
Wu et al. (1987), "Receptor-mediated in Vitro Gene Transformation by a Soluble DNA Carrier System", J. Biol. Chem., 262:4429-4432.

* cited by examiner

ANTI-*STAPHYLOCOCCUS* ANTIBODIES AND USES THEREOF

CROSS-REFERENCE TO RELATED APPLICATIONS

This application claims the benefit under 35 U.S.C § 119(e) of U.S. Provisional Application No. 62/865,436, filed Jun. 24, 2019, U.S. Provisional Application No. 62/822,029, filed Mar. 21, 2019, and U.S. Provisional Application No. 62/770,608, filed Nov. 21, 2018, which applications are herein specifically incorporated by reference in their entirety.

FIELD OF THE INVENTION

The present invention relates to human antibodies and antigen-binding fragments of human antibodies that specifically bind to *S. aureus* antigens but exhibit attenuated Fc binding to Protein A, compositions comprising these antibodies, and therapeutic methods of using these antibodies

SEQUENCE LISTING

An official copy of the sequence listing is submitted concurrently with the specification electronically via EFS-Web as an ASCII formatted sequence listing with a file name of "10495US01_SEQ_LIST_ST25.txt", a creation date of Nov. 20, 2019, and a size of about 96 KB. The sequence listing contained in this ASCII formatted document is part of the specification and is herein incorporated by reference in its entirety.

BACKGROUND

*Staphylococcus aureus* is an aerobic Gram-positive cocci bacterium that commonly colonizes the nose and skin of healthy humans. *Staphylococcus aureus* bacteria, sometimes also referred to as "Staph", "Staph. aureus", or "*S. aureus*", are considered opportunistic pathogens that cause minor infections such as pimples, boils and other soft tissue infections. However, *S. aureus* is a substantial cause of sickness and death in both humans and animals and systemic infection can cause endocarditis, arthritis, osteomyelitis, pneumonia, septic shock and even death. Hospital-acquired *S. aureus* infection is common and the most frequent cause of hospital-acquired surgical site infections and pneumonia. *S. aureus* infection is also the second most frequent cause of cardiovascular and bloodstream infections. Antibiotic administration is the standard treatment for *S. aureus* infections, but depending on the type of infection (e.g. skin infections are proportionally antibiotic-resistant) and the country, antibiotic resistant infections may be more prevalent. For example, methicillin-resistant *S. aureus* (MRSA) has evolved the ability to resist beta-lactam antibiotics such as penicillin and cephalosporins, and *S. aureus* resistant to vancomycin and linezolid are being encountered with regularity. New approaches for preventing and treating *S. aureus* infections are needed.

Intact skin and mucous membranes are natural barriers and protect against *S. aureus* infections. Injuries such as burns, trauma, and surgical procedures increase the risk of infection, as do diseases that compromise the immune system including diabetes, end-stage renal disease, and cancer. Opportunistic *S. aureus* infections can become serious, causing a variety of diseases or conditions, non-limiting examples of which include cellulitis, bacteremia, dermonecrosis, eyelid infection, eye infection, neonatal conjunctivitis, osteomyelitis, impetigo, boils, scalded skin syndrome, food poisoning, pneumonia, surgical infection, burn infection, meningitis, endocarditis, septicemia, toxic shock syndrome, or septic arthritis.

*S. aureus* expresses a number of surface determinant antigens, including the iron-regulated surface determinant proteins IsdA, IsdB, IsdC, IsdE and IsdH, *S. aureus* Protein A (SpA) and polysaccharide poly-N-aceytlglucosamine (PNAG), the clumping factor proteins ClfA and ClfB, capsular polysaccharide type (CP) 5 and CP8, the serine-aspartic acid repeat proteins SdrC, SdrD, and SdrE, fibronectin binding proteins A and B (FnBpA, FnBpB), Cna (collagen binding protein), and SasG (*S. aureus* surface protein G). These surface antigens play a role in colonization of host tissue, evasion of the host immune response, and bacterial fitness.

BRIEF SUMMARY

Provided herein are antibodies and antigen-binding fragments thereof that bind staphylococcal antigens, for example, *S. aureus* antigens or *S. pseudintermedius* antigens. These antibodies can have one or more of the following characteristics: (a) has attenuated Fc binding to Protein A or a Protein A homologue, such as SpsQ; (b) comprises H435R and Y436F mutations in the hIgG1 Fc (EU index numbering; equivalent to H318R and Y319F of SEQ ID NO: 58); and (c) comprises an hIgG1 heavy chain of SEQ ID NO: 58. The antibodies bind staphylococcal antigens, e.g. antigens from *S. aureus* or *S. pseudintermedius* and thus are useful in therapeutic treatment of staphylococcal infection and the symptoms and conditions associated with or caused by staphylococcal infection. In some aspects, the antibodies are directed to an antigen from one staphylococcal species, but may cross-react with another staphylococcal species, for example, the antibody cross-reacts with an antigen from both *S. aureus* and *S. pseudintermedius*. The antibody can have attenuated Fc binding to *S. pseudintermedius* SpsQ protein, and is thus useful in therapeutic treatment of *S. pseudintermedius* infection and the symptoms and conditions associated with or caused by *S. pseudintermedius* infection. In some aspects, the antibodies demonstrate antibody-dependent killing of *S. aureus* in human blood.

In some aspects the antibodies are fully human monoclonal antibodies, fully equine monoclonal antibodies, fully canine antibodies, fully feline antibodies, fully porcine antibodies, fully bovine antibodies, etc. The antibodies provided herein are speciated to as needed for the animal in which treatment is warranted. Antibodies of interest include humanized antibodies, or caninized, felinized, equinized, bovinized, porcinized, etc., antibodies, and variants thereof. Caninized and felinized antibodies are useful for applications in dogs and cats, respectively, and can be used in other species given the interspecies homology of the Fc region. Bovinized antibodies are useful for applications in cattle, for example, in treating mastitis and other staphylococcal infections.

Exemplary *S. aureus* antigens to which the antibodies are made include IsdA, IsdB, IsdC, IsdE, IsdH, Protein A, ClfA, ClfB, CP5, CP8, SdrC, SdrD, SdrE, FnBpA, FnBpB, Cna, polysaccharide poly-N-aceytlglucosamine (PNAG), and SasG. Thus, in some aspects, the antibody comprises a heavy chain variable domain and/or a light chain variable domain that specifically binds a *S. aureus* antigen selected from the group consisting of IsdA, IsdB, IsdC, IsdE, IsdH, Protein A, ClfA, ClfB, CP5, CP8, SdrC, SdrD, SdrE, FnBpA, FnBpB, Cna, polysaccharide poly-N-aceytlglucosamine (PNAG), and SasG.

Exemplary *S. pseudintermedius* antigens to which the antibodies are made include any surface proteins such as, for example, SpsA, SpsQ, and SpsR.

In some embodiments, the antibody or antigen-binding fragment thereof specifically binds to *S. aureus* Protein A. In some aspects, the antibody or antigen-binding fragment thereof has one or more of the following characteristics:
  (a) demonstrates a dissociation constant ($K_D$) of less than $10^{-9}$ as measured in a surface plasmon resonance assay;
  (b) binds *S. aureus* Newman WT with an $EC_{50}$ of less than $10^{-9}$;
  (c) demonstrates complement dependent killing of *S. aureus*;
  (d) reduces *S. aureus* kidney burden by 3-5 logs compared to untreated mice in a disseminated infection model;
  (e) demonstrates antibody-dependent killing of *S. aureus* in human blood;
  (f) cross-reacts with *S. aureus, S. intermedius*, and/or *S. pseudintermedius*;
  (g) mitigates interactions between the Fab of VH3 antibodies and *S. aureus* expressing Protein A; and
  (h) comprises a hIgG1 heavy chain sequence of SEQ ID NO: 58, or a substantially similar sequence thereof having at least 90%, at least 95%, at least 98% or at least 99% sequence identity thereto.

In some embodiments, the anti-Protein A antibody or antigen-binding fragment thereof comprises three heavy chain complementarity determining regions (CDRs) (HCDR1, HCDR2 and HCDR3) contained within the heavy chain variable region (HCVR) of SEQ ID NO: 18, or a substantially similar sequence thereof having at least 90%, at least 95%, at least 98% or at least 99% sequence identity thereto, and three light chain CDRs (LCDR1, LCDR2 and LCDR3) contained within the light chain variable region (LCVR) of SEQ ID NO: 26, or a substantially similar sequence thereof having at least 90%, at least 95%, at least 98% or at least 99% sequence identity thereto.

In some embodiments, the anti-Protein A antibody or antigen-binding fragment thereof comprises an HCDR1/HCDR2/HCDR3/LCDR1/LCDR2/LCDR3 amino acid sequence combination of SEQ ID NOs: 20/22/24/28/30/32.

In some embodiments, the anti-Protein A antibody or antigen-binding fragment thereof comprises an HCVR amino acid sequence of SEQ ID NO: 18, an LCVR amino acid sequence of SEQ ID NO: 26, and/or an HCVR/LCVR amino acid sequence pair of SEQ ID NOs: 18/26, or a substantially similar sequence thereof having at least 90%, at least 95%, at least 98% or at least 99% sequence identity thereto.

In some embodiments, the anti-Protein A antibody or antigen-binding fragment thereof comprises three heavy chain complementarity determining regions (CDRs) (HCDR1, HCDR2 and HCDR3) contained within the heavy chain variable region (HCVR) of SEQ ID NO: 60, or a substantially similar sequence thereof having at least 90%, at least 95%, at least 98% or at least 99% sequence identity thereto, and three light chain CDRs (LCDR1, LCDR2 and LCDR3) contained within the light chain variable region (LCVR) of SEQ ID NO: 68, or a substantially similar sequence thereof having at least 90%, at least 95%, at least 98% or at least 99% sequence identity thereto.

In some embodiments, the anti-Protein A antibody or antigen-binding fragment thereof comprises an HCDR1/HCDR2/HCDR3/LCDR1/LCDR2/LCDR3 amino acid sequence combination of SEQ ID NOs: 62/64/66/70/72/74.

In some embodiments, the anti-Protein A antibody or antigen-binding fragment thereof comprises an HCVR amino acid sequence of SEQ ID NO: 60, an LCVR amino acid sequence of SEQ ID NO: 68, and/or an HCVR/LCVR amino acid sequence pair of SEQ ID NOs: 60/68, or a substantially similar sequence thereof having at least 90%, at least 95%, at least 98% or at least 99% sequence identity thereto.

In some embodiments, the anti-Protein A antibody or antigen-binding fragment thereof comprises three heavy chain complementarity determining regions (CDRs) (HCDR1, HCDR2 and HCDR3) contained within the heavy chain variable region (HCVR) of SEQ ID NO: 80, or a substantially similar sequence thereof having at least 90%, at least 95%, at least 98% or at least 99% sequence identity thereto, and three light chain CDRs (LCDR1, LCDR2 and LCDR3) contained within the light chain variable region (LCVR) of SEQ ID NO: 88, or a substantially similar sequence thereof having at least 90%, at least 95%, at least 98% or at least 99% sequence identity thereto.

In some embodiments, the anti-Protein A antibody or antigen-binding fragment thereof comprises an HCDR1/HCDR2/HCDR3/LCDR1/LCDR2/LCDR3 amino acid sequence combination of SEQ ID NOs: 82/84/86/90/72/93.

In some embodiments, the anti-Protein A antibody or antigen-binding fragment thereof comprises an HCVR amino acid sequence of SEQ ID NO: 80, an LCVR amino acid sequence of SEQ ID NO: 88, and/or an HCVR/LCVR amino acid sequence pair of SEQ ID NOs: 80/88, or a substantially similar sequence thereof having at least 90%, at least 95%, at least 98% or at least 99% sequence identity thereto.

In some aspects, the anti-Protein A antibody comprises a heavy chain amino acid sequence of SEQ ID NO: 76, or a substantially similar sequence thereof having at least 90%, at least 95%, at least 98% or at least 99% sequence identity thereof. In some aspects, the anti-Protein A antibody comprises a light chain amino acid sequence of SEQ ID NO: 78, or a substantially similar sequence thereof having at least 90%, at least 95%, at least 98% or at least 99% sequence identity thereof.

In some aspects, the anti-Protein A antibody comprises a heavy chain amino acid sequence of SEQ ID NO: 95, or a substantially similar sequence thereof having at least 90%, at least 95%, at least 98% or at least 99% sequence identity thereof. In some aspects, the anti-Protein A antibody comprises a light chain amino acid sequence of SEQ ID NO: 97, or a substantially similar sequence thereof having at least 90%, at least 95%, at least 98% or at least 99% sequence identity thereof.

In some embodiments, the antibody or antigen-binding fragment thereof specifically binds to *S. aureus* IsdA. In some aspects, the anti-IsdA antibody has one or more of the following characteristics:
  (a) demonstrates a dissociation constant ($K_D$) of less than $10^{-8}$ as measured in a surface plasmon resonance assay;
  (b) reduces *S. aureus* kidney burden by 3-5 logs compared to untreated mice in a disseminated infection model;
  (c) demonstrates antibody-dependent killing of *S. aureus* in human blood; and
  (d) comprises a hIgG1 heavy chain sequence of SEQ ID NO: 58, or a substantially similar sequence thereof having at least 90%, at least 95%, at least 98% or at least 99% sequence identity thereto.

In some embodiments, the anti-IsdA antibody or antigen-binding fragment thereof comprises three heavy chain CDRs (HCDR1, HCDR2 and HCDR3) contained within the HCVR amino acid sequence of SEQ ID NO: 2, or a substantially similar sequence thereof having at least 90%, at least 95%, at least 98% or at least 99% sequence identity thereto, and three light chain CDRs (LCDR1, LCDR2 and LCDR3) contained within the LCVR amino acid sequence of SEQ ID NO: 10, or a substantially similar sequence thereof having at least 90%, at least 95%, at least 98% or at least 99% sequence identity thereto.

In some embodiments, the anti-IsdA antibody or antigen-binding fragment thereof comprises an HCDR1/HCDR2/HCDR3/LCDR1/LCDR2/LCDR3 amino acid sequence combination of SEQ ID NOs: 4/6/8/12/14/16.

In some embodiments, the anti-IsdA antibody or antigen-binding fragment thereof comprises an HCVR amino acid sequence of SEQ ID NO: 2, an LCVR amino acid sequence of SEQ ID NO: 10, and/or an HCVR/LCVR amino acid sequence pair of SEQ ID NOs: 2/10, or a substantially similar sequence thereof having at least 90%, at least 95%, at least 98% or at least 99% sequence identity thereto.

In some embodiments, the anti-IsdA antibody or antigen-binding fragment thereof comprises three heavy chain CDRs (HCDR1, HCDR2 and HCDR3) contained within the HCVR amino acid sequence of SEQ ID NO: 99, or a substantially similar sequence thereof having at least 90%, at least 95%, at least 98% or at least 99% sequence identity thereto, and three light chain CDRs (LCDR1, LCDR2 and LCDR3) contained within the LCVR amino acid sequence of SEQ ID NO: 107, or a substantially similar sequence thereof having at least 90%, at least 95%, at least 98% or at least 99% sequence identity thereto.

In some embodiments, the anti-IsdA antibody or antigen-binding fragment thereof comprises an HCDR1/HCDR2/HCDR3/LCDR1/LCDR2/LCDR3 amino acid sequence combination of SEQ ID NOs: 101/103/105/109/111/113.

In some embodiments, the anti-IsdA antibody or antigen-binding fragment thereof comprises an HCVR amino acid sequence of SEQ ID NO: 99, an LCVR amino acid sequence of SEQ ID NO: 107, and/or an HCVR/LCVR amino acid sequence pair of SEQ ID NOs: 99/107, or a substantially similar sequence thereof having at least 90%, at least 95%, at least 98% or at least 99% sequence identity thereto.

In some aspects, the anti-IsdA antibody comprises a heavy chain amino acid sequence of SEQ ID NO: 115, or a substantially similar sequence thereof having at least 90%, at least 95%, at least 98% or at least 99% sequence identity thereof. In some aspects, the anti-IsdA antibody comprises a light chain amino acid sequence of SEQ ID NO: 117, or a substantially similar sequence thereof having at least 90%, at least 95%, at least 98% or at least 99% sequence identity thereof.

In some embodiments, the isolated antibody or antigen-binding fragment thereof specifically binds to *S. aureus* IsdB. In some aspects, the anti-IsdB antibody has one or more of the following characteristics:
(a) binds *S. aureus* Newman WT with an $EC_{50}$ of less than $10^{-10}$;
(b) reduces *S. aureus* kidney burden in treated mice by about 1000 fold;
(c) demonstrates complement dependent killing of *S. aureus*;
(d) demonstrates antibody-dependent killing of *S. aureus* in human blood;
(e) comprises a heavy chain sequence of SEQ ID NO: 54, or a substantially similar sequence thereof having at least 90%, at least 95%, at least 98% or at least 99% sequence identity thereto; and (f) comprises a light chain sequence of SEQ ID NO: 52, or a substantially similar sequence thereof having at least 90%, at least 95%, at least 98% or at least 99% sequence identity thereto.

In some embodiments, the anti-IsdB antibody comprises: (a) three heavy chain CDRs (HCDR1, HCDR2 and HCDR3) contained within the HCVR amino acid sequence of SEQ ID NO: 34, or a substantially similar sequence thereof having at least 90%, at least 95%, at least 98% or at least 99% sequence identity thereto, and three light chain CDRs (LCDR1, LCDR2 and LCDR3) contained within the LCVR amino acid sequence of SEQ ID NO: 42, or a substantially similar sequence thereof having at least 90%, at least 95%, at least 98% or at least 99% sequence identity thereto, and (b) an hIgG1 heavy chain amino acid sequence of SEQ ID NO: 58, or a substantially similar sequence thereof having at least 90%, at least 95%, at least 98% or at least 99% sequence identity thereto.

In some embodiments, the anti-IsdB antibody or antigen-binding fragment thereof comprises an HCDR1/HCDR2/HCDR3/LCDR1/LCDR2/LCDR3 amino acid sequence combination of SEQ ID NOs: 36/38/40/44/46/48.

In some embodiments, the anti-IsdB antibody or antigen-binding fragment thereof comprises an HCVR amino acid sequence of SEQ ID NO: 34, an LCVR amino acid sequence of SEQ ID NO: 42, and/or an HCVR/LCVR amino acid sequence pair of SEQ ID NOs: 34/42, or a substantially similar sequence thereof having at least 90%, at least 95%, at least 98% or at least 99% sequence identity thereto.

In some embodiments the anti-IsdB antibody or antigen-binding fragment thereof comprises a heavy chain amino acid sequence of SEQ ID NO: 54, or a substantially similar sequence thereof having at least 90%, at least 95%, at least 98% or at least 99% sequence identity thereto.

In some embodiments the anti-IsdB antibody or antigen-binding fragment thereof comprises a light chain amino acid sequence of SEQ ID NO: 52, or a substantially similar sequence thereof having at least 90%, at least 95%, at least 98% or at least 99% sequence identity thereto.

In some embodiments, the anti-IsdB antibody comprises: (a) three heavy chain CDRs (HCDR1, HCDR2 and HCDR3) contained within the HCVR amino acid sequence of SEQ ID NO: 119, or a substantially similar sequence thereof having at least 90%, at least 95%, at least 98% or at least 99% sequence identity thereto, and three light chain CDRs (LCDR1, LCDR2 and LCDR3) contained within the LCVR amino acid sequence of SEQ ID NO: 127, or a substantially similar sequence thereof having at least 90%, at least 95%, at least 98% or at least 99% sequence identity thereto, and (b) an hIgG1 heavy chain amino acid sequence of SEQ ID NO: 58, or a substantially similar sequence thereof having at least 90%, at least 95%, at least 98% or at least 99% sequence identity thereto.

In some embodiments, the anti-IsdB antibody or antigen-binding fragment thereof comprises an HCDR1/HCDR2/HCDR3/LCDR1/LCDR2/LCDR3 amino acid sequence combination of SEQ ID NOs: 121/123/125/129/131/133.

In some embodiments, the anti-IsdB antibody or antigen-binding fragment thereof comprises an HCVR amino acid sequence of SEQ ID NO: 119, an LCVR amino acid sequence of SEQ ID NO: 127, and/or an HCVR/LCVR amino acid sequence pair of SEQ ID NOs: 119/127, or a substantially similar sequence thereof having at least 90%, at least 95%, at least 98% or at least 99% sequence identity thereto.

In some embodiments the anti-IsdB antibody or antigen-binding fragment thereof comprises a heavy chain amino acid sequence of SEQ ID NO: 135, or a substantially similar sequence thereof having at least 90%, at least 95%, at least 98% or at least 99% sequence identity thereto.

In some embodiments the anti-IsdB antibody or antigen-binding fragment thereof comprises a light chain amino acid sequence of SEQ ID NO: 137, or a substantially similar sequence thereof having at least 90%, at least 95%, at least 98% or at least 99% sequence identity thereto.

Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

Provided herein are nucleic acid molecules encoding the anti-*S. aureus* antibodies or fragments thereof described herein. For example, provided herein are nucleic acid molecules encoding any of the HCVR amino acid sequences listed in Tables 1 and 15; in certain embodiments the nucleic acid molecule comprises a polynucleotide sequence selected from any of the HCVR nucleic acid sequences listed in Tables 2 and 16, or a substantially similar sequence thereof having at least 90%, at least 95%, at least 98% or at least 99% sequence identity thereto.

Also provided herein are nucleic acid molecules encoding any of the LCVR amino acid sequences listed in Tables 1 and 15; in certain embodiments the nucleic acid molecule comprises a polynucleotide sequence selected from any of the LCVR nucleic acid sequences listed in Tables 2 and 16, or a substantially similar sequence thereof having at least 90%, at least 95%, at least 98% or at least 99% sequence identity thereto.

Also provided herein are nucleic acid molecules encoding any of the HCDR amino acid sequences listed in Tables 1 and 15 and any of the LCDR amino acid sequences listed in Tables 1 and 15; in certain embodiments the nucleic acid molecule comprises a polynucleotide sequence selected from any of the CDR nucleic acid sequences listed in Tables 2 and 16, or a substantially similar sequence thereof having at least 90%, at least 95%, at least 98% or at least 99% sequence identity thereto.

Provided herein are nucleic acid molecules encoding an HCVR, wherein the HCVR comprises a set of three CDRs (i.e., HCDR1, HCDR2, HCDR3), wherein the HCDR1, HCDR2, HCDR3 amino acid sequence set is as defined by any of the exemplary antibodies listed in Tables 1 and 15.

Also provided herein are nucleic acid molecules encoding an LCVR, wherein the LCVR comprises a set of three CDRs (i.e., LCDR1, LCDR2, LCDR3), wherein the LCDR1, LCDR2, LCDR3 amino acid sequence set is as defined by any of the exemplary antibodies listed in Tables 1 and 15.

Provided herein are nucleic acid molecules encoding both an HCVR and an LCVR, wherein the HCVR comprises an amino acid sequence of any of the HCVR amino acid sequences listed in Tables 1 and 15, and wherein the LCVR comprises an amino acid sequence of any of the LCVR amino acid sequences listed in Tables 1 and 15. In certain embodiments, the nucleic acid molecule comprises a polynucleotide sequence selected from any of the HCVR nucleic acid sequences listed in Tables 2 and 16, or a substantially similar sequence thereof having at least 90%, at least 95%, at least 98% or at least 99% sequence identity thereto, and a polynucleotide sequence selected from any of the LCVR nucleic acid sequences listed in Tables 2 and 16, or a substantially similar sequence thereof having at least 90%, at least 95%, at least 98% or at least 99% sequence identity thereto. In certain embodiments according to this aspect of the invention, the nucleic acid molecule encodes an HCVR and LCVR, wherein the HCVR and LCVR are both derived from the same antibody listed in Tables 1 and 15.

Provided herein are recombinant expression vectors capable of expressing a polypeptide comprising a heavy or light chain variable region of an anti-Protein A antibody, an anti-IsdA antibody, or an anti-IsdB antibody. For example, this includes recombinant expression vectors comprising any of the nucleic acid molecules mentioned above, i.e., nucleic acid molecules encoding any of the HCVR, LCVR, and/or CDR sequences as set forth in Tables 1 and 15. Also included within the scope of the present invention are host cells into which such vectors have been introduced, as well as methods of producing the antibodies or portions thereof by culturing the host cells under conditions permitting production of the antibodies or antibody fragments, and recovering the antibodies and antibody fragments so produced.

In another aspect, the invention provides a pharmaceutical composition comprising a recombinant human antibody or fragment thereof which specifically binds Protein A, IsdA, or IsdB, and a pharmaceutically acceptable carrier. In a related aspect, the composition is a combination of an anti-Protein A antibody and a second therapeutic agent. In one embodiment, the second therapeutic agent is any agent that is advantageously combined with an anti-Protein A antibody.

In a related aspect, the composition is a combination of an anti-IsdA antibody and a second therapeutic agent. In one embodiment, the second therapeutic agent is any agent that is advantageously combined with an anti-IsdA antibody.

In a related aspect, the composition is a combination of an anti-IsdB antibody and a second therapeutic agent. In one embodiment, the second therapeutic agent is any agent that is advantageously combined with an anti-IsdB antibody.

In yet another aspect, the invention provides therapeutic methods for treating a staphylococcal infection, disorders associated with a staphylococcal infection, and/or the symptoms of a staphylococcal infection. The therapeutic methods according to this aspect comprise administering a therapeutically effective amount of a pharmaceutical composition comprising an antibody or antigen-binding fragment of an antibody provided herein, having attenuated Fc binding, to a subject in need thereof. The disorder treated is any disease or condition which is improved, ameliorated, inhibited or prevented by interfering with staphylococcal complement evasion and/or by permitting antibody-induced serum killing.

In yet another aspect, the invention provides therapeutic methods for treating a *S. aureus* infection, disorders associated with a *S. aureus* infection, and/or the symptoms of a *S. aureus* infection. The therapeutic methods according to this aspect comprise administering a therapeutically effective amount of a pharmaceutical composition comprising an antibody or antigen-binding fragment of an antibody provided herein to a subject in need thereof. The disorder treated is any disease or condition which is improved, ameliorated, inhibited or prevented by interfering with *S. aureus* complement evasion and/or by permitting antibody-induced serum killing.

In yet another aspect, the invention provides therapeutic methods for treating a *S. pseudintermedius* infection, disorders associated with a *S. pseudintermedius* infection, and/or the symptoms of a *S. pseudintermedius* infection. The therapeutic methods according to this aspect comprise administering a therapeutically effective amount of a pharmaceutical composition comprising an antibody or antigen-binding fragment of an antibody provided herein to a subject in need thereof. The disorder treated is any disease or condition which is improved, ameliorated, inhibited or prevented by interfering with *S. pseudintermedius* complement evasion and/or by permitting antibody-induced serum killing.

Other embodiments will become apparent from a review of the ensuing detailed description.

BRIEF DESCRIPTION OF THE FIGURES

FIG. 1 shows the effects of the */* modification on Anti-IsdB antibodies and Anti-Protein A antibodies on binding to *S. aureus* Newman wild-type and Protein A deficient strains to characterize the specificity of antibody binding in the presence and absence of Protein A.

FIG. 2 demonstrates that both the anti-Protein A and anti-IsdB hIgG1*/* monoclonal antibodies promote *S. aureus* Newman killing in normal human serum.

FIG. 3 shows the effectiveness of the anti-IsdB*/* antibody in reducing *S. aureus* kidney burden relative to the non-modified anti-IsdB antibody.

FIG. 4 demonstrates that both the anti-Protein A and anti-IsdB hIgG1*/* monoclonal antibodies promote killing of *S. aureus* Newman, N315 or MW2 in normal human serum relative to the non-modified antibodies.

FIG. 5 shows the effectiveness of the anti-IsdB*/* and anti-Protein A */* antibodies in reducing *S. aureus* kidney burden relative to the non-modified antibodies.

FIG. 6 demonstrates that complement component C3 is required for efficacy of anti-IsdB and anti-Protein A hIgG1*/* monoclonal antibodies.

FIG. 7 demonstrates that low affinity FcgRIIb/FcgRIII/FcgRIV are not required for efficacy of anti-IsdB and anti-Protein A hIgG1*/* monoclonal antibodies.

FIG. 8 shows the effectiveness of the anti-Protein A, IsdA and IsdB hIgG1*/* monoclonal antibodies to promote killing of *S. aureus* Newman after 16 hours in human serum.

FIG. 9 shows the effectiveness of the anti-Protein A, IsdA and IsdB hIgG1*/* monoclonal antibodies in reducing *S. aureus* kidney burden when administered one day post-infection.

FIG. 10 demonstrates *S. aureus* survival in whole human blood treated with control hIgG1*/* monoclonal antibody compared to anti-Protein A, anti-IsdA and anti-IsdB hIgG1*/* monoclonal antibodies. Treatment with the control antibody did not impact viability of *S. aureus* while the anti-Protein A, anti-IsdA and anti-IsdB hIgG1*/* monoclonal antibodies induced antibody-dependent killing of *S. aureus*.

DETAILED DESCRIPTION

It is to be understood that this disclosure is not limited to particular methods and experimental conditions described, as such methods and conditions may vary. It is also to be understood that the terminology used herein is for the purpose of describing particular embodiments only, and is not intended to be limiting, since the scope will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Definitions

The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). Each light chain is comprised of a light chain variable region ("LCVR or "$V_L$") and a light chain constant region (CL). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4.

The monoclonal antibodies and antigen-binding fragments thereof that specifically bind a staphylococcal antigen as provided herein have attenuated Fc binding to Protein A (and/or SpsQ or other homologous protein). Throughout the disclosure this is noted as "*/*" or "**", and refers to antibodies, or antigen-binding fragments thereof, comprising H435R and Y436F mutations in the hIgG1 Fc according to EU index numbering. The H435R and Y436F mutations are equivalent to H318R and Y319F of SEQ ID NO: 58, an hIgG1 heavy chain. While the */* mutation position refers to H435R and Y436F according to EU numbering, the */* mutation can be found at different positions in the actual heavy chain for a given antibody (or antigen-binding fragment thereof) depending on the variable domain sequence lengths.

For example, */* mutations can be found in the full length heavy chain sequence for H1xH20295P2 at amino acid residue positions 443/444 in SEQ ID NO: 54; for H1xH15135P at amino acid residue positions 444/445 in SEQ ID NO: 76; for H1xH15120P at amino acid residue positions 436/437 in SEQ ID NO: 95; for H1xH20207P at amino acid residue positions 439/440 in SEQ ID NO: 115; and for H1xH20286P at amino acid residue positions 436/437 in SEQ ID NO: 135.

In an exemplary H1H20295P2 antibody without the */* mutation, the corresponding full length heavy chain amino acid residues found at positions 443/444 of SEQ ID NO: 50 are histidine/tyrosine.

In certain embodiments of the invention, the FRs of the antibody (or antigen binding fragment thereof) may be identical to the human germline sequences, or may be naturally or artificially modified. An amino acid consensus sequence may be defined based on a side-by-side analysis of two or more CDRs.

In certain embodiments, the framework regions of the antibody (or antigen binding fragment thereof) may be identical to the human germline sequences, for example, identical to the sequences of the antibodies provided herein, or may be naturally or artificially modified. One or more amino acids in a given framework region (or one or more framework regions) can be substituted, and the substitution(s) can be conservative or non-conservative. Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428). Thus, the antibodies provided herein can be effectively modified in the CDR regions and/or the framework regions, as long as the modified antibody maintains one or more desirable characteristics associated with the reference antibody lacking the modification.

Modifications to a given CDR can be made relative to a CDR sequence from an antibody provided herein, and the modifications can include conservative or non-conservative substitutions. Desirable substitutions can be determined by molecular modeling and/or empirically. For example, one or more CDR residues can be substituted with an amino acid occupying the corresponding position in another human antibody sequence or a consensus of such sequences.

Furthermore, an antigen-binding fragment thereof can be an antibody disclosed herein but modified to omit one or more CDRs and/or one or more framework regions, as long as the modified antibody (a.k.a., antigen-binding fragment) maintains binding to the respective S. aureus antigen.

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The monoclonal antibodies that specifically bind a staphylococcal antigen with attenuated Fc binding to Protein A (and/or SpsQ or other homologous protein) as disclosed herein may comprise one or more amino acid substitutions, insertions and/or deletions in the framework and/or CDR regions of the heavy and light chain variable domains as compared to the corresponding germline sequences, or as compared to the sequences provided herein. Such modifications or mutations can be readily ascertained by comparing the amino acid sequences disclosed herein to germline sequences available from, for example, public antibody sequence databases, or by comparing the amino acid sequences to those of the antibodies provided herein, for example, any one of the antibody sequences provided in the tables in the Examples.

The present disclosure includes antibodies, and antigen-binding fragments thereof, which are derived from any of the amino acid sequences disclosed herein, wherein one or more amino acids within one or more framework and/or CDR regions are modified to the corresponding residue(s) of the germline sequence from which the antibody was derived, or to the corresponding residue(s) of another germline sequence, e.g. human, canine, feline, bovine, porcine, equine, etc., or to a conservative amino acid substitution of the corresponding germline residue(s) (such sequence changes are referred to herein collectively as "germline mutations"), or compared to the amino acid sequences of those of the antibodies provided herein, for example, any one of the antibody sequences provided in the tables included in the Examples, as long as the antibody or antigen-binding fragment maintains the desirable characteristics relative to the reference antibody. A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies disclosed herein may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present disclosure.

Also included herein are fully human antibodies, fully bovine antibodies, fully canine antibodies, fully equine antibodies, etc., to S. aureus antigens comprising variants of any of the HCVR, LCVR, and/or CDR amino acid sequences disclosed herein having one or more conservative substitutions. For example, anti-Protein A antibodies can have HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein; anti-IsdA antibodies can have HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein; and anti-IsdB antibodies can have HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The phrase "human antibody", as used herein, is intended to include antibodies having variable and constant regions derived from human germline immunoglobulin sequences; likewise, an antibody may be speciated for treatment in a given animal. The speciated antibodies may include amino acid residues not encoded by the respective germline immunoglobulin sequences of that species (e.g., mutations introduced by random or site-specific mutagenesis in vitro or by somatic mutation in vivo), for example in the CDRs and in particular CDR3.

The term "human antibody", as used herein, is not intended to include monoclonal antibodies in which CDR sequences derived from the germline of another mammalian species (e.g., mouse), have been grafted onto human FR sequences. The term includes antibodies recombinantly produced in a non-human mammal, or in cells of a non-human mammal. The term is not intended to include antibodies isolated from or generated in a human subject.

As used herein the term "speciated framework region" (e.g. caninized or human) refers to the amino acid sequence of the heavy chain and light chain of a canine antibody other than the hypervariable region residues defined herein as CDR residues. The phrase "speciated antibody", as used herein, refers to an antibody having amino acid sequences of the human CDRs, for example, in both chains and a species specific framework region. In other words, a speciated antibody comprises a species specific IgG heavy chain comprising CDRs from an antibody from a first species (e.g., CDRs from a human antibody) and a kappa light chain from a second species comprising CDRs of an antibody from the first species, and indicates that the speciated antibody comprises a IgG heavy chain from the second species (or a modified IgG, e.g., as disclosed herein), which comprises the specified CDRs of the antibody from that first species in place of its CDRs and a kappa light chain from the second species (or a modified canine kappa light chain), which comprises the specified CDRs of the antibody from the first species in place of its CDRs.

The term "recombinant", as used herein, refers to antibodies or antigen-binding fragments thereof of the invention created, expressed, isolated or obtained by technologies or methods known in the art as recombinant DNA technology which include, e.g., DNA splicing and transgenic expression. The term refers to antibodies expressed in a non-human mammal (including transgenic non-human mammals, e.g., transgenic mice), or a cell (e.g., CHO cells) expression system or isolated from a recombinant combinatorial human antibody library.

The term "specifically binds," or "binds specifically to", or the like, means that an antibody or antigen-binding fragment thereof forms a complex with an antigen that is relatively stable under physiologic conditions. Specific binding can be characterized by an equilibrium dissociation constant of at least about $1\times10^{-7}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies have been identified by surface plasmon resonance, e.g., BIACORE™, which bind specifically to staphylococcal antigens but have attenuated Fc binding to Protein A and/or SpsQ or another homologous protein. Moreover, multi-specific antibodies that bind to one staphylococcal antigen and one or more additional antigens or a bi-specific that binds to two different staphylococcal antigens are nonetheless considered antibodies that "specifically bind", as used herein.

The term "high affinity" antibody refers to those monoclonal antibodies having a binding affinity to a staphylococcal antigen, such as a S. aureus antigen, expressed as $K_D$, of at least $10^{-7}$ M; preferably $10^{-8}$ M; more preferably $10^{-8}$ M, even more preferably $10^{-10}$ M, even more preferably $10^{-11}$ M, even more preferably $10^{-12}$ M, as measured by surface plasmon resonance, e.g., BIACORE™ or solution-affinity ELISA.

By the term "slow off rate", "Koff" or "kd" is meant an antibody that dissociates from the antigen with a rate constant of $1\times10^{-2}$ s$^{-1}$ or less, $1\times10^{-3}$ s$^{-1}$ or less, preferably $1\times10^{-4}$ s$^{-1}$ or less, as determined by surface plasmon resonance, e.g., BIACORE™.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refer to one or more fragments of an antibody that retain the ability to bind to a staphylococcal antigen and also exhibit attenuated Fc binding to Protein A or a homologous protein. Such terms can also refer to one or more fragments of an antibody that cross-react with, for example, S. aureus and S. pseudintermedius, or bind to a S. pseudintermedius antigen, and also exhibit attenuated Fc binding to SpsQ.

In specific embodiments, antibody or antibody fragments of the invention may be conjugated to a moiety such a ligand or a therapeutic moiety ("immunoconjugate"), such as an antibiotic, a second antibody to a staphylococcal antigen, or any other therapeutic moiety useful for treating an infection caused by staphylococcal infection.

An "isolated antibody", as used herein, is intended to refer to an antibody that is substantially free of other antibodies (Abs) having different antigenic specificities (e.g., an isolated antibody that specifically binds a staphylococcal antigen, or a fragment thereof, is substantially free of antibodies that specifically bind antigens other than the specified staphylococcal antigen.

"Antibody-dependent cell-mediated cytotoxicity" or "ADCC" is a mechanism of cell-mediated immune defense whereby an effector cell of the immune system actively lyses a target cell, whose membrane-surface antigens have been bound by specific antibodies, such as by those described herein. As such, it is one mechanism through which, for example, a S. aureus specific antibody or a S. pseudintermedius antibody, can act to limit the spread of infection. Classical ADCC is mediated by natural killer cells (NK cells), macrophages, neutrophils and in certain instances, eosinophils.

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen-binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "cross-competes", as used herein, means an antibody or antigen-binding fragment thereof binds to an antigen and inhibits or blocks the binding of another antibody or antigen-binding fragment thereof. The term also includes competition between two antibodies in both orientations, i.e., a first antibody that binds and blocks binding of second antibody and vice-versa. In certain embodiments, the first antibody and second antibody may bind to the same epitope. Alternatively, the first and second antibodies may bind to different, but overlapping epitopes such that binding of one inhibits or blocks the binding of the second antibody, e.g., via steric hindrance. Cross-competition between antibodies may be measured by methods known in the art, for example, by a real-time, label-free bio-layer interferometry assay. To determine if a test antibody cross-competes with a reference antibody described herein, the reference antibody is allowed to bind to an antibody to a S. aureus antigen under saturating conditions. Next, the ability of a test antibody to bind to the same antigen is assessed. If the test antibody is able to bind to the antigen following saturation binding with the reference antibody, it can be concluded that the test antibody binds to a different epitope than the reference antibody. On the other hand, if the test antibody is not able to bind to the S. aureus antigen following saturation binding with the reference antibody, then the test antibody may bind to the same epitope as the epitope bound by the reference antibody of the invention.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in %, for example at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% of the nucleotide bases, as measured by any well-known algorithm of sequence identity, such as FASTA, BLAST or GAP, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% sequence identity. In some aspects, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215: 403-410 and (1997) Nucleic Acids Res. 25:3389-3402, each of which is herein incorporated by reference.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

As used herein, the term "subject" refers to an animal, for example, a mammal, including a human, in need of amelioration, prevention and/or treatment of a staphylococcal infection such as a *S. aureus* infection or a disorder associated with a *S. aureus* infection, or a symptom associated with a *S. aureus* infection, or a *S. pseudintermeditis* infection or a disorder associated with a *S. pseudintermeditis* infection, or a symptom associated with a *S. pseudintermedius* infection. The subject can be a human or a non-human primate, a domestic animal such as a horse, cow, goat, sheep, or pig, or a companion animal. The phrase "companion animal" as used herein includes any non-human animal suitable for being kept as a pet by humans including a dog, a cat, and a rodent. The term "dog" includes companion animals and working dogs. The term dog is synonymous with the term canine. The term "cat" includes those which are companion animals known as domestic cats or house cats, otherwise known as felines. The term "rodent" includes, but is not limited to, hamsters, mice, rats, guinea pigs, gerbils, rabbits, hedge hogs, ferrets, chinchillas, etc. A subject can also include any animal kept in captivity.

The subject may have a staphylococcal infection or is predisposed to developing a staphylococcal infection, e.g. *S. aureus* infection or *S. pseudintermedius* infection. Subjects "predisposed to developing an staphylococcal infection", or subjects "who may be at elevated risk for contracting an staphylococcal infection", are those subjects with compromised immune systems because of autoimmune disease, burn victims, diabetic persons, surgery patients, those persons who have suffered an injury, those persons with a catheter, dialysis patients, those persons receiving immunosuppressive therapy (for example, following organ transplant), those persons afflicted with human immunodeficiency syndrome (HIV) or acquired immune deficiency syndrome (AIDS), certain forms of anemia that deplete or destroy white blood cells, those persons receiving radiation or chemotherapy, or those persons afflicted with an inflammatory disorder. Additionally, subjects of extreme young or old age are at increased risk. Any person who comes into physical contact or close physical proximity with an infected animal, or human patient, or is exposed to bodily fluids or tissues from an infected animal or human patient, has an increased risk of developing an *S. aureus* infection or *S. pseudintermedius* infection. Animals can be predisposed as well, for many of the above reasons or because the animal is producing milk, for example, a lactating cow, goat, horse, sheep, dog, or cat.

As used herein, the terms "treat", "treating", or "treatment" refer to the reduction or amelioration of the severity of the staphylococcal infection, for example, a *S. aureus* infection or a *S. pseudintermedius* infection, of at least one symptom or indication of staphylococcal infection, for example, a *S. aureus* infection or a *S. pseudintermedius* infection, or of a condition associated with or caused by a staphylococcal infection, for example, a *S. aureus* infection or a *S. pseudintermedius* infection, due to the administration of a therapeutic agent such as an antibody provided herein to a subject in need thereof. The terms include inhibition of progression of disease or of worsening of infection. The terms also include positive prognosis of disease, i.e., the subject may be free of infection or may have reduced or no bacterial titers upon administration of a therapeutic agent such as an antibody of the present invention. The therapeutic agent may be administered at a therapeutic dose to the subject.

As used herein "prevention" of staphylococcal-associated infection refers to reducing the risk of a subject acquiring staphylococcal-associated infection at the time of the infection event. In some aspects, the risk of a subject acquiring staphylococcal-associated infection is reduced by at least 30% as compared to a subject that has not been administered an isolated antibody or antigen-binding fragment thereof that immunospecifically binds to a staphylococcal antigen prior to the infection event. More suitably the risk is reduced by at least 40%, at least 50%, at least 60%, at least 70%, at least 80%, at least 90% or the risk is completely eliminated as compared to a subject that has not been administered an isolated antibody or antigen-binding fragment thereof that immunospecifically binds to a staphylococcal antigen prior to the infection event.

As used herein "reducing the severity" as it is used with reference to staphylococcal infection, for example, a *S. aureus* infection or a *S. pseudintermedius* infection, refers to reducing the symptoms that a subject that has acquired staphylococcal infection, for example, a *S. aureus* infection or a *S. pseudintermedius* infection, is exhibiting. Suitably, the symptoms are reduced by at least 30% as compared to the symptoms that a subject that also has acquired staphylococcal infection, for example, a *S. aureus* infection or a *S. pseudintermedius* infection, is exhibiting, but the subject has not been administered an isolated antibody or antigen-binding fragment thereof that immunospecifically binds to a staphylococcal antigen. More suitably the symptoms are reduced by at least 40%, at least 50%, at least 60%, at least 70%, at least 80%, at least 90% or the symptoms are completely eliminated (i.e., the subject is cured of the infection, for example, cured of sepsis) as compared to a subject that has not been administered an isolated antibody or antigen-binding fragment thereof that immunospecifically binds to a *S. aureus* toxin or surface determinant, or a combination thereof prior to the infection event.

Some or all of the staphylococcal infection associated conditions and symptoms may involve the direct action of secreted toxins as a component of infection or mediator of the condition or disease state, while some or all of the conditions may involve the indirect or secondary action of secreted toxins (e.g., as primary virulence factors that cause the main symptom or majority of symptoms associated with the condition, or as agents that act to further advance the disease through disruption of cellular function or cell lysis).

As used herein, the term "antibiotic" refers to any anti-infective agent or therapy, whether it be a chemical moiety, or a biological therapy, used to treat, prevent, or ameliorate a staphylococcal infection in a subject. For example, an antibiotic can be selected from the group consisting of penicillin, oxacillin, rifampin, flucloxacillin, dicloxacillin, cefazolin, cephalothin, cephalexin, nafcillin, clindamycin, lincomycin, linezolid, daptomycin, erythromycin, vancomycin, gentamicin, doxycycline, and trimethoprim-sulfamethoxazole, or can be any other antibiotic suitable to treat staphylococcal infection.

*Staphylococcus* and Associated Antigens

*S. aureus* infections can range from mild skin infections to severe infections including sepsis and endocarditis. As the bacteria are increasingly found in a drug-resistant form, particularly in health care settings such as hospitals and clinics, alternative treatments are needed.

*S. aureus* are notorious for evading the host immune system by expression of Protein A. Protein A functions to bind the Fc portion of the host antibodies and prevent antibody mediated bacterial killing, contributing to bacterial virulence. In addition, Protein A binds the Fc region of IgG1 and prevents complement fixation.

*Staphylococcus pseudintermedius* is primarily identified in dogs and has been identified in cats, horses, and humans. *S. pseudintermedius* is typically restricted to skin infection (pyoderma), but is also found in postoperative infections. SpsQ is a Protein A ortholog that functions analogously to and has 70% identity to Protein A. *S. pseudintermedius* has a high rate of methicillin resistance (MRSP).

In an effort to minimize the impact of Fc binding to Protein A, provided herein are antibodies to various *S. aureus* antigens having attenuated Fc binding to Protein A. In some aspects, the antibodies comprise H435R and Y436F mutations in the hIgG1 Fc (EU index numbering; equivalent to H318R and Y319F of SEQ ID NO: 58). In some aspects, the antibodies comprise an hIgG1 heavy chain of SEQ ID NO: 58. Likewise, in an effort to minimize the impact of Fc binding to SpsQ, provided herein are antibodies which cross-react with *S. pseudintermedius* and have attenuated Fc binding to SpsQ.

Disclosed herein are antibodies, including speciated antibodies such as human, humanized, canine, caninized, bovine, bovinized and/or chimeric forms, as well as fragments, derivatives/conjugates and compositions thereof, that bind to staphylococcal antigens such as surface determinant antigens and secreted toxins. Such antibodies can be useful for detecting and/or visualizing staphylococcal bacteria, such as *S. aureus* and *S. pseudintermedius*, and therefore may be useful in diagnostic methods and assays. Antibodies described herein also interfere with staphylococcal surface determinants, thereby interfering with colonization and immune evasion, making the antibodies useful for therapeutic and prophylactic methods. Likewise, antibodies described herein can bind staphylococcal secreted toxins, thereby reducing the virulence of staphylococcal infection.

Illustratively, *S. aureus* express antigens that are important for *S. aureus* colonization, immune evasion, and fitness. Such *S. aureus* antigens include, for example, IsdA, IsdB, IsdC, IsdE, IsdH, Protein A, ClfA, ClfB, CP5, CP8, SdrC, SdrD, SdrE, FnBpA, FnBpB, Cna, polysaccharide poly-N-aceytlglucosamine (PNAG), and SasG. Antibodies provided herein can target these antigens, and are particularly well suited to target the specific antigen given the IgG1*/* mutation which attenuates Fc binding to Protein A. Other staphylococcal bacteria express similar antigens, to which the antibodies provided herein can target in combination with a mutation which attenuates Fc binding to Protein A or a homologous protein.

*S. aureus* also produce a large number of secreted and cell-associated proteins, many of which are involved in pathogenesis, such as alpha-toxin (AT), beta-toxin, gamma-toxin, delta-toxin, leukocidin, toxic shock syndrome toxin (TSST), enterotoxins, coagulase, Protein A, and fibrinogen. Alpha toxin is one of the virulence factors of *S. aureus* and is produced by the majority of pathogenic *S. aureus* strains.

*S. aureus* infection as used herein refers to any minor to serious colonization of a subject with *S. aureus* bacteria. *S. aureus* infection can be acute or chronic. Exemplary conditions caused by *S. aureus* infection include cellulitis, bacteremia, dermonecrosis, eyelid infection, eye infection, neonatal conjunctivitis, osteomyelitis, impetigo, boils, scalded skin syndrome, food poisoning, pneumonia, surgical infection, burn infection, urinary tract infection, meningitis, endocarditis, septicemia, toxic shock syndrome, and septic arthritis. Exemplary symptoms of *S. aureus* infection include itching, redness, rash, swelling, nausea, vomiting, diarrhea, dehydration, low blood pressure, fever, confusion, muscle aches, abdominal pain, joint swelling, and joint pain.

The speciated antibodies and antigen-binding fragments provided herein specifically bind to staphylococcal antigens, for example, *S. aureus* antigens such as Protein A, IsdA, and IsdB, and exhibit attenuated Fc binding to Protein A and/or SpsQ. These antibodies bind to the respective antigen with high affinity, and can mediate antibody-dependent killing of *S. aureus*. These antibodies can also mediated antibody-dependent killing of *S. pseudintermedius*.

In some embodiments, the antibodies are useful for treating a subject suffering from *S. aureus* infection, or for preventing a *S. aureus* infection. When administered to a subject, the antibodies can decrease bacterial loads, for example, in serum and kidneys. The antibodies can be used prophylactically (before infection) to protect a subject from infection, or can be used therapeutically (after infection is established) to ameliorate a previously established infection, or to ameliorate at least one symptom associated with the infection.

In some embodiments, the antibodies are useful for treating a subject suffering from *S. pseudintermedius* infection, or for preventing a *S. pseudintermedius* infection. When administered to a subject, the antibodies can decrease bacterial loads, for example, in skin, serum and kidneys. The antibodies can be used prophylactically (before infection) to protect a subject from infection, or can be used therapeutically (after infection is established) to ameliorate a previously established infection, or to ameliorate at least one symptom associated with the infection.

In certain embodiments, the antibodies provided herein are obtained from mice immunized with a primary immunogen, such as a full-length Protein A protein, a full-length IsdA protein, or a full-length IsdB protein, or with a recombinant form of the respective antigen or fragment thereof followed by immunization with a secondary immunogen. The immunogen may be a biologically active and/or immunogenic fragment of a *S. aureus* antigen or DNA encoding the active fragment thereof.

Certain antibodies disclosed herein are able to bind to and reduce *S. aureus* bacterial load, as determined by in vitro or in vivo assays. The ability of the antibodies of the invention to bind to a *S. aureus* antigen may be measured using any standard method known to those skilled in the art, including binding assays, or activity assays, as described herein.

Certain antibodies disclosed herein are able to bind to and reduce *S. pseudintermedius* bacterial load, as determined by in vitro or in vivo assays.

Non-limiting, exemplary in vitro assays for measuring binding activity are illustrated in Example 3, herein. In Example 3, the binding affinity and dissociation constants of exemplary antibodies to *S. aureus* antigens were determined by Biacore. Example 4 provides specificity of antibody binding in the presence of Protein A. In Examples 5 and 6, in vitro and in vivo experiments were performed to demonstrate capacity of the antibodies to facilitate antibody-induced killing and to reduce bacterial load in kidneys, respectively.

The antibodies provided herein may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface. In one embodiment, the label may be a radionuclide, a fluorescent dye or a MRI-detectable label. In certain embodiments, such labeled antibodies may be used in diagnostic assays including imaging assays.

IgG1*/* Antibodies

It has been reported (Jendeberg, L. et al. (1997) J. Immunological Meth. 201:25-34)) that the inability of IgG3 to bind Protein A is determined by a single amino acid residue, Arg435 (EU numbering; Arg95 by IMGT), which corresponding position in the other IgG subclasses is occupied by a histidine residue. Provided herein are antibodies having IgG1 sequences in which His435 is mutated to Arg. Also provided herein are antibodies having IgG1 sequences in which Tyr436 is mutated to Phe. Further provided herein are antibodies having IgG1 sequences in which His435 is mutated to Arg and Tyr436 is mutated to Phe. Thus, these mutations in IgG1 provide antibodies specific to S. aureus having attenuated Fc binding to Protein A and/or SpsQ. This modification is referred to herein as IgG1*/*, denoting a modified IgG1 having the two described mutations (H435R/Y436F, aka hIgG1*/*; PMCID: 4675964, Smith et al., Sci Rep. 2015; 5: 17943). The resulting mutant IgG1 sequence in the vicinity of the alteration is identical to that of IgG3 and would therefore be expected to be immunologically "invisible," because there would be no non-native short peptides available for presentation to T cells, thus diminishing the potential immunogenicity.

In some embodiments, amino acid residue 435 (i.e., EU index numbering) from the heavy chain constant region is substituted with Arg, resulting in attenuated binding of the Fc domain of the antibody to a S. aureus antigen. In some embodiments, amino acid residue 436 (i.e., EU index numbering) from the heavy chain constant region is substituted with Phe, resulting in attenuated binding of the Fc domain of the antibody to a S. aureus antigen. In some embodiments, both amino acid residues 435 and 436 from the heavy chain constant region are substituted with Arg and Phe, respectively, resulting in attenuated binding of the Fc domain of the antibody to a S. aureus antigen. Disclosed herein are antibodies to S. aureus antigens having attenuated Fc binding to Protein A and/or SpsQ. In some aspects, the antibodies comprise an hIgG1 heavy chain of SEQ ID NO: 58, having H318R and Y319F mutations described herein.

In a speciated antibody or antigen-binding fragment provided herein, mutations to the Fc region can be made which attenuate Protein A (or homologous protein) binding to the Fc region of that speciated antibody.

Anti-Protein a Antibodies and Antigen-Binding Fragments Thereof

Protein A is a 42-kDa protein that exists in both secreted and membrane-associated forms, possesses two distinct Ig-binding activities: each domain can bind Fcγ, the constant region of IgG involved in effector functions, and Fab, the Ig fragment responsible for antigen recognition. Protein A is covalently anchored in the staphylococcal cell wall through its carboxyl terminal end. The protein is comprised of five repeated domains (E, D, A, B, C) linked to the cell surface by region Xr, and each domain can bind with high affinity to the Fc region of immunoglobulin G and to the Fab region of immunoglobulin of the VH3 subclass. The interaction with IgG Fc hinders effector function. In addition, antibodies bound to Protein A through the Fc region cannot stimulate complement fixation by the classical pathway.

Provided herein are anti-Protein A antibodies having attenuated Fc binding. Such antibodies have HCVR amino acid sequences and LCVR amino acid sequences as shown in Tables 1 and 15, and also can comprise an IgG1 heavy chain amino acid sequence of SEQ ID NO: 58. This IgG1 sequence comprises H435R and Y436F mutations in the hIgG1 Fc (EU index numbering; equivalent to H318R and Y319F of SEQ ID NO: 58).

According to one aspect of the present disclosure, anti-Protein A antibodies are listed in Tables 1, 2, 15, and 16 herein. Tables 1 and 15 set forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of the exemplary anti-Protein A antibody from which the antibodies of the present disclosure may be derived. Tables 2 and 16 set forth the nucleic acid sequence identifiers of the HCVRs, LCVRs, HCDR1, HCDR2 HCDR3, LCDR1, LCDR2 and LCDR3 of the exemplary anti-Protein A antibody.

The present invention provides antibodies or antigen-binding fragments thereof that specifically bind Protein A, comprising an HCVR comprising an amino acid sequence selected from the group consisting of SEQ ID NOs: 18, 60, and 80, or a substantially similar sequence thereof having at least 90%, at least 95%, at least 98% or at least 99% sequence identity thereto.

The present invention also provides antibodies or antigen-binding fragments thereof that specifically bind Protein A, comprising an LCVR comprising an amino acid sequence selected from the group consisting of SEQ ID NOs: 26, 68, and 88, or a substantially similar sequence thereof having at least 90%, at least 95%, at least 98% or at least 99% sequence identity thereto.

Provided herein are antibodies or antigen-binding fragments thereof that specifically bind Protein A, comprising an HCVR and an LCVR amino acid sequence pair (HCVR/LCVR) comprising an anti-Protein A HCVR amino acid sequence listed in Table 1 or Table 15 and an anti-Protein A LCVR amino acid sequence listed in Table 1 or Table 15. According to certain embodiments, the present invention provides antibodies, or antigen-binding fragments thereof, comprising an HCVR/LCVR amino acid sequence pair contained within the exemplary anti-Protein A antibody listed in Table 1 or Table 15. In certain embodiments, the HCVR/LCVR amino acid sequence pair is selected from the group consisting of SEQ ID NOs: 18/26, 60/68, and 80/88.

The present invention also provides antibodies or antigen-binding fragments thereof that specifically bind Protein A, comprising a set of six CDRs (i.e., HCDR1-HCDR2-HCDR3-LCDR1-LCDR2-LCDR3) contained within any of the exemplary anti-Protein A antibodies listed in Tables 1 and 15. In certain embodiments, the HCDR1-HCDR2-HCDR3-LCDR1-LCDR2-LCDR3 amino acid sequences set comprises SEQ ID NOs: 20-22-24-28-30-32, 62-64-66-70-72-74, or 82-84-86-90-72-93.

In a related embodiment, the present invention provides antibodies, or antigen-binding fragments thereof that specifically bind Protein A, comprising a set of six CDRs (i.e., HCDR1-HCDR2-HCDR3-LCDR1-LCDR2-LCDR3) contained within an HCVR/LCVR amino acid sequence pair as defined by the exemplary anti-Protein A antibodies listed in Tables 1 and 15. For example, the present invention includes antibodies or antigen-binding fragments thereof that specifically bind Protein A, comprising the HCDR1-HCDR2-HCDR3-LCDR1-LCDR2-LCDR3 amino acid sequences set contained within an HCVR/LCVR amino acid sequence pair selected from the group consisting of: SEQ ID NOs: 18/26, 60/68, and 80/88.

In some aspects, the anti-Protein A antibody comprises a heavy chain amino acid sequence of SEQ ID NO: 76, or a substantially similar sequence thereof having at least 90%, at least 95%, at least 98% or at least 99% sequence identity thereof. In some aspects, the anti-Protein A antibody comprises a light chain amino acid sequence of SEQ ID NO: 78, or a substantially similar sequence thereof having at least 90%, at least 95%, at least 98% or at least 99% sequence identity thereof.

In some aspects, the anti-Protein A antibody comprises a heavy chain amino acid sequence of SEQ ID NO: 95, or a substantially similar sequence thereof having at least 90%, at least 95%, at least 98% or at least 99% sequence identity thereof. In some aspects, the anti-Protein A antibody comprises a light chain amino acid sequence of SEQ ID NO: 97, or a substantially similar sequence thereof having at least 90%, at least 95%, at least 98% or at least 99% sequence identity thereof.

Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., J. Mol. Biol. 273:927-948 (1997); and Martin et al., Proc. Natl. Acad. Sci. USA 86:9268-9272 (1989). Public databases are also available for identifying CDR sequences within an antibody.

Provided herein are nucleic acid molecules encoding anti-Protein A antibodies or portions thereof. For example, the present invention provides nucleic acid molecules encoding the anti-Protein A HCVR amino acid sequences and anti-Protein A LCVR amino acid sequences listed in Tables 1 and 15; in certain embodiments the nucleic acid molecule comprises a polynucleotide sequence selected from the anti-Protein A HCVR nucleic acid sequences and anti-Protein A LCVR nucleic acid sequences listed in Tables 2 and 16, or a substantially similar sequence thereof having at least 90%, at least 95%, at least 98% or at least 99% sequence identity thereto.

The present invention also provides nucleic acid molecules encoding any of the anti-Protein A CDR amino acid sequences listed in Tables 1 and 15; in certain embodiments the nucleic acid molecule comprises a polynucleotide sequence selected from any of the anti-Protein A CDR nucleic acid sequences listed in Tables 2 and 16, or a substantially similar sequence thereof having at least 90%, at least 95%, at least 98% or at least 99% sequence identity thereto.

Also provided are nucleic acid molecules encoding an HCVR, wherein the HCVR comprises a set of three CDRs (i.e., HCDR1-HCDR2-HCDR3), wherein the HCDR1-HCDR2-HCDR3 amino acid sequence set is as defined by the exemplary anti-Protein A antibodies listed in Tables 1 and 15.

Also provided are nucleic acid molecules encoding an LCVR, wherein the LCVR comprises a set of three CDRs (i.e., LCDR1-LCDR2-LCDR3), wherein the LCDR1-LCDR2-LCDR3 amino acid sequence set is as defined by the exemplary anti-Protein A antibodies listed in Tables 1 and 15.

Also provided are recombinant expression vectors capable of expressing a polypeptide comprising a heavy or light chain variable region of an anti-Protein A antibody. For example, the present disclosure includes recombinant expression vectors comprising any of the nucleic acid molecules mentioned above, i.e., nucleic acid molecules encoding any of the HCVR, LCVR, and/or CDR sequences as set forth in Tables 1 and 15. Also included within the scope of the present invention are host cells into which such vectors have been introduced, as well as methods of producing the antibodies or portions thereof by culturing the host cells under conditions permitting production of the antibodies or antibody fragments, and recovering the antibodies and antibody fragments so produced.

The present disclosure includes antibodies to Protein A having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

Anti-IsdA Antibodies and Antigen-Binding Fragments Thereof

Iron-regulated surface determinant Protein A (IsdA) is a *S. aureus* protein involved in heme uptake as a source of iron for the bacterium. The IsdA protein is also involved in *S. aureus* adhesion, for example, to human epithelial cells. Overexpression of IsdA enhances *S. aureus* growth and protects against various bactericidal efforts by the host immune system.

Provided herein are anti-IsdA antibodies having attenuated Fc binding to Protein A and/or SpsQ. Such antibodies have HCVR amino acid sequences and LCVR amino acid sequences as shown in Table 1 and Table 25, and also can comprise an IgG1 heavy chain amino acid sequence of SEQ ID NO: 58. This IgG1 sequence comprises H435R and Y436F mutations in the hIgG1 Fc (EU index numbering; equivalent to H318R and Y319F of SEQ ID NO: 58).

According to one aspect of the present disclosure, anti-IsdA antibodies are listed in Tables 1, 2, 25, and 26 herein. Tables 1 and 25 set forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of exemplary IsdA antibodies from which the antibodies of the present disclosure may be derived. Tables 2 and 26 set forth the nucleic acid sequence identifiers of the HCVRs, LCVRs, HCDR1, HCDR2 HCDR3, LCDR1, LCDR2 and LCDR3 of exemplary anti-IsdA antibodies.

The present invention provides antibodies or antigen-binding fragments thereof that specifically bind IsdA, comprising an HCVR comprising an amino acid sequence selected from the group consisting of SEQ ID NOs: 2 and 99, or a substantially similar sequence thereof having at least 90%, at least 95%, at least 98% or at least 99% sequence identity thereto.

The present invention also provides antibodies or antigen-binding fragments thereof that specifically bind IsdA, comprising an LCVR comprising an amino acid sequence selected from the group consisting of SEQ ID NOs: 10 and 107, or a substantially similar sequence thereof having at least 90%, at least 95%, at least 98% or at least 99% sequence identity thereto.

Provided herein are antibodies or antigen-binding fragments thereof that specifically bind IsdA, comprising an HCVR and an LCVR amino acid sequence pair (HCVR/LCVR) comprising an HCVR amino acid sequence listed in Table 1 or Table 25 and an LCVR amino acid sequence listed in Table 1 or Table 25. According to certain embodiments, the present invention provides antibodies, or antigen-binding fragments thereof, comprising an HCVR/LCVR amino acid sequence pair contained within the exemplary anti-IsdA antibody listed in Table 1 or an HCVR/LCVR amino acid sequence pair contained within the exemplary anti-IsdA antibody listed in Table 25. In certain embodiments, the HCVR/LCVR amino acid sequence pair is SEQ ID NOs: 2/10. In certain embodiments, the HCVR/LCVR amino acid sequence pair is SEQ ID NOs: 99/107.

The present invention also provides antibodies or antigen-binding fragments thereof that specifically bind IsdA, comprising a set of six CDRs (i.e., HCDR1-HCDR2-HCDR3-LCDR1-LCDR2-LCDR3) contained within any of the exemplary anti-IsdA antibodies listed in Table 1 or Table 25. In certain embodiments, the HCDR1-HCDR2-HCDR3-LCDR1-LCDR2-LCDR3 amino acid sequences set comprises SEQ ID NOs: 4-6-8-12-14-16. In certain embodiments, the HCDR1-HCDR2-HCDR3-LCDR1-LCDR2-LCDR3 amino acid sequences set comprises SEQ ID NOs: 101-103-105-109-111-113.

In a related embodiment, the present invention provides antibodies, or antigen-binding fragments thereof that specifically bind IsdA, comprising a set of six CDRs (i.e., HCDR1-HCDR2-HCDR3-LCDR1-LCDR2-LCDR3) contained within an HCVR/LCVR amino acid sequence pair as defined by an exemplary anti-IsdA antibody listed in Table 1 or Table 25. For example, the present invention includes antibodies or antigen-binding fragments thereof that specifically bind IsdA, comprising the HCDR1-HCDR2-HCDR3-LCDR1-LCDR2-LCDR3 amino acid sequences set contained within an HCVR/LCVR amino acid sequence pair of SEQ ID NOs: 2/10. Likewise, the present invention includes antibodies or antigen-binding fragments thereof that specifically bind IsdA, comprising the HCDR1-HCDR2-HCDR3-LCDR1-LCDR2-LCDR3 amino acid sequences set contained within an HCVR/LCVR amino acid sequence pair of SEQ ID NOs: 99/107.

In some aspects, the anti-IsdA antibody comprises a heavy chain amino acid sequence of SEQ ID NO: 115. In some aspects, the anti-IsdA antibody comprises a light chain amino acid sequence of SEQ ID NO: 117. See Table 27.

Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

Provided herein are nucleic acid molecules encoding anti-IsdA antibodies or portions thereof. For example, the present invention provides nucleic acid molecules encoding the anti-IsdA HCVR amino acid sequences and anti-IsdA LCVR amino acid sequences listed in Table 1 and Table 25; in certain embodiments the nucleic acid molecule comprises a polynucleotide sequence selected from the anti-IsdA HCVR nucleic acid sequences and anti-IsdA LCVR nucleic acid sequences listed in Table 2 or Table 26, or a substantially similar sequence thereof having at least 90%, at least 95%, at least 98% or at least 99% sequence identity thereto.

The present invention also provides nucleic acid molecules encoding any of the anti-IsdA CDR amino acid sequences listed in Table 1 or Table 25; in certain embodiments the nucleic acid molecule comprises a polynucleotide sequence selected from any of the anti-IsdA CDR nucleic acid sequences listed in Table 2 or Table 26, or a substantially similar sequence thereof having at least 90%, at least 95%, at least 98% or at least 99% sequence identity thereto.

Also provided are nucleic acid molecules encoding an HCVR, wherein the HCVR comprises a set of three CDRs (i.e., HCDR1-HCDR2-HCDR3), wherein the HCDR1-HCDR2-HCDR3 amino acid sequence set is as defined by an exemplary anti-IsdA antibody listed in Table 1 or Table 25.

Also provided are nucleic acid molecules encoding an LCVR, wherein the LCVR comprises a set of three CDRs (i.e., LCDR1-LCDR2-LCDR3), wherein the LCDR1-LCDR2-LCDR3 amino acid sequence set is as defined by an exemplary anti-IsdA antibody listed in Table 1 or Table 25.

Also provide are recombinant expression vectors capable of expressing a polypeptide comprising a heavy or light chain variable region of an anti-IsdA antibody. For example, the present disclosure includes recombinant expression vectors comprising any of the nucleic acid molecules mentioned above, i.e., nucleic acid molecules encoding any of the HCVR, LCVR, and/or CDR sequences as set forth in Tables 1 and 25. Also included within the scope of the present invention are host cells into which such vectors have been introduced, as well as methods of producing the antibodies or portions thereof by culturing the host cells under conditions permitting production of the antibodies or antibody fragments, and recovering the antibodies and antibody fragments so produced.

The present disclosure includes antibodies to IsdA having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

Anti-IsdB Antibodies and Antigen-Binding Fragments Thereof

*S. aureus* capture hemoglobin on the bacterial surface using IsdB, another iron-regulated surface determinant protein (Isd). Inactivation of IsdB decreases hemoglobin binding to the bacterial cell wall and impairs the ability of *S. aureus* to utilize hemoglobin as an iron source.

Provided herein are anti-IsdB antibodies having attenuated Fc binding to Protein A and/or SpsQ. Such antibodies have HCVR amino acid sequences and LCVR amino acid sequences as shown in Tables 1 and 25, and can further comprise an IgG1 heavy chain amino acid sequence of SEQ ID NO: 58. This IgG1 sequence comprises H435R and Y436F mutations in the hIgG1 Fc (EU index numbering;

equivalent to H318R and Y319F of SEQ ID NO: 58). In some aspects, the anti-IsdB antibody comprises a heavy chain amino acid sequence of SEQ ID NO: 54. In some aspects, the anti-IsdB antibody comprises a light chain amino acid sequence of SEQ ID NO: 52. See Table 3. In some aspects, the anti-IsdB antibody comprises a heavy chain amino acid sequence of SEQ ID NO: 135. In some aspects, the anti-IsdB antibody comprises a light chain amino acid sequence of SEQ ID NO: 137. See Table 27.

According to one aspect of the present disclosure, anti-IsdB antibodies according to this aspect of the invention are listed in Tables 1, 2, 25, and 26 herein. Table 1 sets forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of the exemplary IsdB antibody from which the antibodies of the present disclosure may be derived. Table 2 sets forth the nucleic acid sequence identifiers of the HCVRs, LCVRs, HCDR1, HCDR2 HCDR3, LCDR1, LCDR2 and LCDR3 of the exemplary anti-IsdB antibody.

The present invention provides antibodies or antigen-binding fragments thereof that specifically bind IsdB, comprising an HCVR comprising an amino acid sequence of SEQ ID NO: 34 or SEQ ID NO: 119, or a substantially similar sequence thereof having at least 90%, at least 95%, at least 98% or at least 99% sequence identity thereto.

The present invention also provides antibodies or antigen-binding fragments thereof that specifically bind IsdB, comprising an LCVR comprising an amino acid sequence of SEQ ID NO: 42 or SEQ ID NO: 127, or a substantially similar sequence thereof having at least 90%, at least 95%, at least 98% or at least 99% sequence identity thereto.

The present invention also provides antibodies or antigen-binding fragments thereof that specifically bind IsdB, comprising an HCVR and an LCVR amino acid sequence pair (HCVR/LCVR) comprising the HCVR amino acid sequences listed in Table 1 paired with LCVR amino acid sequences listed in Table 1. According to certain embodiments, the present invention provides antibodies, or antigen-binding fragments thereof, comprising an HCVR/LCVR amino acid sequence pair contained within the exemplary anti-IsdB antibody listed in Table 1. In certain embodiments, the HCVR/LCVR amino acid sequence pair is SEQ ID NOs: 34/42.

The present invention also provides antibodies or antigen-binding fragments thereof that specifically bind IsdB, comprising a set of six CDRs (i.e., HCDR1-HCDR2-HCDR3-LCDR1-LCDR2-LCDR3) contained within any of the exemplary anti-IsdB antibody listed in Table 1. In certain embodiments, the HCDR1-HCDR2-HCDR3-LCDR1-LCDR2-LCDR3 amino acid sequences set comprises SEQ ID NOs: 36-38-40-44-46-48.

In a related embodiment, the present invention provides antibodies, or antigen-binding fragments thereof that specifically bind IsdB, comprising a set of six CDRs (i.e., HCDR1-HCDR2-HCDR3-LCDR1-LCDR2-LCDR3) contained within an HCVR/LCVR amino acid sequence pair as defined by the exemplary anti-IsdB antibody listed in Table 1. For example, the present invention includes antibodies or antigen-binding fragments thereof that specifically bind IsdB, comprising the HCDR1-HCDR2-HCDR3-LCDR1-LCDR2-LCDR3 amino acid sequences set contained within an HCVR/LCVR amino acid sequence pair of: SEQ ID NOs: 34/42.

The present invention also provides antibodies or antigen-binding fragments thereof that specifically bind IsdB, comprising an HCVR and an LCVR amino acid sequence pair (HCVR/LCVR) comprising the HCVR amino acid sequences listed in Table 25 paired with LCVR amino acid sequences listed in Table 25. According to certain embodiments, the present invention provides antibodies, or antigen-binding fragments thereof, comprising an HCVR/LCVR amino acid sequence pair contained within the exemplary anti-IsdB antibody listed in Table 25. In certain embodiments, the HCVR/LCVR amino acid sequence pair is SEQ ID NOs: 119/127.

The present invention also provides antibodies or antigen-binding fragments thereof that specifically bind IsdB, comprising a set of six CDRs (i.e., HCDR1-HCDR2-HCDR3-LCDR1-LCDR2-LCDR3) contained within any of the exemplary anti-IsdB antibody listed in Table 25. In certain embodiments, the HCDR1-HCDR2-HCDR3-LCDR1-LCDR2-LCDR3 amino acid sequences set comprises SEQ ID NOs: 121-123-125-129-131-133.

In a related embodiment, the present invention provides antibodies, or antigen-binding fragments thereof that specifically bind IsdB, comprising a set of six CDRs (i.e., HCDR1-HCDR2-HCDR3-LCDR1-LCDR2-LCDR3) contained within an HCVR/LCVR amino acid sequence pair as defined by the exemplary anti-IsdB antibody listed in Table 25. For example, the present invention includes antibodies or antigen-binding fragments thereof that specifically bind IsdB, comprising the HCDR1-HCDR2-HCDR3-LCDR1-LCDR2-LCDR3 amino acid sequences set contained within an HCVR/LCVR amino acid sequence pair of: SEQ ID NOs: 119/127.

Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

Provided herein are nucleic acid molecules encoding anti-IsdB antibodies or portions thereof. For example, the present invention provides nucleic acid molecules encoding the anti-IsdB HCVR amino acid sequences and anti-IsdB LCVR amino acid sequences listed in Tables 1 and 25; in certain embodiments the nucleic acid molecule comprises a polynucleotide sequence selected from the anti-IsdB HCVR nucleic acid sequences and anti-IsdB LCVR nucleic acid sequences listed in Table 2 and Table 26, or a substantially similar sequence thereof having at least 90%, at least 95%, at least 98% or at least 99% sequence identity thereto.

The present invention also provides nucleic acid molecules encoding any of the anti-IsdB CDR amino acid sequences listed in Tables 1 and 25; in certain embodiments the nucleic acid molecule comprises a polynucleotide sequence selected from any of the anti-IsdB CDR nucleic acid sequences listed in Tables 2 and 26, or a substantially similar sequence thereof having at least 90%, at least 95%, at least 98% or at least 99% sequence identity thereto.

Also provided are nucleic acid molecules encoding an HCVR, wherein the HCVR comprises a set of three CDRs (i.e., HCDR1-HCDR2-HCDR3), wherein the HCDR1-HCDR2-HCDR3 amino acid sequence set is as defined by the exemplary anti-IsdB antibody listed in Table 1 or the exemplary anti-IsdB antibody listed in Table 25.

Also provided are nucleic acid molecules encoding an LCVR, wherein the LCVR comprises a set of three CDRs (i.e., LCDR1-LCDR2-LCDR3), wherein the LCDR1-LCDR2-LCDR3 amino acid sequence set is as defined by the exemplary anti-IsdB antibody listed in Table 1 or the exemplary anti-IsdB antibody listed in Table 25.

Also provide are recombinant expression vectors capable of expressing a polypeptide comprising a heavy or light chain variable region of an anti-IsdB antibody. For example, the present disclosure includes recombinant expression vectors comprising any of the nucleic acid molecules mentioned above, i.e., nucleic acid molecules encoding any of the HCVR, LCVR, and/or CDR sequences as set forth in Table 1 and Table 25. Also included within the scope of the present invention are host cells into which such vectors have been introduced, as well as methods of producing the antibodies or portions thereof by culturing the host cells under conditions permitting production of the antibodies or antibody fragments, and recovering the antibodies and antibody fragments so produced.

The present disclosure includes antibodies to IsdB having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

Additional Fc Variants

In addition to the */* variants described above, certain additional Fc variants are contemplated herein. According to certain embodiments, speciated antibodies to a given staphylococcal antigen will be modified in the Fc region of the antibody to attenuate binding by Protein A or homologous protein appropriate for the respective animal species.

According to certain embodiments, antibodies to S. aureus antigens are provided comprising an Fc domain comprising one or more mutations which enhance or diminish antibody binding to the FcRn receptor, e.g., at acidic pH as compared to neutral pH. For example, the present invention includes antibodies to S. aureus antigens comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

For example, antibodies to S. aureus antigens comprise an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the antibody variable domains disclosed herein, are contemplated within the scope of the present disclosure.

The antibodies to S. aureus antigens as disclosed herein may comprise a modified Fc domain having altered effector function, for example, increased or reduced effector function. As used herein, a "modified Fc domain having altered effector function" means any Fc portion of an immunoglobulin that has been modified, mutated, truncated, etc., relative to a wild-type, naturally occurring Fc domain such that a molecule comprising the modified Fc exhibits an increase or reduction in the severity or extent of at least one effect selected from the group consisting of cell killing (e.g., ADCC and/or CDC), complement activation, phagocytosis and opsonization, relative to a comparator molecule comprising the wild-type, naturally occurring version of the Fc portion. In certain embodiments, a "modified Fc domain having altered effector function" is an Fc domain with reduced or attenuated binding to an Fc receptor (e.g., FcγR). Exemplary modified Fc domains are described in US 2006/0024298, incorporated by reference herein in its entirety. In some embodiments, the modification is G236A.

In certain embodiments, the modified Fc domain is a variant IgG1 Fc or a variant IgG4 Fc comprising a substitution in the hinge region. For example, a modified Fc for use in the context of the present invention may comprise a variant IgG1 Fc wherein at least one amino acid of the IgG1 Fc hinge region is replaced with the corresponding amino acid from the IgG2 Fc hinge region. Alternatively, a modified Fc for use in the context of the present invention may comprise a variant IgG4 Fc wherein at least one amino acid of the IgG4 Fc hinge region is replaced with the corresponding amino acid from the IgG2 Fc hinge region. Non-limiting, exemplary modified Fc regions that can be used in the context of the present invention are set forth in US Patent Application Publication No. 2014/0243504, the disclosure of which is hereby incorporated by reference in its entirety, as well as any functionally equivalent variants of the modified Fc regions set forth therein.

Other modified Fc domains and Fc modifications that can be used in the context of the present invention include any of the modifications as set forth in US 2014/0171623; U.S. Pat. No. 8,697,396; US 2014/0134162; WO 2014/043361, the disclosures of which are hereby incorporated by reference in their entireties. Methods of constructing antibodies or other antigen-binding fusion proteins comprising a modified Fc domain as described herein are known in the art.

Preparation of Human Antibodies

Methods for generating human antibodies in transgenic mice are known in the art. Any such known methods can be used in the context of the present invention to make human antibodies that specifically bind to S. aureus antigens. An immunogen comprising any S. aureus antigen such as Protein A, IsdA, and IsdB can be used to generate antibodies. In certain embodiments, the antibodies of the invention are obtained from mice immunized with a S. aureus antigen or with DNA encoding the antigen or fragment thereof. Alternatively, the antigen or a fragment thereof may be produced using standard biochemical techniques and modified and used as immunogen. In one embodiment, the immunogen is a recombinantly produced Protein A, IsdA, or IsdB or fragment thereof. In certain embodiments of the invention, the immunogen may be a commercially available antigen. In certain embodiments, one or more booster injections may be administered. In certain embodiments, the booster injections may comprise one or more commercially available antigens. In certain embodiments, the immunogen may be a recombinant antigen expressed in E. coli or in any other eukaryotic or mammalian cells such as Chinese hamster ovary (CHO) cells.

Using VELOCIMMUNE® technology (see, for example, U.S. Pat. No. 6,596,541, Regeneron Pharmaceuticals, VELOCIMMUNE®) or any other known method for generating monoclonal antibodies, high affinity chimeric antibodies to S. aureus antigens are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody of the invention, for example, the modified IgG1*/* described herein. While the constant region selected may vary according to specific use, high affinity antigen-binding and target specificity characteristics reside in the variable region.

Bioequivalents

The antibodies to Staphylococcal antigens and antibody fragments described herein encompass proteins having amino acid sequences that vary from those of the described antibodies, but that retain the ability to the particular antigen with attenuated Fc binding. Such variant antibodies and antibody fragments comprise one or more additions, deletions, or substitutions of amino acids when compared to parent sequence, but exhibit biological activity that is essentially equivalent to that of the described antibodies. Likewise, the antibody-encoding DNA sequences of the present invention encompass sequences that comprise one or more additions, deletions, or substitutions of nucleotides when compared to the disclosed sequence, but that encode an antibody or antibody fragment that is essentially bioequivalent to an antibody or antibody fragment of the invention.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single dose or multiple doses. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, or potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of the antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include antibody variants comprising amino acid changes, which modify the glycosylation characteristics of the antibodies, e.g., mutations that eliminate or remove glycosylation.

Epitope Mapping, Binding Domains, and Related Technologies

The present invention includes antibodies to staphylococcal antigens that interact with one or more amino acids found within the specific staphylococcal protein to which the antibody was made, for example, to S. aureus antigens such as Protein A, IsdA, or IsdB. The epitope to which the antibodies bind may consist of a single contiguous sequence of 3 or more (e.g., 3, 4, 5, 6, 7, 8, 9, 10, 11, 12, 13, 14, 15, 16, 17, 18, 19, 20 or more) amino acids located within the antigen (e.g. a linear epitope in a domain). Alternatively, the epitope may consist of a plurality of non-contiguous amino acids (or amino acid sequences) located within the antigen (e.g. a conformational epitope).

Various techniques known to persons of ordinary skill in the art can be used to determine whether an antibody "interacts with one or more amino acids" within a polypeptide or protein. Exemplary techniques include, for example, routine cross-blocking assays, such as that described in Antibodies, Harlow and Lane (Cold Spring Harbor Press, Cold Spring Harbor, NY). Other methods include alanine scanning mutational analysis, peptide blot analysis (Reineke (2004) Methods Mol. Biol. 248: 443-63), peptide cleavage analysis crystallographic studies and NMR analysis. In addition, methods such as epitope excision, epitope extraction and chemical modification of antigens can be employed (Tomer (2000) Prot. Sci. 9: 487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues that correspond to the specific amino acids with which the antibody interacts. See, e.g., Ehring (1999) Analytical Biochemistry 267: 252-259; Engen and Smith (2001) Anal. Chem. 73: 256A-265A.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (see US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce monoclonal antibodies having the desired characteristics. MAP may be used to sort the antibodies of the invention into groups of antibodies binding different epitopes.

In certain embodiments, the S. aureus antibodies or antigen-binding fragments thereof bind an epitope within any one or more of the regions exemplified in the specific S. aureus antigen, either in natural form, or recombinantly produced, or to a fragment thereof.

The present disclosure includes antibodies to a S. aureus antigen that bind to the same epitope, or a portion of the epitope of that specific antigen. Likewise, the present disclosure also includes antibodies that compete for binding to the S. aureus antigen or a fragment thereof with any of the specific exemplary antibodies described herein.

One can easily determine whether an antibody binds to the same epitope as, or competes for binding with, a reference antibody by using routine methods known in the art. For example, to determine if a test antibody binds to the same epitope as a reference anti-Protein A antibody of the invention, the reference antibody is allowed to bind to Protein A or Protein A peptide under saturating conditions. Next, the ability of a test antibody to bind to Protein A is assessed. If the test antibody is able to bind to Protein A following saturation binding with the reference anti-Protein A antibody, it can be concluded that the test antibody binds to a different epitope than the reference Protein A antibody. On the other hand, if the test antibody is not able to bind to Protein A following saturation binding with the reference anti-Protein A antibody, then the test antibody may bind to the same epitope as the epitope bound by the reference anti-Protein A antibody described herein.

To determine if an anti-Protein A antibody competes for binding with a reference Protein A antibody, the above-described binding methodology is performed in two orientations: In a first orientation, the reference antibody is allowed to bind to Protein A under saturating conditions followed by assessment of binding of the test antibody to Protein A. In a second orientation, the test antibody is allowed to bind to Protein A under saturating conditions followed by assessment of binding of the reference antibody to Protein A. If, in both orientations, only the first (saturating) antibody is capable of binding to Protein A, then it is concluded that the test antibody and the reference antibody compete for binding to Protein A. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Multi-Specific Antibodies

The antibodies of the present invention may be monospecific, bi-specific, or multi-specific. Multi-specific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244.

Any of the multi-specific antigen-binding molecules of the invention, or variants thereof, may be constructed using standard molecular biological techniques (e.g., recombinant DNA and protein expression technology), as will be known to a person of ordinary skill in the art.

In some embodiments, antibodies are generated in a bi-specific format (a "bi-specific") in which variable regions binding to different S. aureus antigens are linked together to confer dual-domain specificity within a single binding molecule. Appropriately designed bi-specifics may enhance overall inhibitory efficacy through increasing both specificity and binding avidity. Variable regions with specificity for individual domains, (e.g., segments of the N-terminal domain), or that can bind to different regions within one domain, are paired on a structural scaffold that allows each region to bind simultaneously to the separate epitopes, or to different regions within one domain. In one example for a bi-specific, heavy chain variable regions ($V_H$) from a binder with specificity for one domain are recombined with light chain variable regions ($V_L$) from a series of binders with specificity for a second domain to identify non-cognate $V_L$ partners that can be paired with an original $V_H$ without disrupting the original specificity for that $V_H$. In this way, a single $V_L$ segment (e.g., $V_L1$) can be combined with two different $V_H$ domains (e.g., $V_H1$ and $V_H2$) to generate a bi-specific comprised of two binding "arms" ($V_H1$-$V_L1$ and $V_H2$-$V_L1$). Use of a single $V_L$ segment reduces the complexity of the system and thereby simplifies and increases efficiency in cloning, expression, and purification processes used to generate the bi-specific (See, for example, U.S. Ser. No. 13/022,759 and US2010/0331527).

Alternatively, antibodies that bind more than one domain and a second target, such as, but not limited to, for example, a second different antibody to a S. aureus antigen, may be prepared in a bi-specific format using techniques described herein, or other techniques known to those skilled in the art. Antibody variable regions binding to distinct regions may be linked together with variable regions that bind to relevant sites on, for example, a S. aureus antigen, to confer dual-antigen specificity within a single binding molecule. Appropriately designed bi-specifics of this nature serve a dual function. Variable regions with specificity for the extracellular domain are combined with a variable region with specificity for outside the extracellular domain and are paired on a structural scaffold that allows each variable region to bind to the separate antigens.

An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bi-specific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Other exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$^2$ bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

Therapeutic Administration and Formulations

The invention provides therapeutic compositions comprising the staphylococcal antibodies to disclosed herein or antigen-binding fragments thereof. Therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, PA These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody may vary depending upon the age and the size of a subject to be administered, target disease, conditions, route of administration, and the like. When an antibody of the present invention is used for treating a disease or disorder in an adult patient, or for preventing such a disease, it is advantageous to administer the antibody of the present invention normally at a single dose of about 0.1 to about 60 mg/kg body weight, more preferably about 5 to about 60, about 10 to about 50, or about 20 to about 50 mg/kg body weight. Depending on the severity of the condition, the frequency and the duration of the treatment can be adjusted. In certain embodiments, the antibody or antigen-binding fragment thereof of the invention can be administered as an initial dose of at least about 0.1 mg to about 800 mg, about 1 to about 500 mg, about 5 to about 300 mg, or about 10 to about 200 mg, to about 100 mg, or to about 50 mg. In certain embodiments, the initial dose may be followed by administration of a second or a plurality of subsequent doses of the antibody or antigen-binding fragment thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, transdermal, intramuscular, intraperitoneal, intravenous, subcutaneous, intranasal, epidural and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. The pharmaceutical composition can be also delivered in a vesicle, in particular a liposome (see, for example, Langer (1990) Science 249: 1527-1533).

The use of nanoparticles to deliver the antibodies of the present invention is also contemplated herein. Antibody-conjugated nanoparticles may be used both for therapeutic and diagnostic applications. Antibody-conjugated nanoparticles and methods of preparation and use are described in detail by Arruebo, M., et al. 2009 ("Antibody-conjugated nanoparticles for biomedical applications" in J. Nanomat. Volume 2009, Article ID 439389, 24 pages, doi: 10.1155/2009/439389), incorporated herein by reference. Nanoparticles may be developed and conjugated to antibodies contained in pharmaceutical compositions to target infected cells. Nanoparticles for drug delivery have also been described in, for example, U.S. Pat. No. 8,257,740, or U.S. Pat. No. 8,246,995, each incorporated herein in its entirety.

An adeno-associated virus vector (AAV) can be used to deliver the antibodies provided herein. See WO/2018/226861, incorporated by reference herein. In one embodiment, the AAV contains a polynucleotide encoding the therapeutic antibody or antigen-binding fragment thereof. The polynucleotide subsequently integrates into a genomic locus of the subject's cells, e.g. the udder of a cow being treated for mastitis, from which the polynucleotide is transcribed and the antibody is produced. In one embodiment, the genomic locus is a safe harbor locus, which enables high expression of the antibody, while not interfering with the expression of essential genes or promoting the expression of oncogenes or other deleterious genes. In one embodiment, the genomic locus is an adeno-associated virus site.

In one aspect, the invention provides a method of treating a patient (cow, etc.) with a staphylococcal infection by administering to the patient a vector containing a polynucleotide encoding the antibody intended for treatment.

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracutaneous, intracranial, intraperitoneal and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, IN), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition of the present invention include, but certainly are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, CA), the PENLET™ (Haselmeier, Stuttgart, Germany), the EPIPEN (Dey, L. P.) and the HUMIRA™ Pen (Abbott Labs, Abbott Park, IL), to name only a few.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the antibody contained is generally about 5 to about 500 mg per dosage form in a unit dose; especially in the form of injection, it is preferred that the antibody is contained in about 5 to about 100 mg and in about 10 to about 250 mg for the other dosage forms.

Therapeutic Uses of the Antibodies

The antibodies of the present invention are useful for the treatment, and/or prevention of a disease or disorder or condition associated with staphylococcal infection, for example, a S. aureus infection or S. pseudintermedius infection and/or for ameliorating at least one symptom associated with such disease, disorder or condition. Such disease, disorder or condition can be cellulitis, bacteremia, dermonecrosis, eyelid infection, eye infection, neonatal conjunctivitis, osteomyelitis, impetigo, boils, scalded skin syndrome, food poisoning, pneumonia, surgical infection, urinary tract infection, burn infection, meningitis, endocarditis, septicemia, toxic shock syndrome, or septic arthritis. In some aspects, the subject has a prosthetic joint and the antibodies disclosed herein are used for treating and/or preventing S. aureus infection of the tissue surrounding the prosthetic joint. In some aspects, the subject has a catheter and the antibodies disclosed herein are used for treating and/or preventing S. aureus infection of the catheter and/or the tissue surrounding the catheter. In some aspects, the subject has a foreign body implanted, and the antibodies disclosed herein are used for treating and/or preventing S. aureus infection of the foreign body and/or the tissue surrounding the foreign body. In some aspects, the subject has mastitis, and the antibodies disclosed herein are useful for treating mastitis.

In certain embodiments, the antibodies of the invention are useful to treat subjects suffering from acute or chronic infection caused by S. aureus or S. pseudintermedius. In some embodiments, the antibodies of the invention are useful in decreasing bacterial titers or reducing bacterial load in the host or host organs. In one embodiment, an antibody or antigen-binding fragment thereof the invention may be administered at a therapeutic dose to a patient with S. aureus infection or S. pseudintermedius infection.

One or more antibodies of the present invention may be administered to relieve or prevent or decrease the severity of one or more of the symptoms or conditions associated with S. aureus infection or S. pseudintermedius infection. The antibodies may be used to ameliorate or reduce the severity of at least one symptom of S. aureus infection or S. pseudintermedius infection including, but not limited to itching, redness, rash, swelling, nausea, vomiting, diarrhea, dehydration, low blood pressure, fever, confusion, muscle aches, abdominal pain, joint swelling, and joint pain.

It is also contemplated herein to use one or more antibodies provided herein prophylactically for preventing a S. aureus infection or S. pseudintermedius infection. Such subject can be a surgery patient, may have suffered an injury, or is a burn victim.

In a further embodiment of the invention the present antibodies are used for the preparation of a pharmaceutical composition for treating patients suffering from an S. aureus infection or S. pseudintermedius infection. In another embodiment of the invention, the present antibodies are used as adjunct therapy with any other agent or any other therapy known to those skilled in the art useful for treating or ameliorating an S. aureus infection or S. pseudintermedius infection.

Combination Therapies

Combination therapies may include an antibody to a staphylococcal antigen provided herein and any additional therapeutic agent that may be advantageously combined with an antibody of the invention, or with a biologically active fragment of an antibody of the invention. The antibodies of the present invention may be combined synergistically with one or more drugs or agents used to treat a staphylococcal infection.

For example, exemplary agents for treating a bacterial infection may include, e.g., anti-bacterial drug, an anti-inflammatory drug (such as corticosteroids, and non-steroidal anti-inflammatory drugs), a different antibody to S. aureus, a vaccine for S. aureus, or any other palliative therapy to treat S. aureus infection.

Exemplary agents include penicillin, oxacillin, rifampin, flucloxacillin, dicloxacillin, cefazolin, cephalothin, cephalexin, nafcillin, clindamycin, lincomycin, linezolid, daptomycin, erythromycin, vancomycin, gentamicin, doxycycline, and trimethoprim-sulfamethoxazole.

In some embodiments, the antibodies provided herein may be combined with a second therapeutic agent to reduce the bacterial load in a patient with S. aureus infection or S. pseudintermedius infection, or to ameliorate one or more symptoms of the infection.

In certain embodiments, the second therapeutic agent is another different antibody, or antibody cocktail specific for one or more staphylococcal antigens, wherein the different antibody or antibodies within the cocktail may or may not bind to the same antigen as an antibody of the present disclosure. In certain embodiments, the second therapeutic agent is an antibody to a different staphylococcal protein.

As used herein, the term "in combination with" means that additional therapeutically active component(s) may be administered prior to, concurrent with, or after the administration of at least one antibody to a staphylococcal antigen provided herein, or a cocktail comprising one or more of the antibodies the provided herein. The term "in combination with" also includes sequential or concomitant administration of an antibody to, for example, S. aureus, and a second therapeutic agent.

The additional therapeutically active component(s) may be administered to a subject prior to administration of an anti-staphylococcal antibody of the present disclosure. For example, a first component may be deemed to be administered "prior to" a second component if the first component is administered 1 week before, 72 hours before, 60 hours before, 48 hours before, 36 hours before, 24 hours before, 12 hours before, 6 hours before, 5 hours before, 4 hours before, 3 hours before, 2 hours before, 1 hour before, 30 minutes before, 15 minutes before, 10 minutes before, 5 minutes before, or less than 1 minute before administration of the second component. In other embodiments, the additional therapeutically active component(s) may be administered to a subject after administration of an antibody of the present invention. For example, a first component may be deemed to be administered "after" a second component if the first component is administered 1 minute after, 5 minutes after, 10 minutes after, 15 minutes after, 30 minutes after, 1 hour after, 2 hours after, 3 hours after, 4 hours after, 5 hours after, 6 hours after, 12 hours after, 24 hours after, 36 hours after, 48 hours after, 60 hours after, 72 hours after administration of the second component. In yet other embodiments, the additional therapeutically active component(s) may be administered to a subject concurrent with administration of an antibody of the present invention. "Concurrent" administration, for purposes of the present invention, includes, e.g., administration of an anti-staphylococcal antibody, such as an anti-Protein A antibody, an anti-IsdA antibody, or an anti-IsdB antibody, and an additional therapeutically active component to a subject in a single dosage form, or in separate dosage forms administered to the subject within about 30 minutes or less of each other. If administered in separate dosage forms, each dosage form may be administered via the same route (e.g., both the antibody and the additional therapeutically active component may be administered intravenously, etc.); alternatively, each dosage form may be administered via a different route (e.g., the antibody may be administered intravenously, and the additional therapeutically active component may be administered orally). In any event, administering the components in a single dosage from, in separate dosage forms by the same route, or in separate dosage forms by different routes are all considered "concurrent administration," for purposes of the present disclosure. For purposes of the present disclosure, administration of an antibody "prior to", "concurrent with," or "after" (as those terms are defined herein above) administration of an additional therapeutically active component is considered administration of an antibody "in combination with" an additional therapeutically active component.

The present invention includes pharmaceutical compositions in which an anti-*S. aureus* antibody of the present disclosure is co-formulated with one or more of the additional therapeutically active component(s) as described elsewhere herein.

Administration Regimens

According to certain embodiments, a single dose of an antibody provided herein (or a pharmaceutical composition comprising a combination of an antibody to a staphylococcal antigen and any of the additional therapeutically active agents mentioned herein) may be administered to a subject in need thereof. According to certain embodiments of the present invention, multiple doses of an antibody to a staphylococcal antigen (or a pharmaceutical composition comprising a combination of an antibody to a staphylococcal antigen and any of the additional therapeutically active agents mentioned herein) may be administered to a subject over a defined time course. The methods according to this aspect of the invention comprise sequentially administering to a subject multiple doses of an antibody to a staphylococcal antigen of the invention. As used herein, "sequentially administering" means that each dose of antibody to a staphylococcal antigen is administered to the subject at a different point in time, e.g., on different days separated by a predetermined interval (e.g., hours, days, weeks or months). The present invention includes methods which comprise sequentially administering to the patient a single initial dose of an antibody to a staphylococcal antigen, followed by one or more secondary doses of the antibody to a staphylococcal antigen, and optionally followed by one or more tertiary doses of the antibody to a staphylococcal antigen.

The terms "initial dose," "secondary doses," and "tertiary doses," refer to the temporal sequence of administration of the antibody to a *S. aureus* antigen of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of antibody to a staphylococcal antigen, but generally may differ from one another in terms of frequency of administration. In certain embodiments, however, the amount of antibody to a staphylococcal antigen contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments of the present invention, each secondary and/or tertiary dose is administered 1 to 48 hours (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) after the immediately preceding dose. The phrase "the immediately preceding dose," as used herein, means, in a sequence of multiple administrations, the dose of antibody to a staphylococcal antigen, which is administered to a patient prior to the administration of the very next dose in the sequence with no intervening doses.

The methods according to this aspect of the invention may comprise administering to a patient any number of secondary and/or tertiary doses of an antibody to a staphylococcal antigen. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In certain embodiments of the invention, the frequency at which the secondary and/or tertiary doses are administered to a patient can vary over the course of the treatment regimen. The frequency of administration may also be adjusted during the course of treatment by a physician depending on the needs of the individual patient following clinical examination.

Diagnostic Uses of the Antibodies

The antibodies to staphylococcal antigens provided herein may be used to detect and/or measure, for example, *S. aureus* or *S. pseudintermedius*, in a sample, e.g., for diagnostic purposes. Some embodiments contemplate the use of one or more antibodies of the present invention in assays to detect a disease or disorder such as bacterial infection. Exemplary diagnostic assays for *S. aureus* or *S. pseudintermedius* may comprise, e.g., contacting a sample, obtained from a patient, with an antibody to a *S. aureus* antigen of the invention, wherein the antibody to a *S. aureus* or *S. pseudintermedius* antigen is labeled with a detectable label or reporter molecule or used as a capture ligand to selectively isolate *S. aureus* or *S. pseudintermedius* from patient samples. Alternatively, an unlabeled antibody to a *S. aureus* or *S. pseudintermedius* antigen can be used in diagnostic applications in combination with a secondary antibody which is itself detectably labeled. The detectable label or reporter molecule can be a radioisotope, such as 3H, 14C, 32P, 35S, or 125I; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure *S. aureus* or *S. pseudintermedius* in a sample include enzyme-linked immunosorbent assay (ELISA), radioimmunoassay (RIA), and fluorescence-activated cell sorting (FACS).

Samples that can be used in *S. aureus* or *S. pseudintermedius* diagnostic assays according to the present invention include any tissue or fluid sample obtainable from a patient, which contains detectable quantities of either *S. aureus* or *S. pseudintermedius*, or fragments thereof, under normal or pathological conditions. Generally, levels of *S. aureus* or *S. pseudintermedius* in a particular sample obtained from a healthy patient (e.g., a patient not afflicted with a disease associated with *S. aureus* or *S. pseudintermedius* will be measured to initially establish a baseline, or standard, level of *S. aureus* or *S. pseudintermedius*. This baseline level of *S. aureus* or *S. pseudintermedius* can then be compared against the levels of *S. aureus* or *S. pseudintermedius* measured in samples obtained from individuals suspected of having a *S. aureus*-associated condition, or symptoms associated with such condition.

The antibodies specific for *S. aureus* or *S. pseudintermedius* may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

For all positions discussed in the present invention, numbering is according to the EU index as in Kabat (Kabat et al., 1991, *Sequences of Proteins of Immunological Interest*; 5th Ed., United States Public Health Service, National Institutes of Health, Bethesda, entirely incorporated by reference). Those skilled in the art of antibodies will appreciate that this convention consists of nonsequential numbering in specific regions of an immunoglobulin sequence, enabling a normalized reference to conserved positions in immunoglobulin families. Accordingly, the positions of any given immunoglobulin as defined by the EU index will not necessarily correspond to its sequential sequence.

Example 1. Generation of Anti-IsdA Antibodies, Anti-IsdB Antibodies, and Anti-Protein A Antibodies Anti-IsdA antibodies and anti-IsdB antibodies were obtained by immunizing a genetically engineered mouse comprising DNA encoding human immunoglobulin heavy and kappa light chain variable regions with two immunogens, IsdA-6×His and IsdB-6×His. comprising recombinant IsdA. Anti-Protein A antibodies were obtained by immunizing a genetically engineered mouse comprising DNA encoding human immunoglobulin heavy and kappa light chain variable regions with an immunogen comprising wild type Protein A or mutant Protein A (the mutant version does not bind the Fc and is termed "SpAkkaa" (PMID: 23982075)).

The antibody immune response was monitored by an antigen-specific immunoassay, i.e. an immunoassay specific for IsdA, IsdB, or Protein A. When a desired immune response is achieved, splenocytes can be harvested and fused with mouse myeloma cells to preserve their viability and form hybridoma cell lines. The hybridoma cell lines can be screened and selected to identify cell lines that produce IsdA-specific antibodies, IsdB-specific antibodies or Protein A-specific antibodies. Using this technique chimeric antibodies (i.e., antibodies possessing human variable domains and mouse constant domains) can be obtained. In this instance, however, fully human antibodies were isolated directly from antigen-positive B cells without fusion to myeloma cells, as described in US 2007/0280945A1.

The antibody heavy chain constant regions are human IgG1 Fc regions having amino acid substitutions of H at EU position 435 with an R (H435R), or a substitution of Y at EU position 436 with an F (Y436F), or a substitution of H435R and Y436F. The mutated form of the IgG1 having the two amino acid substitutions H435R and Y436F is referred to throughout this disclosure as */*. The */* mutations were introduced into the expression vectors used to generate the fully human anti-Protein A, IsdB or IsdA antibodies provided in Table 1.

Certain biological properties of the exemplary antibodies generated in accordance with the methods of this Example, are described in detail in the Examples set forth below.

Example 2. Heavy and Light Chain Variable Region Amino Acid and Nucleic Acid Sequences of Anti-IsdA Antibodies, Anti-IsdB Antibodies, and Anti-Protein A Antibodies Table 1 provides the amino acid sequence identifiers of the heavy and light chain variable regions and CDRs of selected antibodies provided herein. The corresponding nucleic acid sequence identifiers are provided in Table 2. Table 3 provides the full length heavy and light chain sequence identifiers for two anti-IsdB antibodies, one with the */* heavy chain mutations and one without.

TABLE 1

| Antibody | Amino Acid Sequence Identifiers | | | | | | | |
|---|---|---|---|---|---|---|---|---|
| | SEQ ID NOs: | | | | | | | |
| Designation | HCVR | HCDR1 | HCDR2 | HCDR3 | LCVR | LCDR1 | LCDR2 | LCDR3 |
| H1xH20334P2*/* (anti-IsdA) | 2 | 4 | 6 | 8 | 10 | 12 | 14 | 16 |
| H1xH15140P*/* (anti-Protein A) | 18 | 20 | 22 | 24 | 26 | 28 | 30 | 32 |
| H1xH20295P2*/* H1H20295P2WT (anti-IsdB) | 34 | 36 | 38 | 40 | 42 | 44 | 46 | 48 |

TABLE 2

Nucleic Acid Sequence Identifiers

| Antibody Designation | SEQ ID NOs: | | | | | | |
|---|---|---|---|---|---|---|---|
| | HCVR | HCDR1 | HCDR2 | HCDR3 | LCVR | LCDR1 | LCDR2 | LCDR3 |
| H1xH20334P2*/* (anti-IsdA) | 1 | 3 | 5 | 7 | 9 | 11 | 13 | 15 |
| H1xH15140P*/* (anti-Protein A) | 17 | 19 | 21 | 23 | 25 | 27 | 29 | 31 |
| H1xH20295P2*/* H1H20295P2WT (anti-IsdB) | 33 | 35 | 37 | 39 | 41 | 43 | 45 | 47 |

TABLE 3

Sequence Identifiers for full length heavy and light chain sequences for H1H20295P2 wild type (WT) and mutated form (*/*)

| | SEQ ID NOs: | | | |
|---|---|---|---|---|
| | Full length Heavy Chain | | Full length Light Chain | |
| Antibody Designation | Nucleic Acid | Amino Acid | Nucleic Acid | Amino Acid |
| H1H20295P2WT (anti-IsdB) | 49 | 50 | 51 | 52 |
| H1xH20295P2*/* (anti-IsdB*/*) | 53 | 54 | 51 | 52 |

The antibodies provided herein can be of any isotype as long as the immunoglobulin heavy chain differs from that of an unmodified parent anti-*S. aureus* IgG antibody by at least two amino acid substitutions: H435R and Y436F, by EU index numbering. The mutated form of the IgG1 having the two amino acid substitutions H435R and Y436F is referred to throughout this disclosure as */*. Anti-IsdA, anti-IsdB, and anti-Protein A antibodies of the invention may comprise variable domain and CDR sequences as set forth in Tables 1 and 2 and a human Fc domain of isotype IgG1 having the H435R and Y436F mutations according to SEQ ID NO: 58. For certain applications or experiments the Fc domain may be a mouse Fc domain. As will be appreciated by a person of ordinary skill in the art, an antibody having a particular Fc isotype can be converted to an antibody with a different Fc isotype having the equivalent H435R and Y436F mutations (e.g., an antibody with a mouse IgG3 Fc can be converted to an antibody with a human IgG1*/*, etc.), but in any event, the variable domains (including the CDRs)—which are indicated by the numerical identifiers shown in Tables 1 and 2—will remain the same, and the binding properties are expected to be identical or substantially similar regardless of the nature of the Fc domain in as much as the H435R and Y436F mutations are present.

Example 3. Biacore Binding Kinetics of */* Modified Anti-IsdA Monoclonal Antibodies and Anti-Protein a Antibodies Binding to IsdA.6xHis and Protein A, Respectively, Measured at 25° C. and 37° C.

The equilibrium dissociation constants ($K_D$) to Protein A and IsdA.6xHis reagents binding to purified anti-IsdA*/* and anti-Protein A*/* monoclonal antibodies were determined using a real-time surface plasmon resonance based Biacore T200 or Biacore 4000 biosensor. All binding studies were performed in 10 mM HEPES, 150 mM NaCl, 3.4 mM EDTA and 0.05% v/v Tween-20, pH 7.4 (HBS-EP) running buffer at 25° C. and 37° C. The Biacore CM5 sensor chip surface was first derivatized by amine coupling with the anti-human Fc monoclonal antibody (GE Healthcare Cat. #BR100839) or anti-human Fcγ specific F(ab')2)polyclonal antibody (Jackson ImmunoResearch Cat. #109-006-008) to capture anti-IsdA*/* or anti-Protein A*/* monoclonal antibody. Binding studies were performed on different concentrations of IsdA.6xHis (90 nM-3.33 nM; 3-fold serial dilution) and Protein A (100 nM-0.39 nM; 4-fold serial dilution) prepared in HBS-EP running buffer. Proteins were injected over the captured anti-IsdA*/* and anti-Protein A*/* monoclonal antibody surface for 3-3.5 minutes at a flow rate of 30-504/minute, while the dissociation of monoclonal antibody bound IsdA.6xHis and Protein A reagent was monitored for 5-10 minutes in HBS-EP running buffer. The association rate (ka) and dissociation rate (kd) were determined by fitting the real-time binding sensorgrams to a 1:1 binding model with mass transport limitation using Scrubber 2.0c curve-fitting software. Binding dissociation equilibrium constant ($K_D$) and dissociative half-life (t½) were calculated from the kinetic rates as:

$$K_D(M) = \frac{kd}{ka}, \text{ and } t1/2 \text{ (min)} = \frac{\ln(2)}{60 * kd}$$

Binding kinetics parameters for IsdA.6xHis and Protein A binding to anti-IsdA*/* and anti-Protein A*/* monoclonal antibody of the invention at 25° C. and 37° C. are shown in Tables 4 through 7.

At 25° C., anti-IsdA*/* monoclonal antibodies bound to IsdA.6xHis with $K_D$ value of 1.28 nM, as shown in Table 4. At 37° C., anti-IsdA*/* monoclonal antibodies bound to IsdA.6xHis with $K_D$ value of 3.49 nM, as shown in Table 5.

At 25° C., anti-Protein A*/* monoclonal antibodies bound to Protein A with $K_D$ value of 204 pM, as shown in Table 6. At 37° C., anti-Protein A*/* monoclonal antibodies bound to Protein A with $K_D$ value of 98.6 pM, as shown in Table 7.

TABLE 4

Binding kinetics parameters of IsdA.6xHis binding to anti-IsdA*/* monoclonal antibodies at 25° C.

| mAb Captured | mAb Capture Level (RU) | 90 nM Ag Bound (RU) | $k_a$ (1/Ms) | $k_d$ (1/s) | $K_D$ (M) | t½ (min) |
|---|---|---|---|---|---|---|
| H1xH20334P2*/* | 101.3 ± 0.8 | 98 | 3.48E+05 | 4.46E−04 | 1.28E−09 | 26 |

TABLE 5

Binding kinetics parameters of IsdA.6xHis binding to anti-IsdA*/* monoclonal antibodies at 37° C.

| mAb Captured | mAb Capture Level (RU) | 90 nM Ag Bound (RU) | $k_a$ (1/Ms) | $k_d$ (1/s) | $K_D$ (M) | t½ (min) |
|---|---|---|---|---|---|---|
| H1xH20334P2*/* | 136.0 ± 1.4 | 116 | 4.79E+05 | 1.67E−03 | 3.49E−09 | 7 |

TABLE 6

Binding kinetics parameters of Protein A binding to anti-Protein A*/* monoclonal antibodies at 25° C.

| mAb Captured | mAb Capture Level (RU) | 100 nM Ag Bound (RU) | $k_a$ (1/Ms) | $k_d$ (1/s) | $K_D$ (M) | t½ (min) |
|---|---|---|---|---|---|---|
| H1xH15140P*/* | 133 ± 0.7 | 44 | 3.81E+05 | 7.78E−05 | 2.04E−10 | 149 |

TABLE 7

Binding kinetics parameters of Protein A binding to anti-Protein A*/* monoclonal antibodies at 37° C.

| mAb Captured | mAb Capture Level (RU) | 100 nM Ag Bound (RU) | $k_a$ (1/Ms) | $k_d$ (1/s) | $K_D$ (M) | t½ (min) |
|---|---|---|---|---|---|---|
| H1xH15140P*/* | 51 ± 1.4 | 19 | 1.19E+06 | 1.17E−04 | 9.86E−11 | 99 |

Example 4: S. aureus ELISA to Assess the Specificity of Antibody Binding in the Presence of Protein A S. aureus expresses an IgG binding protein called Protein A on the pathogen's surface. Protein A contains 4-5 repeats of an IgG binding domain that has a high affinity for the Fc portion of human IgG1, IgG2, and IgG4 antibodies. See Loghem et al., 1982, staphylococcal Protein A and human IgG subclasses and allotypes Scand. J. Immunol. 15, 275-278. Human IgG3 antibodies have amino acid substitutions that result in greatly diminished Protein A binding (H435R, Y436F, referred to as */*). Specificity of antibody binding of hIgG1 and hIgG1*/* antibodies to intact S. aureus wild-type and Protein A deficient strains was explored in this assay.

Anti-IsdB*/* and Protein A*/* antibodies of this invention were assessed for binding to S. aureus Newman wild-type and Protein A deficient strains to characterize the specificity of antibody binding in the presence and absence of Protein A. Overnight S. aureus cultures were grown in RPMI, washed twice with PBS and then resuspended at an OD=0.25. Black Nunc microtiter plates were coated with 100 uL/well of the S. aureus suspension and incubated overnight at 4° C. The following morning, plates were washed three times with ADB (1% BSA in PBS) and blocked for two hours with 200 uL of blocking buffer (3% BSA+0.5% Tween 20 in PBS) at room temperature. Next, plates were washed three times with ADB and then incubated with the primary antibody at the indicated concentration at room temperature for one hour. Secondary antibody (chicken anti-human HRP) was added at a 1:4000 dilution and incubated for 1 hour, after which plates were washed three times with ADB. Pico substrate was added for 10 minutes and plates were read on a plate reader to measure luminescent signal.

A hIgG1 control, but not a hIgG1*/* control, bound to S. aureus Newman wild-type in a Protein A dependent manner (FIG. 1), demonstrating broad binding of the hIgG1 isotype. Anti-IsdB hIgG1 and hIgG1*/* monoclonal antibodies bound similarly to the Protein A deficient strain, showing that */* modifications do not impact binding to target. See also Table 8.

TABLE 8

S. aureus binding ELISA with hIgG1 and hIgG1*/* format antibodies

| Antibody | EC50 ELISA binding in log[M] | |
|---|---|---|
| | S. aureus Newman WT | S. aureus Newman Δspa |
| hIgG1 control (REGN1932) | 3.05E−11 | no binding |
| anti-IsdB hIgG1 (H1H20295P2) | 2.27E−11 | 3.01E−11 |
| hIgG1*/* control (REGN4440) | 1.90E−07 | no binding |
| anti-IsdB hIgG1*/* (H1xH20295P27*) | 3.14E−11 | 6.23E−11 |
| anti-Protein A hIgG1*/* (H1xH15140P) | 1.54E−11 | 2.74E−09 |

Example 5: S. aureus Survival in Complement Preserved Serum and Antibody-Induced Killing by hIgG1*/* Monoclonal Antibodies S. aureus evades complement dependent killing through expression of virulence factors that interfere with complement activation at various steps prior to membrane attack complex formation. See Thammavongsa, et al. 2015. staphylococcal manipulation of host immune responses, *Nat Rev Microbiol*, 13: 529-43. Here, the ability of antibodies to overcome complement evasion and initiate antibody-induced serum killing was tested.

Anti-Protein A and IsdB hIgG1*/* antibodies of this invention were assessed for their ability to promote killing of S. aureus Newman in normal human serum. Briefly, a culture of S. aureus Newman was grown in RPMI overnight, washed in PBS, and resuspended in RPMI+0.05% BSA to a concentration of 1×10$^5$ colony forming units (CFU)/mL. Normal human serum (NHS) was thawed in a 37° C. water bath and then kept on ice, then a portion of the NHS was removed for heat inactivation (HI) at 56° C. for 30 minutes. In triplicate, 100 uL of the S. aureus suspension was mixed with test antibody for 10 minutes and then 100 uL of the indicated serum was added for a final concentration of 50% serum and 100 ug/mL monoclonal antibody. The test samples were then incubated shaking (100 rpm) at 37° C. for 2, 4, or 6h. After incubation, 100 uL of agglutination lysis buffer (PBS supplemented with 200 U Streptokinase, 2 ug/mL RNase, 10 ug/mL DNase, 0.5% saponin per ml of PBS) was added to the samples, vigorously vortexed and incubated at 37° C. for 10 minutes. S. aureus survival was enumerated by colony forming units through serial dilution and plating onto TSA.

Figure 2:
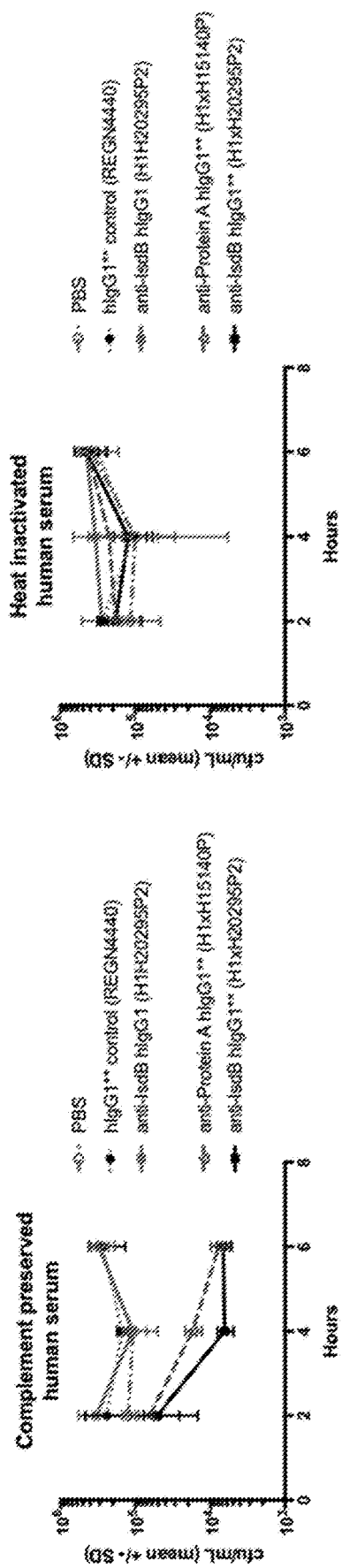

Results from a representative experiment are shown in Table 9 and in FIG. 2. Neither the hIgG1*/* isotype control nor the anti-IsdB hIgG1 format antibodies impacted survival of S. aureus in NHS, while both the anti-Protein A and anti-IsdB hIgG1*/* monoclonal antibodies promoted killing over time. Heat inactivation ablated activity of the anti-staphylococcal hIgG1*/* antibodies, suggesting that complement was required for the antibody-dependent killing.

TABLE 9

S. aureus Newman survival in human serum with anti-IsdB*/* and anti-Protein A*/* antibody treatment

| Antibody (100 ug/mL) | cfu/mL | | standard deviation | |
|---|---|---|---|---|
| 6 hour incubation | NHS | HI serum | NHS | HI serum |
| PBS | 3.5E+05 | 4.3E+05 | 1.2E+05 | 2.2E+05 |
| hIgG1*/* control (REGN4440) | 2.5E+05 | 3.5E+05 | 1.4E+05 | 9.0E+04 |
| anti-Protein A hIgG1*/* (H1xH15140P) | 8.5E+03 | 4.8E+05 | 2.2E+03 | 1.2E+05 |
| anti-IsdB hIgG1*/* (H1xH20295P2) | 6.0E+03 | 3.8E+05 | 1.5E+03 | 2.0E+05 |
| anti-IsdB hIgG1 (H1H20295P2) | 2.8E+05 | 4.3E+05 | 8.0E+04 | 9.0E+04 |

Example 6: Testing hIgG1 and hIgG1*/* Formatted Anti-IsdB Antibodies in a S. aureus Disseminated Infection Model S. aureus causes disseminated infection in mice when injected intraperitoneally with high levels of bacterial replication in the kidneys. See Wang and Lee, 2016, Murine Models of Bacteremia and Surgical Wound Infection for the Evaluation of *Staphylococcus aureus* Vaccine Candidates, Methods Mol Biol, 1403: 409-18. In this experiment, hIgG1 and hIgG1*/* formatted anti-IsdB antibodies were tested for their ability to decrease kidney burden when administered 1 day post S. aureus infection.

Anti-IsdB H1xH20295P2 and H1H20295P2*/* antibodies of this invention were assessed for therapeutic efficacy against S. aureus Newman in a disseminated infection model. Briefly, a culture of S. aureus Newman was grown in TSB overnight, subcultured and grown to mid-logarithmic phase (OD600=1). The culture was then washed in PBS twice and resuspended in PBS at an optical density of 3 (7.5×10$^8$ cfu/mL). Mice were injected intraperitoneally with 200 uL of the bacterial suspension. At one day post infection, mice were treated with 5 mg/kg or 10 mg/kg of monoclonal antibody in PBS, as indicated, in 100 uL administered subcutaneously. Mice were monitored for weight loss and body condition until 4 days post infection, at which point they were euthanized. Kidneys were removed and resuspended in 0.1% Triton X100 in PBS and homogenized using C-max dissociation tubes. Bacteria were enumerated by colony forming units through serial dilution and plating onto TSA.

Figure 3:
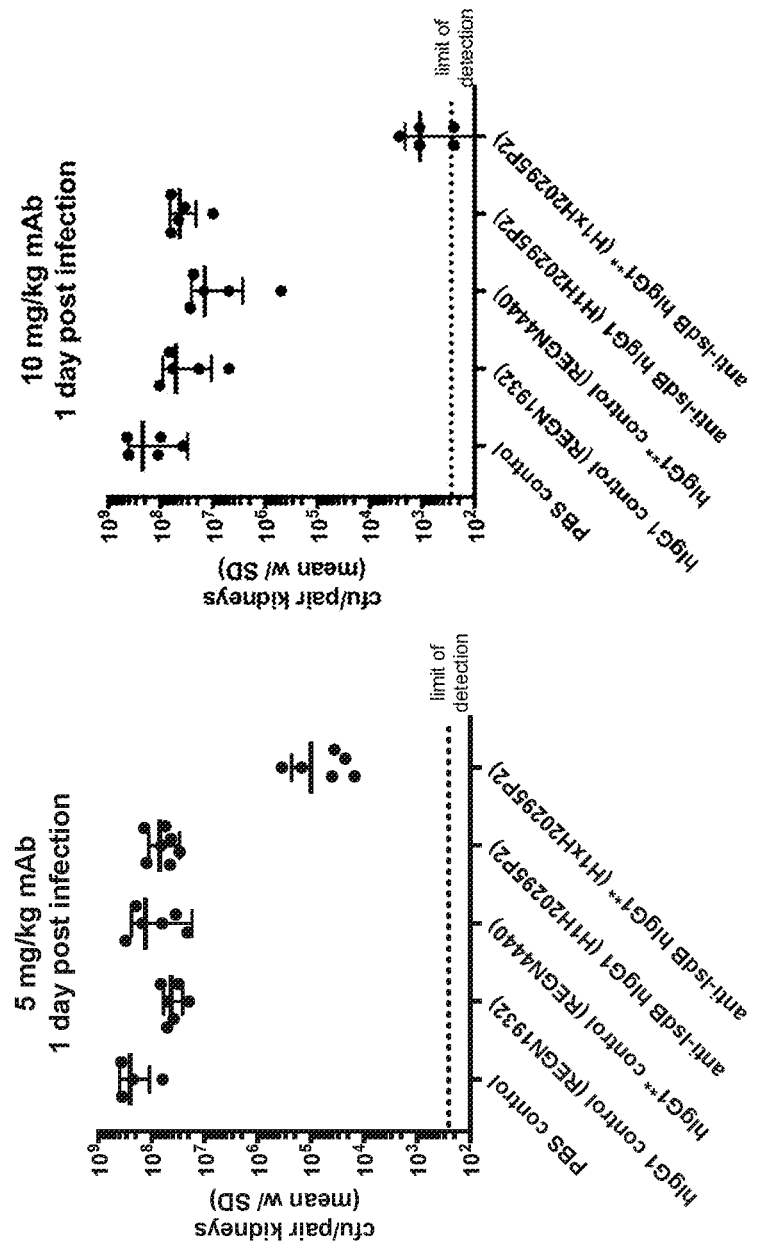

Results from two independent experiments are presented in Table 10. The anti-IsdB monoclonal antibody in a hIgG1*/* format reduced S. aureus kidney burden by 3-4 logs, while the hIgG1 format of the same antibody was ineffective at reducing S. aureus load compared to the isotype control. See also FIG. 3.

TABLE 10

S. aureus Kidney burden in antibody treated mice

| | Experiment 1 (5 mg/kg monoclonal antibody) | | Experiment 2 (10 mg/kg monoclonal antibody) | |
|---|---|---|---|---|
| Antibody | median cfu/pair kidneys | standard deviation | median cfu/pair kidneys | standard deviation |
| PBS control | 2.9E+08 | 1.5E+08 | 1.1E+08 | 1.9E+08 |
| hIgG1 control (REGN1932) | 4.4E+07 | 1.7E+07 | 5.9E+07 | 4.0E+07 |

TABLE 10-continued

S. aureus Kidney burden in antibody treated mice

|  | Experiment 1 (5 mg/kg monoclonal antibody) | | Experiment 2 (10 mg/kg monoclonal antibody) | |
| --- | --- | --- | --- | --- |
| Antibody | median cfu/pair kidneys | standard deviation | median cfu/pair kidneys | standard deviation |
| hIgG1*/* control (REGN4440) | 1.1E+08 | 1.1E+08 | 1.5E+07 | 1.2E+07 |
| anti-IsdB hIgG1 (H1H20295P2) | 5.5E+07 | 4.2E+07 | 4.6E+07 | 2.2E+07 |
| anti-IsdB hIgG1*/* (H1xH20295P2) | 3.8E+04 | 1.3E+05 | 1.1E+03 | 1.0E+03 |

Example 7: Antibody-Induced Killing of S. aureus by hIgG1*/* Monoclonal Antibodies in Normal Human Serum As described above in Example 5, antibodies in this experiment were tested for their ability to overcome bacterial complement evasion and initiate antibody-induced serum killing of several S. aureus strains, including MSSA strain Newman and MRSA clinical isolates N315 and MW2. See Kuroda, M., et al., Whole genome sequencing of methicillin-resistant Staphylococcus aureus. Lancet, 2001. 357 (9264): p. 1225-40. Baba, T., et al., Genome and virulence determinants of high virulence community-acquired MRSA. Lancet, 2002. 359(9320): p. 1819-27.

Anti-Protein A and IsdB hIgG1*/* antibodies were assessed for their ability to promote killing of S. aureus Newman, N315 or MW2 in normal human serum. S. aureus cultures were grown in RPMI overnight, washed in PBS, and resuspended in RPMI+0.05% BSA to a concentration of $1 \times 10^5$ colony forming units (CFU)/mL. Normal human serum (NHS) was thawed in a 37° C. water bath and then kept on ice. In triplicate, 100 uL of the S. aureus suspension, S. aureus Newman, N315 or MW2, respectively, was mixed with test antibody and 100 uL of the indicated serum was added for a final concentration of 50% serum and 100 ug/mL monoclonal antibody. The test samples were then incubated while shaking (100 rpm) at 37° C. for six hours. After incubation, 100 uL of agglutination lysis buffer (PBS supplemented with 200U Streptokinase, 2 ug/mL RNase, 10 ug/mL DNase, 0.5% saponin per ml of PBS) was added to the samples, vigorously vortexed and incubated at 37° C. for ten minutes. S. aureus survival was enumerated by colony forming units through serial dilution and plating onto TSA.

Figure 4:
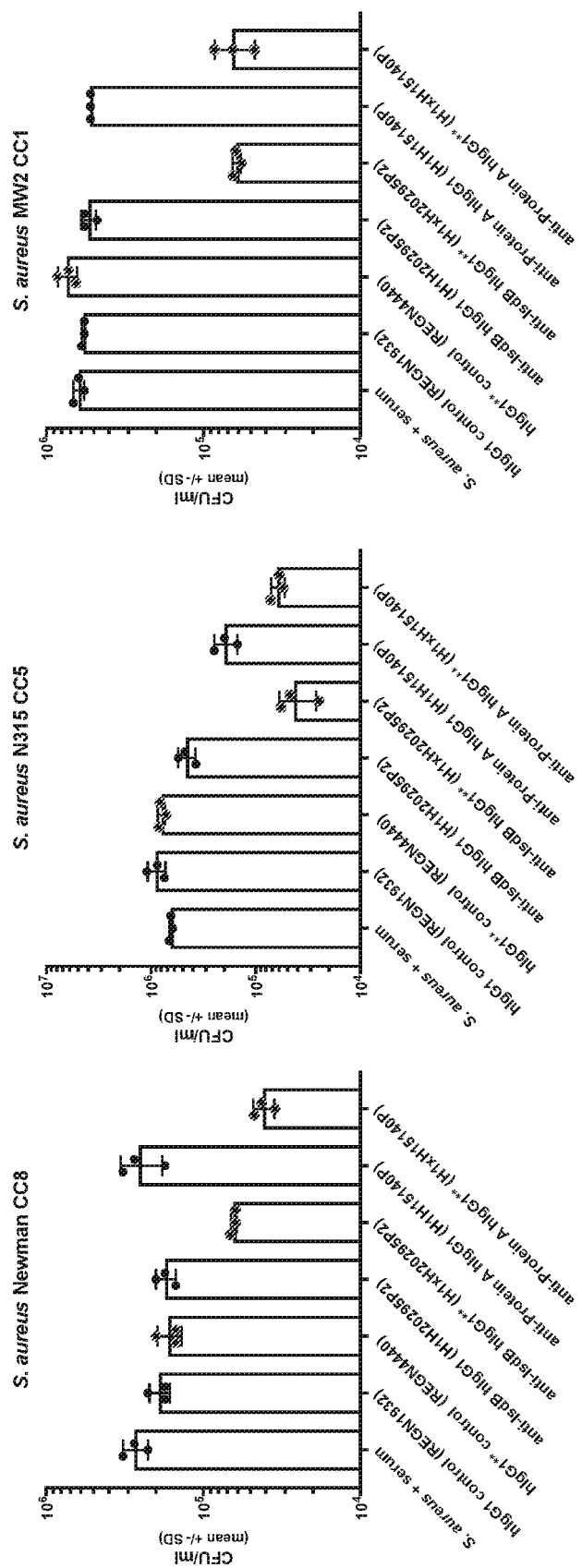

Data are shown in Table 11. The control antibodies, anti-IsdB hIgG1 and anti-Protein A hIgG1 monoclonal antibodies did not impact survival of S. aureus strains in normal human serum, while both the anti-Protein A hIgG1*/* and anti-IsdB hIgG1*/* monoclonal antibodies promoted killing over six hours. Antibody induced killing by anti-staphylococcal hIgG1*/* Protein A and IsdB monoclonal antibodies in normal human serum was similar across MSSA strain Newman and MRSA clinical isolates N315 and MW2. See also FIG. 4.

TABLE 11

S. aureus survival in human serum with anti-IsdB and anti-Protein A antibody treatment

| | S. aureus Newman | | S. aureus N315 | | S. aureus MW2 | |
| --- | --- | --- | --- | --- | --- | --- |
| Antibody (100 ug/mL) 6 hour incubation | cfu/mL | standard deviation | cfu/mL | standard deviation | cfu/mL | standard deviation |
| S. aureus + serum | 2.75E+05 | 5.00E+04 | 6.50E+05 | 2.50E+04 | 6.25E+05 | 5.00E+04 |
| hIgG1 control (REGN1932) | 1.75E+05 | 2.89E+04 | 8.75E+05 | 1.77E+05 | 5.75E+05 | 1.44E+04 |
| hIgG1*/* control (REGN4440) | 1.50E+05 | 2.89E+04 | 8.25E+05 | 6.61E+04 | 7.25E+05 | 1.01E+05 |
| anti-IsdB hIgG1 (H1H20295P2) | 1.75E+05 | 2.50E+04 | 4.75E+05 | 8.78E+04 | 5.75E+05 | 5.77E+04 |
| anti-IsdB hIgG1*/* (H1xH20295P2) | 6.25E+04 | 2.89E+03 | 4.75E+04 | 1.66E+04 | 6.25E+04 | 3.82E+03 |
| anti-Protein A hIgG1 (REGN6410) | 2.75E+05 | 7.64E+04 | 2.00E+05 | 5.00E+04 | 5.25E+05 | 0.00E+00 |
| anti-Protein A hIgG1*/* (H1xH15140P) | 4.25E+04 | 6.29E+03 | 6.00E+04 | 9.01E+03 | 6.50E+04 | 1.88E+04 |

Example 8: Testing Anti-IsdB and Anti-Protein a hIgG1 and hIgG1*/* Formatted Antibodies in a *S. aureus* Disseminated Infection Model Using the same *S. aureus* disseminated infection model mentioned in Example 6, both anti-IsdB and anti-Protein A hIgG1 and hIgG1*/* formatted antibodies were tested for their ability to decrease kidney burden when administered one day post *S. aureus* infection.

Anti-IsdB H1xH20295P2 (hIgG1*/*) and H1H20295P2 and anti-Protein A H1xH15140P (hIgG1*/*) and REGN6410 (H1H15140P) antibodies were assessed for therapeutic efficacy against *S. aureus* Newman. A culture of *S. aureus* Newman was grown in TSB overnight, subcultured and grown to mid-logarithmic phase (OD600=1). The culture was then washed in PBS twice and resuspended in PBS at an optical density of 3 ($7.5 \times 10^8$ cfu/mL). Mice were injected intraperitoneal with 200 uL of the bacterial suspension. At one day post infection, mice were treated with 10 mg/kg of monoclonal antibody in PBS, as indicated, in 100 uL administered subcutaneously. Mice were monitored for weight loss and body condition until four days post infection, at which point they were euthanized. Kidneys were removed and resuspended in 0.1% Triton X100 in PBS and homogenized using C-max dissociation tubes. Bacteria were enumerated by colony forming units through serial dilution and plating onto TSA.

Figure 5:
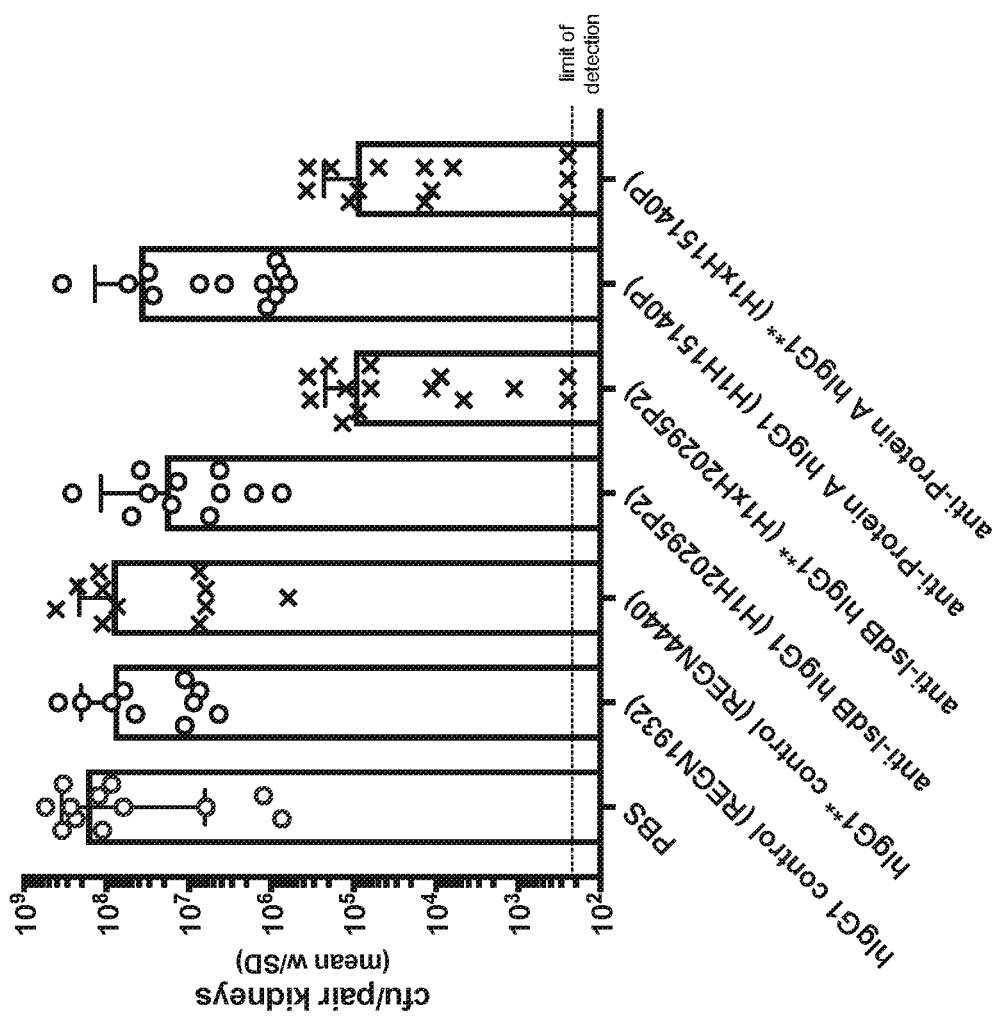

Results are presented in Table 12. The anti-IsdB and anti-Protein A monoclonal antibodies in a hIgG1*/* format reduced *S. aureus* kidney burden by 3-4 logs, while the hIgG1 format of the same antibodies was ineffective at reducing *S. aureus* load compared to the isotype control. See also FIG. 5 presenting results from two independent experiments.

TABLE 12

*S. aureus* kidney burden in antibody treated mice

| Antibody | median cfu/pair kidneys | standard deviation |
|---|---|---|
| PBS | 1.2E+08 | 1.7E+08 |
| hIgG1*/* control (REGN4440) | 4.1E+07 | 1.3E+08 |
| hIgG1 control (REGN1932) | 2.8E+07 | 1.2E+08 |
| anti-IsdB hIgG1 (H1H20295P2) | 9.7E+06 | 9.9E+07 |
| anti-IsdB hIgG1*/* (H1xH20295P2) | 6.3E+04 | 1.2E+05 |
| anti-Protein A hIgG1 (REG6410-H1H15140P) | 2.5E+06 | 9.9E+07 |
| anti-Protein A hIgG1*/* (H1xH15140P) | 1.4E+04 | 1.3E+05 |

Example 9: Therapeutic Treatment in a Disseminated Infection Model Using Wild-Type and Knock Out Mice Human IgG1 antibodies can flag bacteria for destruction via effector function by recruiting the complement component C1q and/or immune cells expressing FcgR. See Lu, et al., *Beyond binding: antibody effector functions in infectious diseases*. Nat Rev Immunol, 2018, 18(1): 46-61. C1q initiates the classical complement pathway to induce phagocytosis through complement receptors, formation of the lytic membrane attack complex, and additional recruitment of innate immune cells. C3 is a critical component of the complement pathway required for activity. See Dobo, et al., *Be on Target: Strategies of Targeting Alternative and Lectin Pathway Components in Complement-Mediated Diseases*. Front Immunol, 2018, 9: 1851. FcgRs are expressed on diverse immune cells and hIgG1 Fc/FcgR engagement can result in phagocytosis, degranulation, cellular cytotoxicity and release of chemoattractants. Mouse FcgRIII and FcgRIV contribute to activation of immune cells that play a key role in effector function. See Bruhns, P. and F. Jonsson, *Mouse and human FcR effector functions*. Immunol Rev, 2015, 268(1): 25-51.

*S. aureus* causes disseminated infection in mice when injected intraperitoneally, with high levels of bacterial replication in the kidneys. As described above in Examples 6 and 8, hIgG1*/* format anti-IsdB and Protein A monoclonal antibodies were able to reduce *S. aureus* kidney burden, while the hIgG1 format of the same antibodies were ineffective. Thus, by avoiding Protein A Fc binding, the hIgG1*/* antibodies gain the ability to promote effector function, as activity did not rely exclusively on Fab binding to the bacteria through the variable domains.

Additionally, as shown in Examples 5 and 7, hIgG1*/* anti-Protein A and anti-IsdB monoclonal antibodies promoted staphylococcal killing in normal human serum. To investigate whether complement or FcgR were required for efficacy of hIgG1*/* format monoclonal antibodies in vivo, *S. aureus* kidney burden was assessed in wild-type, C3 deficient, or FcgRIIb/FcgRIII/FcgRIV knock out mice following treatment with 10 mg/kg monoclonal antibody. The antibiotic daptomycin was included as a control treatment group, as this antibiotic directly disrupts the bacterial cell membrane and does not require effector function. Heidary, et al., *Daptomycin*. J Antimicrob Chemother, 2018, 73(1): 1-11.

Anti-IsdB H1xH20295P2 and anti-Protein A H1xH15140P antibodies disclosed herein were assessed for therapeutic efficacy against *S. aureus* Newman in a disseminated infection model using complement and FcgR deficient mice. Complement deficient mice were generated by direct replacement of mouse C3 gene with a LacZ reporter. $C3^{-/-}$ knockout mice were compared to $C3^{+/+}$ littermate controls. For the FcgR deficient mice, FcgRIIb/FcgRIII/FcgRIV knock out mice were generated by direct replacement of mouse Fcgr2, Fcgr3, Fcgr4 genes with a neomycin resistant gene. FcgRIIb/FcgRIII/FcgRIV knock out mice were compared to background matched wild-type (VG) mice that are a mix of 75% C57BL/6 and 25% 129 strains.

To infect, a culture of *S. aureus* Newman was grown in TSB overnight, subcultured and grown to mid-logarithmic phase (OD600=1). The culture was then washed with PBS twice and resuspended in PBS at $7.5 \times 10^8$ cfu/mL for infection of WT and FcgRIIb/FcgRIII/FcgRIV knock out mice or $4.35 \times 10^8$ cfu/mL for infection of $C3^{-/-}$ mice, as they are more susceptible to infection. Mice were injected intraperitoneally with 200 uL of the bacterial suspension. At one day post infection, mice were treated once with the indicated antibody resuspended in 100 uL PBS for a final dose of 10 mg/kg administered subcutaneously. An additional group of mice were injected once daily with 50 mg/kg daptomycin starting one day post infection. Mice were monitored for weight loss and body condition until four days post infection, at which point they were euthanized. Kidneys were removed and resuspended in 0.1% Triton X100 in PBS and homogenized using C-max dissociation tubes. Bacteria were enumerated by colony forming units through serial dilution and plating onto TSA.

Figure 6:
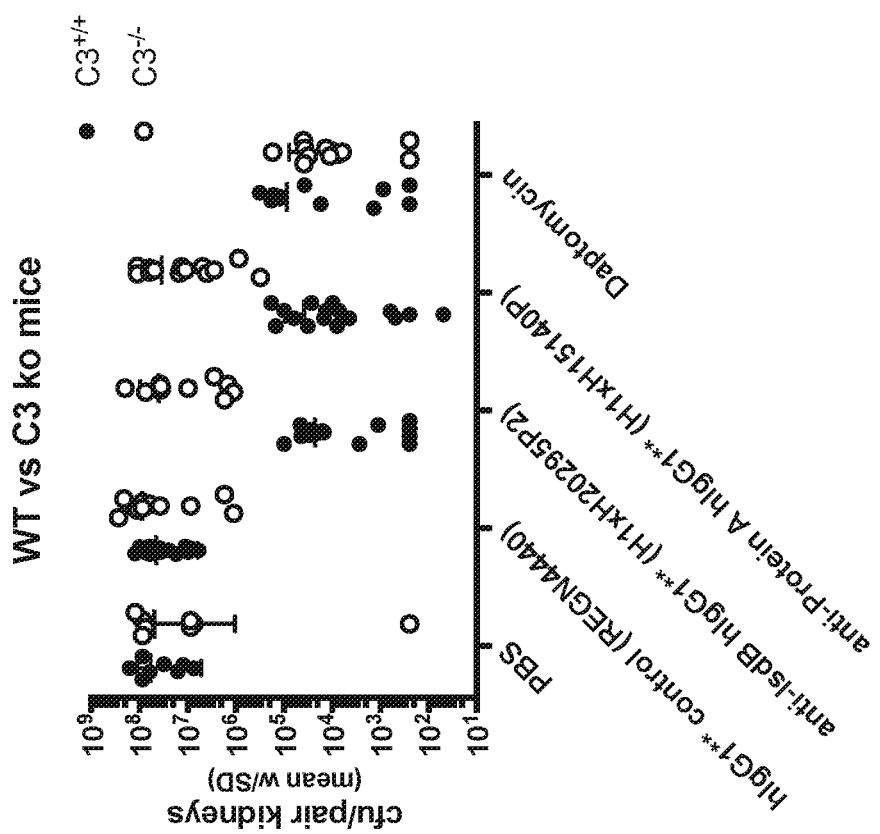
Figure 7:
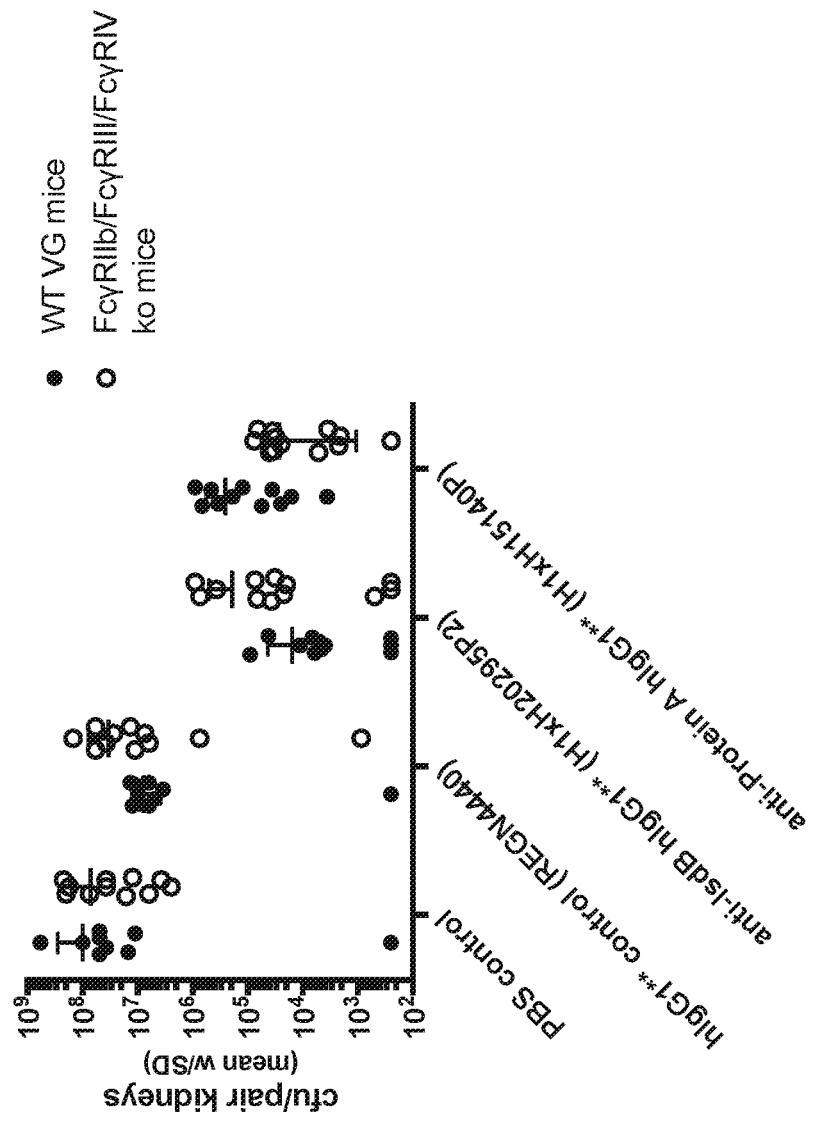

Results from two independent experiments are presented in Table 13 and Table 14 (see also FIGS. 6 and 7, respectively). The anti-IsdB and anti-Protein A hIgG1*/* monoclonal antibodies reduced S. aureus kidney burden by 3-4 logs in wild-type mice, whereas the C3 deficient mice had a mean kidney burden similar to the hIgG1*/* control and untreated groups, demonstrating that C3 is required for antibody efficacy. Daptomycin, which has a mechanism of action independent of complement, was equally protective in C3 competent and deficient backgrounds. Mice deficient for FcgRIIb/FcgRIII/FcgRIV, however, were still protected by the anti-IsdB and anti-Protein A hIgG1*/* monoclonal antibodies, demonstrating that these FcgRs were not required for activity. These data suggest that the anti-Protein A and anti-IsdB hIgG1*/* antibodies promote staphylococcal killing through a mechanism of action that requires complement activity.

TABLE 13

Complement component C3 is required for efficacy of anti-IsdB and anti-Protein A hIgG17* monoclonal antibodies

| | $C3^{+/+}$ littermate controls | | $C3^{-/-}$ knockouts | |
| --- | --- | --- | --- | --- |
| Antibody | median cfu/pair kidneys | standard deviation | median cfu/pair kidneys | standard deviation |
| PBS control | 4.7E+07 | 5.3E+07 | 4.2E+07 | 4.9E+07 |
| hIgG1*/* control (REGN4440) | 3.8E+07 | 3.9E+07 | 7.5E+07 | 9.2E+07 |
| anti-IsdB hIgG1*/* (H1xH20295P2) | 1.9E+04 | 2.7E+04 | 3.5E+07 | 5.8E+07 |
| anti-Protein A hIgG1*/* (H1xH15140P) | 1.4E+04 | 5.8E+04 | 1.4E+07 | 4.1E+07 |
| Daptomycin | 2.8E+04 | 1.1E+05 | 1.3E+04 | 4.8E+04 |

TABLE 14

Low affinity FcγRIIb/FcγRIII/FcγRIV are not required for efficacy of anti-IsdB and anti-Protein A hIgG1*/* monoclonal antibodies

| | Wild-type VG mice (75% C57BL/6, 25% 129) | | FcγRIIb/FcγRIII/FcγRIV KO | |
| --- | --- | --- | --- | --- |
| Antibody | median cfu/pair kidneys | standard deviation | median cfu/pair kidneys | standard deviation |
| PBS control | 5.0E+07 | 1.9E+08 | 3.8E+07 | 8.6E+07 |
| hIgG1*/* control (REGN4440) | 1.0E+07 | 4.2E+06 | 1.4E+07 | 4.4E+07 |
| anti-IsdB hIgG1*/* (H1xH20295P2) | 5.1E+03 | 2.8E+04 | 3.5E+04 | 3.2E+05 |
| anti-Protein A hIgG1*/* (H1xH15140P) | 1.3E+05 | 3.1E+05 | 2.8E+04 | 2.6E+04 |

Example 10: Testing Anti-Protein a hIgG1 and hIgG1*/* Formatted Antibodies in a Canine Model of S. pseudintermedius Pyoderma Laboratory beagles are inoculated with a methicillin-susceptible strain of S. pseudintermedius. One mL of approximately $10^7$, $10^8$, $10^9$ CFU per ml will be topically applied onto clipped and tape stripped area of dog skin, and then treated with a dermaroller (microneedle size: 500 μm) immediately after administration. Dogs will be administered anti-Protein A hIgG1*/*, anti-Protein A hIgG1, or isotype control (hIgG1*/* control REGN4440 L2) and monitored daily. Suspect pustules will be cultured for S. pseudintermedius and evaluated by cytological and histopathological methods. Assessment of papules and pustules at all three bacterial inoculation sites will be made every 24 hours. Cytological samples of all skin lesions will be taken to identify neutrophils with intracellular cocci. Any subcorneal neutrophilic pustular dermatitis with intralesional cocci and acantholytic keratinocytes, consistent with superficial pyoderma, will be monitored by histopathology. Isolates from pustules of all dogs will be obtained to ascertain if the infection is from the inoculating strain of Staphylococcus pseudintermedius, and to determine effectiveness of antibody treatment. The results will be replicated in all dogs after a wash out period of several weeks. See Bäumer et al., Establishing a canine superficial pyoderma model, Journal of Applied Microbiology, 2017, 122(2): 331-337.

Example 11. Generation of Additional Anti-Protein A Antibodies

Additional anti-Protein A antibodies were obtained as described above in Example 1. The antibody heavy chain constant regions are human IgG1 Fc regions having amino acid substitutions of H at EU position 435 with an R (H435R), or a substitution of Y at EU position 436 with an F (Y436F), or a substitution of H435R and Y436F. The */* mutations were introduced into the expression vectors used to generate the fully human anti-Protein A antibodies, provided in Table 15.

Table 15 provides the amino acid sequence identifiers of the heavy and light chain variable regions and CDRs of selected antibodies provided herein. The corresponding nucleic acid sequence identifiers are provided in Table 16. Table 17 provides the full length heavy and light chain sequence identifiers for two anti-Protein A antibodies.

TABLE 15

Amino Acid Sequence Identifiers

| Antibody Designation | SEQ ID NOs: | | | | | | | |
| --- | --- | --- | --- | --- | --- | --- | --- | --- |
| | HCVR | HCDR1 | HCDR2 | HCDR3 | LCVR | LCDR1 | LCDR2 | LCDR3 |
| H1xH15135P*/* | 60 | 62 | 64 | 66 | 68 | 70 | 72 | 74 |
| H1xH15120P*/* | 80 | 82 | 84 | 86 | 88 | 90 | 72 | 93 |

TABLE 16

| | Nucleic Acid Sequence Identifiers | | | | | | | |
|---|---|---|---|---|---|---|---|---|
| Antibody | SEQ ID NOs: | | | | | | | |
| Designation | HCVR | HCDR1 | HCDR2 | HCDR3 | LCVR | LCDR1 | LCDR2 | LCDR3 |
| H1xH15135P*/* | 59 | 61 | 63 | 65 | 67 | 69 | 71 | 73 |
| H1xH15120P*/* | 79 | 81 | 83 | 85 | 87 | 89 | 91 | 92 |

TABLE 17

Sequence Identifiers for full length heavy and light chain sequences for H1xH15120P and H1xH15135P mutated forms (*/*)

| | SEQ ID NOs: | | | |
|---|---|---|---|---|
| | Full length Heavy Chain | | Full length Light Chain | |
| Antibody Designation | Nucleic Acid | Amino Acid | Nucleic Acid | Amino Acid |
| H1xH15135P*/* | 75 | 76 | 77 | 78 |
| H1xH15120P*/* | 94 | 95 | 96 | 97 |

Example 12. Biacore Binding Kinetics of Anti-Protein a Antibodies Binding to Protein a Measured at 25° C. and 37° C.

The equilibrium dissociation constants ($K_D$) of Protein A reagents binding to purified anti-Protein A monoclonal antibodies were determined using real-time surface plasmon resonance based Biacore T200. All binding studies were performed in 10 mM HEPES, 150 mM NaCl, 3.4 mM EDTA and 0.05% v/v Tween-20, pH 7.4 (HBS-EP) running buffer at 25° C. and 37° C. The Biacore CM5 sensor chip surface was first derivatized by amine coupling with anti-human Fc fragment specific F(ab')2 polyclonal antibody (Jackson Cat #109-006-008) to capture anti-Protein A monoclonal antibody. Binding studies were performed using different concentrations of Protein A (Calbiochem, 539202-5MG; 100 nM-0.39 nM; 4-fold serial dilution) prepared in HBS-EP running buffer. Proteins were injected over the captured anti-Protein A monoclonal antibody surface for 3.5 minutes at a flow rate of 504/minute, while the dissociation of Protein A reagents bound to monoclonal antibodies was monitored for 10 minutes in HBS-EP running buffer. The association rate ($k_a$) and dissociation rate ($k_d$) were determined by fitting the real-time binding sensorgrams to a 1:1 binding model with mass transport limitation using Scrubber 2.0c curve-fitting software. Binding dissociation equilibrium constant ($K_D$) and dissociative half-life (t½) were calculated from the kinetic rates as:

$$K_D(M) = \frac{kd}{ka}, \text{ and } t1/2(\min) = \frac{\ln(2)}{60 * kd}$$

Kinetic binding parameters for Protein A binding to anti-Protein A*/* monoclonal antibodies provided herein at 25° C. and 37° C. are shown in Tables 18 and 19. At 25° C., anti-Protein A*/* monoclonal antibodies bound to Protein A with a $K_D$ range value of 18 pM-444 pM, as shown in Table 18. At 37° C., anti-Protein A*/* monoclonal antibodies bound to Protein A with a $K_D$ range value of 14.1 pM-330 pM, as shown in Table 19.

TABLE 18

Kinetic binding parameters of Protein A binding to anti-Protein A*/* monoclonal antibody at 25° C.

| | | 100 nM | | | | |
|---|---|---|---|---|---|---|
| mAb Captured | mAb Capture Level (RU) | Ag Bound (RU) | $k_a$ (1/Ms) | $k_d$ (1/s) | $K_D$ (M) | t½ (min) |
| H1xH15120P*/* | 146 ± 2.8 | 69 | 1.25E+06 | 2.24E−05 | 1.80E−11 | 514.7 |
| H1xH15135P*/* | 127 ± 0.4 | 53 | 1.06E+06 | 4.71E−04 | 4.44E−10 | 24.5 |

TABLE 19

Kinetic binding parameters of Protein A binding to anti-Protein A*/* monoclonal antibody at 37° C.

| | | 100 nM | | | | |
|---|---|---|---|---|---|---|
| mAb Captured | mAb Capture Level (RU) | Ag Bound (RU) | $k_a$ (1/Ms) | $k_d$ (1/s) | $K_D$ (M) | t½ (min) |
| H1xH15120P*/* | 88 ± 4 | 40 | 1.84E+06 | 2.61E−05 | 1.41E−11 | 443.2 |
| H1xH15135P*/* | 50 ± 0.8 | 29 | 1.76E+06 | 5.82E−04 | 3.30E−10 | 19.8 |

Example 13: S. aureus ELISA to Assess the Specificity of Antibody Binding in the Presence of Protein A S. aureus expresses an IgG binding protein called Protein A on the pathogen's surface. Protein A contains 4-5 repeats of an IgG binding domain that has a high affinity for the Fc portion of human IgG1, IgG2, and IgG4 antibodies. See Loghem et al., 1982, staphylococcal Protein A and Human IgG subclasses and Allotypes, Scand. J. Immunol. 15: 275-278. Human IgG3 antibodies have amino acid substitutions that result in greatly diminished Protein A binding (H435R, Y436F, referred to as */*). Anti-Protein A hIgG1*/* monoclonal antibodies should have both specificity for Protein A through CDRs and avoid non-specific Fc driven binding through Fc modification.

Anti-Protein A hIgG1*/* antibodies were assessed for binding to S. aureus Newman wild-type strain to characterize the specificity of antibody binding in the presence of Protein A. S. aureus culture were grown overnight in TSB, washed twice with PBS and then resuspended at an OD=0.5 ($1.25 \times 10^8$ cfu/mL). Black Nunc microtiter plates were coated with 100 uL/well of the S. aureus suspension and incubated overnight at 4° C. The following morning, plates were washed three times with Assay Diluent Buffer (ADB, 1% BSA in PBS) and blocked for two hours with 200 ul of blocking buffer (3% BSA+0.5% Tween 20 in PBS) at room temperature. Next, plates were washed three times with ADB and then incubated with the primary antibody at the indicated concentration at room temperature for one hour. Secondary antibody (goat anti-human HRP; Thermofisher) was added at a 1:4000 dilution and incubated for one hour, after which plates were washed three times with ADB. Pico substrate was added for ten minutes and plates were read on a plate reader (Victor 3) to measure luminescent signal.

The three anti-Protein A hIgG1*/* antibodies bound to S. aureus wild-type Newman with sub-nM $EC_{50}$s, while the isotype control hIgG1*/* antibody (Anti-CD28) had minimal binding. See Table 20. These data indicate that anti-Protein A hIgG1*/* antibodies bind primarily through the antibody CDRs and that non-specific Fc dependent binding is eliminated through modification of hIgG1 with */* residues.

TABLE 20

| | S. aureus binding ELISA with anti-Protein A hIgG1*/* format antibodies |
|---|---|
| Antibody | $EC_{50}$ ELISA binding in log[M] S. aureus Newman WT |
| H1xH15120P*/* | 2.797E−10 |
| H1xH15135P*/* | 2.154E−10 |
| H1xH15140P*/* | 9.059E−11 |
| Isotype Control (H1xH14186P27*) | No Binding |

Example 14: ELISA to Assess the Specificity of Antibody Binding to S. aureus, S. intermedius, and S. pseudintermedius Pyoderma is an infection of dogs that is caused by Staphylococcus intermedius and pseudintermedius. Like S. aureus, these strains express 1-2 IgG binding proteins that are Protein A homologs called SpsQ and SpsP (See Balachandran, et al., 2018, Expression and Function of Protein A in Staphylococcus pseudintermedius. Virulence, 9(1): 390-401; Abouelkhair, et al., 2018, Characterization of Recombinant Wild-type and Nontoxigenic Protein A from Staphylococcus pseudintermedius. Virulence, 9(1): 1050-1061). Because of the sequence relatedness, the antibodies were assessed for binding to S. intermedius and S. pseudintermedius strains.

Anti-Protein A hIgG1*/* antibodies of this invention were assessed for binding to S. aureus Newman, Staphylococcus intermedius 27369, MRSP Staphylococcus pseudintermedius 88493 (methicillin-resistant) and Staphylococcus pseudintermedius AHDRCC 98200 strains. S. aureus cultures were grown overnight in RPMI, washed twice with PBS and then resuspended at an OD=0.5 ($1.25 \times 10^8$ cfu/mL). Black Nunc microtiter plates were coated with 100 uL/well of the staphylococcal suspension and incubated overnight at 4° C. The following morning, plates were washed three times with wash buffer (1% tween20+PBS) and blocked for two hours with 200 ul of blocking buffer (3% BSA+0.5% Tween 20 in PBS) at room temperature. Next, plates were washed three times with wash buffer and then incubated with the primary antibody at the indicated concentration at room temperature for one hour. Secondary antibody (chicken anti-human HRP) was added at a 1:4000 dilution and incubated for one hour, after which plates were washed three times with wash buffer. Pico substrate was added for ten minutes and plates were read on a plate reader (Spectromax) to measure luminescent signal.

As shown in Table 21, the Staphylococcus aureus, intermedius, and pseudintermedius strains grown in RPMI bound to a hIgG1 format isotype control, but only weakly to the same isotype control in a hIgG1*/* format, indicating expression of an IgG1 binding protein with specificity similar to Protein A on the bacterium's surface. Two anti-Protein A hIgG1*/* monoclonal antibodies, H1xH15120P and H1xH15135P, bound to the Staphylococcus aureus, intermedius, and pseudintermedius strains tested, while H1xH15140P only bound to the S. aureus Newman strain with signal above background.

TABLE 21

Staphylococcal binding ELISA with anti-Protein A hIgG1*/* format antibodies

|  | Antibody [M] | H1xH15120P hIgG1*/* | H1xH15135P hIG1*/* | H1xH15140P hIgG1*/* | REGN4440 hIgG1*/* isotype control | REGN1932 hIgG1 isotype control |
|---|---|---|---|---|---|---|
| S. intermedius 27369 | 3.09E−07 | 1.02E+05 | 5.09E+05 | 2.10E+04 | 1.11E+04 | 1.23E+05 |
|  | 3.86E−08 | 8.64E+04 | 1.40E+05 | 8.31E+03 | 3.85E+03 | 3.48E+04 |
|  | 4.82E−09 | 5.04E+04 | 2.43E+04 | 3.03E+03 | 2.49E+03 | 4.21E+04 |
|  | 6.03E−10 | 2.82E+04 | 7.12E+03 | 3.34E+03 | 3.01E+03 | 5.30E+03 |
|  | 7.54E−11 | 1.10E+04 | 3.38E+03 | 2.66E+03 | 2.51E+03 | 2.68E+03 |
|  | 9.42E−12 | 3.46E+03 | 1.38E+03 | 1.52E+03 | 7.75E+02 | 1.61E+03 |
|  | 1.18E−12 | 2.73E+03 | 2.58E+03 | 2.46E+03 | 2.21E+03 | 9.74E+03 |
|  | 1.47E−13 | 1.04E+03 | 1.16E+03 | 1.51E+03 | 8.96E+02 | 2.53E+04 |
| S. pseudintermedius 98200 | 3.09E−07 | 1.58E+05 | 7.15E+05 | 2.06E+04 | 1.52E+04 | 1.32E+05 |
|  | 3.86E−08 | 1.48E+05 | 2.37E+05 | 6.68E+03 | 5.10E+03 | 3.64E+04 |
|  | 4.82E−09 | 8.36E+04 | 3.90E+04 | 3.40E+03 | 2.41E+03 | 8.04E+03 |
|  | 6.03E−10 | 3.92E+04 | 9.35E+03 | 4.89E+03 | 2.76E+03 | 4.77E+03 |
|  | 7.54E−11 | 1.18E+04 | 7.63E+03 | 4.68E+03 | 2.24E+03 | 2.59E+03 |
|  | 9.42E−12 | 4.24E+03 | 1.32E+04 | 2.48E+03 | 1.17E+03 | 1.46E+03 |
|  | 1.18E−12 | 3.35E+03 | 5.96E+03 | 5.02E+03 | 2.17E+03 | 2.83E+03 |
|  | 1.47E−13 | 2.97E+03 | 6.22E+03 | 3.94E+03 | 1.12E+03 | 1.48E+03 |
| S. pseudintermedius 88493 | 3.09E−07 | 2.61E+04 | 4.84E+04 | 1.07E+04 | 1.47E+04 | 4.39E+04 |
|  | 3.86E−08 | 1.33E+04 | 9.50E+04 | 6.36E+03 | 6.47E+03 | 1.45E+04 |
|  | 4.82E−09 | 7.97E+03 | 1.72E+04 | 5.97E+03 | 7.36E+03 | 8.95E+03 |
|  | 6.03E−10 | 7.51E+03 | 8.80E+03 | 1.00E+04 | 7.08E+03 | 1.10E+04 |
|  | 7.54E−11 | 8.92E+03 | 6.40E+03 | 5.41E+03 | 6.37E+03 | 7.56E+03 |
|  | 9.42E−12 | 3.88E+03 | 3.64E+03 | 4.27E+03 | 6.15E+03 | 7.98E+03 |
|  | 1.18E−12 | 5.43E+03 | 5.91E+03 | 5.99E+03 | 6.71E+03 | 8.92E+03 |
|  | 1.47E−13 | 4.35E+03 | 3.86E+03 | 3.47E+03 | 1.23E+04 | 8.19E+03 |
| S. aureus Newman | 3.09E−07 | 9.17E+05 | 1.15E+06 | 9.79E+05 | 3.88E+04 | 5.06E+05 |
|  | 3.86E−08 | 8.15E+05 | 1.07E+06 | 8.38E+05 | 2.76E+04 | 4.34E+05 |
|  | 4.82E−09 | 8.20E+05 | 1.02E+06 | 8.28E+05 | 1.94E+04 | 6.52E+05 |
|  | 6.03E−10 | 7.43E+05 | 6.89E+05 | 6.47E+05 | 2.75E+04 | 5.09E+05 |
|  | 7.54E−11 | 4.47E+05 | 2.41E+05 | 2.38E+05 | 2.44E+04 | 2.53E+05 |
|  | 9.42E−12 | 1.18E+05 | 5.02E+04 | 6.05E+04 | 1.67E+04 | 7.25E+04 |
|  | 1.18E−12 | 1.71E+05 | 4.23E+04 | 2.84E+04 | 1.71E+04 | 3.02E+04 |
|  | 1.47E−13 | 2.72E+04 | 2.28E+04 | 2.20E+04 | 1.55E+04 | 1.86E+04 |

Example 15: Anti-Protein A hIgG1*/* Blocking of Fc Binding to S. aureus, as Shown by Flow Cytometry Three exemplary anti-Protein A hIgG1*/* antibodies were evaluated for the ability to block interactions between a fluorescently labeled Fc fragment and wild-type S. aureus expressing Protein A. S. aureus wild-type and Protein A deficient (Δspa) strains were grown overnight in TSB, washed twice with PBS, and diluted to a final concentration of 1×10$^7$ cfu/mL in PBS. The bacteria were then fixed with 2% paraformaldehyde for 30 minutes at room temperature, after which they were washed three times with PBS, resuspended in blocking buffer (3% BSA in PBS) and incubated at room temperature for two hours. Following blocking, the bacteria were washed once and resuspended in 200 uL of the indicated blocking antibody at either 10 ug/mL or 1 ug/mL in 1% BSA in PBS and incubated at 37° C. for 30 minutes. Next, bacteria were washed three times with PBS and resuspended in 1% BSA in PBS with Alexa-488 labeled Fc fragment at 5 ug/mL and incubated for 30 minutes at 37° C. Finally, bacteria were washed three times with PBS and resuspended in PBS at a final volume of 200 uL and fluorescent signal was measured via flow cytometry (Guava Millipore Easycyte).

An alexa-488 labeled IgG1 Fc fragment bound wild-type S. aureus expressing Protein A (geomean fluorescent signal=1850), but only minimally to a Protein A deficient strain (Δspa, geomean fluorescent signal=12), showing the requirement of Protein A for Fc binding to the bacterium. These controls were used to normalize Fc binding measurements of wild-type S. aureus pretreated with anti-Protein A antibodies at 10 ug/mL and 1 ug/mL. As shown in Table 22, H1xH15120P blocked >90% of Fc binding to S. aureus at both concentrations, H1xH15140P blocked >75% of Fc binding at both concentrations, and H1xH15135P blocked >60% of Fc binding to S. aureus at both concentrations. These data demonstrate that anti-Protein A hIgG1*/* antibodies can block Fc binding to S. aureus.

TABLE 22

Anti-Protein A hIgG1*/* blocking of Fc binding to S. aureus

| Antibody | Fc: S. aureus blocking activity (%) | |
|---|---|---|
|  | 10 ug/mL | 1 ug/mL |
| S. aureus wild-type (no antibody control) | 0 | 0 |
| S. aureus Δspa (no antibody control) | 100 | 100 |
| Isotype control (H1xH14186P2*/*) | −13 | −5 |
| H1xH15120P*/*-L1 | 99 | 90 |
| H1xH15135P*/*-L1 | 66 | 62 |
| H1xH15140P*/*-L1 | 97 | 78 |

Example 16: Anti-Protein A hIgG1*/* Blocking of V$_H$3 Driven Antibody Binding to S. aureus In addition to Fc binding, Protein A has the ability to bind to the Fab region of IgG, IgM, IgA and IgE antibodies through a region sometimes referred to as the "alternative binding site." See Inganas, 1981, Comparison of mechanisms of interaction between protein A from *Staphylococcus aureus* and human monoclonal IgG, IgA and IgM in relation to the classical FC gamma and the alternative F(ab')2 epsilon protein A interactions. Scand J Immunol, 13(4): 343-52. It was subsequently found that Fab binding activity was restricted to antibodies containing $V_H3$ family heavy chain variable regions. See Sasso, et al., 1989, Human IgM molecules that bind staphylococcal protein A contain VHIII H chains. J Immunol, 142(8): 2778-83. Through binding to $V_H3$ family antibodies, *S. aureus* can cluster surface receptors on immune cells with potentially deleterious outcomes, for example B cell receptor clustering resulting in non-specific B cell activation or IgE clustering inducing activation of basophils. See Silverman, 1992, Human antibody responses to bacterial antigens: studies of a model conventional antigen and a proposed model B cell superantigen, Int Rev Immunol, 9(1): 57-78; Marone, et al., 1987, Mechanism of activation of human basophils by *Staphylococcus aureus* Cowan 1. Infect Immun, 55(3): 803-9. Monoclonal antibodies with specificity for Protein A could have the potential to block interactions between the Fab of $V_H3$ antibodies and *S. aureus* expressing Protein A and prevent non-specific immune cell activation.

Three anti-Protein A hIgG1*/* antibodies were evaluated for the ability to block interactions between a fluorescently labeled $V_H3$ lineage antibody and wild-type *S. aureus* expressing Protein A. The labeled $V_H3$ lineage antibody (Anti-PD1 hIgG1*/* Fc**-488) contained */* residues (H435R, Y436F), so that Fc driven binding to Protein A was ablated and only $V_H3$ driven binding remained. *S. aureus* wild-type and Protein A deficient (Δspa) strains were grown overnight in TSB, washed twice with PBS, and diluted to a final concentration of 1×10$^7$ cfu/mL in PBS. The bacteria were then fixed with 2% paraformaldehyde for 30 minutes, after which they were washed three times with PBS and resuspended in blocking buffer (3% BSA in PBS) and incubated at room temperature for two hours. Following blocking, the bacteria were washed once with PBS and resuspended in 200 uL of the indicated blocking antibody at either 10 ug/mL or 1 ug/mL in 1% BSA in PBS and incubated at 37° C. for 30 minutes. Next, bacteria were washed three times with PBS and resuspended in Alexa-488 labeled $V_H3$ lineage hIgG1*/* antibody at 5 ug/mL in 1% BSA in PBS and incubated for 30 minutes at 37° C. Finally, bacteria were washed three times with PBS and resuspended in PBS at a final volume of 200 uL and fluorescent signal was measured via flow cytometry (Guava Millipore Easycyte).

An alexa-488 labeled $V_H3$ hIgG1*/* antibody bound wild-type *S. aureus* expressing Protein A (geomean fluorescent signal=273), but only minimally to a Protein A deficient strain (Δspa, geomean fluorescent signal=10.5), showing the requirement of Protein A for $V_H3$ antibody binding to the bacterium. These controls were used to normalize $V_H3$ antibody binding measurements of wild-type *S. aureus* pretreated with anti-Protein A antibodies at 10 ug/mL and 1 ug/mL. As shown in Table 23, the three anti-Protein A hIgG1*/* antibodies were able to block >80% of $V_H3$ antibody binding to *S. aureus* at both anti-Protein A concentrations. These data demonstrate that anti-Protein A hIgG1*/* antibodies can block $V_H3$ driven binding to *S. aureus*, suggesting that they could be used to prevent deleterious immune cell receptor clustering, such as B cell superantigen activity or basophil degranulation.

TABLE 23

Anti-Protein A hIgG*/* blocking of VH3 driven antibody binding to *S. aureus*

| Antibody | VH3 antibody: *S. aureus* blocking activity (%) | |
|---|---|---|
| | 10 ug/mL | 1 ug/mL |
| *S. aureus* wild-type (no antibody control) | 0 | 0 |
| *S. aureus* Δspa (no antibody control) | 100 | 100 |
| Isotype control (H1xH14186P2*/*) | 46.1 | 36.2 |
| H1xH15120P*/*-L1 | 96.1 | 95.0 |
| H1xH15135P*/*-L1 | 84.4 | 89.8 |
| H1xH15140P*/*-L1 | 84.7 | 84.5 |

Example 17. *S. aureus* Survival in Complement Preserved Serum and Antibody-Induced Killing by hIgG*/* Antibodies As noted previously, *S. intermedius* and *S. pseudintermedius*, which are the causative agents of pyoderma in dogs, express 1-2 IgG binding proteins that are Protein A homologs and these homologs are called SpsQ and SpsP (See Balachandran, M., D. A. Bemis, and S. A. Kania, Expression and function of protein A in *Staphylococcus pseudintermedius*. Virulence, 2018. 9(1): p. 390-401; Abouelkhair, M. A., D. A. Bemis, and S. A. Kania, Characterization of recombinant wild-type and nontoxigenic protein A from *Staphylococcus pseudintermedius*. Virulence, 2018. 9(1): p. 1050-1061).

Because of the sequence relatedness between SpsQ, SpsP and Protein A, an antibody of this invention (H1xH15120P), which was able to bind *S. intermedius* and *S. pseudintermedius* strains, was assessed for its ability to induce serum killing. The serum induced killing was compared to that of another anti-Protein A monoclonal antibody, H1xH15140P, which lacked binding to *S. intermedius* and *S. pseudintermedius* strains and was used as a control in this study.

More specifically, anti-Protein A hIgG1*/* antibodies of this invention were assessed for their ability to promote killing of staphylococcal strains *S. aureus* Newman, *S. intermedius* 27369 and *S. pseudintermedius* AHDRCC 98200 in normal human serum. Briefly, a culture of Staphylococci was grown in RPMI overnight, washed in PBS, and resuspended in RPMI+0.05% BSA to a concentration of 1×10$^5$ colony forming units (CFU)/mL. Normal human serum (NHS) was thawed in a 37° C. water bath and then kept on ice. In triplicate, 100 uL of the *S. aureus* suspension was mixed with test antibody and 100 uL of normal human serum was added for a final concentration of 50% serum and 10 ug/mL, 30 ug/mL, 90 ug/mL or 270 ug/mL monoclonal antibody. The test samples were then incubated shaking (100 rpm) at 37° C. for 16 hours. After incubation, 100 uL of agglutination lysis buffer (PBS supplemented with 200U Streptokinase, 2 ug/mL RNase, 10 ug/mL DNase, 0.5% saponin per ml of PBS) was added to the samples, vigorously vortexed and incubated at 37° C. for 10 minutes. Staphylococcal survival was enumerated by colony forming units through serial dilution and plating onto TSA.

Results from a representative experiment are in Table 24. The isotype control antibody had minimal impact on viability of *S. aureus*, *S. intermedius*, and *S. pseudintermedius* strains at the highest concentration tested (270 ug/ml). Antibodies H1xH15140P*/* and H1xH15120P*/* induced dose dependent killing of *S. aureus* Newman in human serum. H1xH15120P*/*, but not H1xH15140P*/*, induced more than 90% serum killing of *S. intermedius* and *S.*

*pseudintermedius* at the highest concentration tested (270 ug/mL). The ability to induce serum killing correlates with ELISA binding data, where both H1xH15140P*/* and H1xH15120P*/* bind to *S. aureus* Newman, while H1xH15120P*/*, but not H1xH15140P*/*, binds well to *S. intermedius* and *S. pseudintermedius*.

TABLE 24

Antibody induced killing of *S. aureus* Newman, *S. pseudintermedius* AHDRCC 98200 and *S. intermedius* 27369 in human serum with anti-Protein A*/* monoclonal antibody treatment

| | [mAb] ug/mL | *S. intermedius* 27369 median cfu/mL | Standard Deviation | *S. pseudintermedius* AHDRCC 98200 median cfu/mL | Standard Deviation | *S. aureus* Newman median cfu/mL | Standard Deviation |
|---|---|---|---|---|---|---|---|
| Staphylococci + Serum | (−) | 7.8E+06 | 5.0E+05 | 8.3E+06 | 1.8E+06 | 9.5E+06 | 1.3E+06 |
| REGN4440 hIgG1*/* Isotype Control | 270 | 8.0E+06 | 9.0E+05 | 7.5E+06 | 6.6E+05 | 7.0E+06 | 1.8E+06 |
| H1xH15140P*/* | 10 | 6.0E+06 | 1.1E+06 | 7.3E+06 | 5.0E+05 | 4.3E+06 | 5.2E+05 |
| | 30 | 8.3E+06 | 8.8E+05 | 6.8E+06 | 1.2E+06 | 1.0E+06 | 9.0E+04 |
| | 90 | 8.5E+06 | 1.2E+06 | 6.8E+06 | 2.4E+06 | 6.0E+05 | 2.9E+04 |
| | 270 | 3.8E+06 | 2.0E+06 | 4.5E+06 | 1.3E+06 | 1.8E+05 | 2.9E+04 |
| H1xH15120P*/* | 10 | 9.0E+06 | 2.0E+06 | 5.8E+06 | 2.0E+06 | 9.0E+06 | 5.2E+05 |
| | 30 | 6.3E+06 | 1.2E+06 | 4.8E+06 | 1.9E+06 | 5.0E+06 | 1.0E+06 |
| | 90 | 5.3E+06 | 2.0E+06 | 2.3E+06 | 1.1E+06 | 3.5E+06 | 8.8E+05 |
| | 270 | 5.0E+05 | 1.3E+05 | 7.8E+05 | 5.0E+04 | 6.5E+05 | 1.8E+05 |

Example 18. Heavy and Light Chain Variable Region Amino Acid and Nucleic Acid Sequences of Exemplary Anti-IsdA*/* Antibody and Anti-IsdB*/* Antibody Table 25 provides the amino acid sequence identifiers of the heavy and light chain variable regions and CDRs of selected antibodies provided herein. The corresponding nucleic acid sequence identifiers are provided in Table 26. Table 27 provides the full length heavy and light chain sequence identifiers for one anti-IsdA antibody and one anti-IsdB antibody, both with the */* heavy chain mutations.

TABLE 25

Amino Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H1xH20207P*/* (anti-IsdA) | 99 | 101 | 103 | 105 | 107 | 109 | 111 | 113 |
| H1xH20286P*/* (anti-Isd B) | 119 | 121 | 123 | 125 | 127 | 129 | 131 | 133 |

TABLE 26

Nucleic Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H1xH20207P*/* (anti-IsdA) | 98 | 100 | 102 | 104 | 106 | 108 | 110 | 112 |
| H1xH20286P*/* (anti-IsdB) | 118 | 120 | 122 | 124 | 126 | 128 | 130 | 132 |

TABLE 27

Sequence Identifiers for full length heavy and light chain
sequences for H1xH20207P (*/*) and H1xH20286P (*/*)

| Antibody Designation | SEQ ID NOs: | | | |
|---|---|---|---|---|
| | Full length Heavy Chain | | Full length Light Chain | |
| | Nucleic Acid | Amino Acid | Nucleic Acid | Amino Acid |
| H1xH20207P*/* (anti-IsdA) | 114 | 115 | 116 | 117 |
| H1xH20286P*/* (anti-IsdB) | 134 | 135 | 136 | 137 |

The antibodies provided herein can be of any isotype as long as the immunoglobulin heavy chain differs from that of an unmodified parent anti-S. aureus IgG antibody by at least two amino acid substitutions: H435R and Y436F, by EU index numbering. The mutated form of the IgG1 having the two amino acid substitutions H435R and Y436F is referred to throughout this disclosure as */*. Anti-IsdA*/* and anti-IsdB*/* antibodies provided herein may comprise variable domain and CDR sequences as set forth in Tables 25 and 26 and a human Fc domain of isotype IgG1 having the H435R and Y436F mutations according to SEQ ID NO: 58. For certain applications or experiments the Fc domain may be a mouse Fc domain. As will be appreciated by a person of ordinary skill in the art, an antibody having a particular Fc isotype can be converted to an antibody with a different Fc isotype having the equivalent H435R and Y436F mutations (e.g., an antibody with a mouse IgG3 Fc can be converted to an antibody with a human IgG1*/*, etc.), but in any event, the variable domains (including the CDRs)—which are indicated by the numerical identifiers shown in Tables 25 and 26—will remain the same, and the binding properties are expected to be identical or substantially similar regardless of the nature of the Fc domain in as much as the H435R and Y436F mutations are present.

Example 19: *S. aureus* Survival in Complement Preserved Serum and Antibody-Induced Killing by hIgG1*/* Monoclonal Antibodies Like Examples 5 and 7, antibodies in this experiment were tested for their ability to overcome *S. aureus* complement evasion and initiate antibody-induced serum killing of the *S. aureus* strain MSSA Newman.

Anti-Protein A, IsdA and IsdB hIgG1*/* antibodies disclosed herein were assessed for their ability to promote killing of *S. aureus* Newman in normal human serum. Briefly, a culture of *S. aureus* Newman was grown in RPMI overnight, washed in PBS, and resuspended in RPMI+ 0.05% BSA to a concentration of $1 \times 10^5$ colony forming units (CFU)/mL. Normal human serum complement (NHS) was thawed in a 37° C. water bath and then kept on ice. In triplicate, 100 uL of the *S. aureus* suspension was mixed with test antibody and 100 uL of the indicated serum was added for a final concentration of 50% serum and 200 ug/mL monoclonal antibody. The test samples were then incubated shaking (100 rpm) at 37° C. for 16h. After incubation, 100 uL of agglutination lysis buffer (PBS supplemented with 200U Streptokinase and 0.5% saponin per ml of PBS) was added to the samples, vigorously vortexed and incubated at 37° C. for 10 minutes. *S. aureus* survival was enumerated by colony forming units through serial dilution and plating onto TSA.

Figure 8:
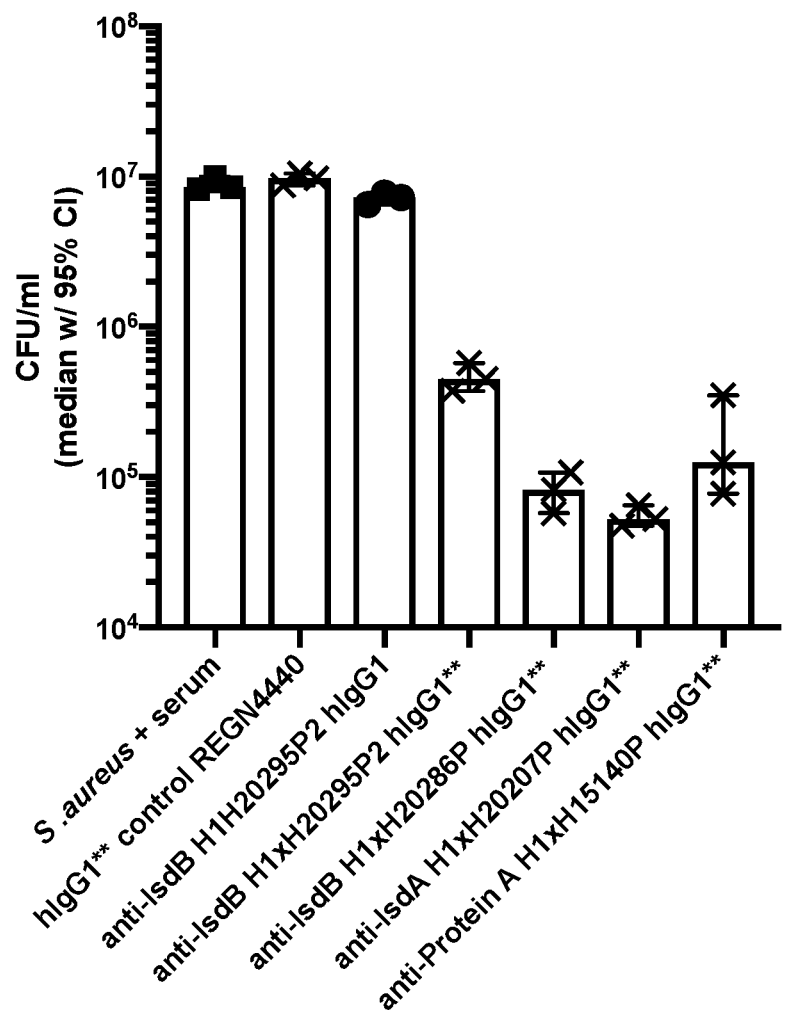

Results from a representative experiment are shown in Table 28 and FIG. 8. The hIgG1*/* control and anti-IsdB hIgG1 format monoclonal antibodies did not impact survival of *S. aureus* strains in NHS. However, the anti-IsdB hIgG1*/* monoclonal antibodies H1xH20295P2 and H1xH20286P, anti-IsdA hIgG1*/* monoclonal antibody H1xH20207P, and anti-Protein A hIgG1*/* monoclonal antibody H1xH15140P had serum bactericidal activity over 16 hours, with a decrease in *S. aureus* viability of ~1-2 logs.

TABLE 28

*S. aureus* MSSA Newman Survival in Human Serum with Anti-IsdB, anti-IsdA, and anti-Protein A */* Antibody Treatment

| Antibody (200 ug/mL) 16 hour incubation | *S. aureus* Newman | |
|---|---|---|
| | median cfu/mL | standard deviation |
| *S. aureus* + serum | 8.50E+06 | 9.46E+05 |
| hIgG1*/* control (REGN4440) | 9.75E+06 | 8.78E+05 |
| anti-IsdB hIgG1 (H1H20295P2) | 7.25E+06 | 6.29E+05 |
| anti-IsdB hIgG1*/* (H1xH20295P2) | 4.50E+05 | 1.01E+05 |
| anti-IsdB hIgG1*/* (H1xH20286P) | 8.25E+04 | 2.50E+04 |
| anti-IsdA hIgG1*/* (H1xH20207P) | 5.25E+04 | 9.01E+03 |
| anti-Protein A hIgG1*/* (H1xH15140P) | 1.25E+05 | 1.46E+05 |

Example 20: Testing Anti-IsdB and Anti-Protein A hIgG1 and hIgG1*/* Formatted Antibodies in a *S. aureus* Disseminated Infection Model Using the same *S. aureus* disseminated infection model mentioned in Example 6, hIgG1*/* format anti-IsdB, IsdA, and Protein A antibodies were tested for their ability to decrease kidney burden when administered 1 day post *S. aureus* Newman infection.

Briefly, a culture of *S. aureus* Newman was grown in TSB overnight, subcultured and grown to mid-logarithmic phase (OD600=1). The culture was then washed in PBS twice and resuspended in PBS at an optical density of 3 ($7.5 \times 10^8$ cfu/mL). C57BL/6 mice were injected intraperitoneally with 200 uL of the bacterial suspension. At one day post infection, mice were treated with 10 mg/kg of the indicated monoclonal antibody in PBS in 100 uL administered subcutaneously. Mice were monitored for weight loss and body condition until 4 days post infection, at which point they were euthanized. Kidneys were removed and resuspended in 0.1% Triton X100 in PBS and homogenized using C-max dissociation tubes. Bacteria were enumerated by colony forming units through serial dilution and plating onto TSA.

Figure 9:
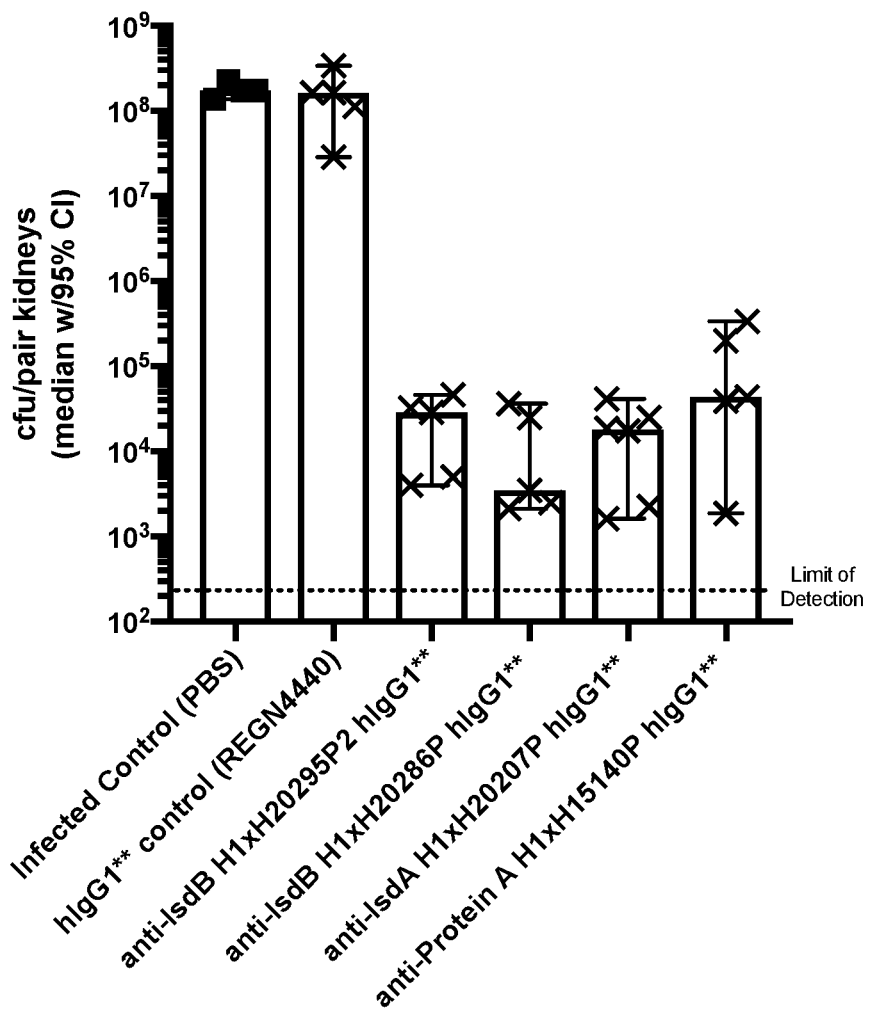

Results are presented in Table 29 and FIG. 9. The monoclonal antibodies H1xH20295P2, H1xH20286P, H1xH20207P, and H1xH15140P in a hIgG1*/* format reduced *S. aureus* kidney burden by 3-5 logs compared to untreated mice when dosed at 10 mg/kg at one day post-infection. The hIgG1*/* control treated group had similar kidney burden to untreated mice.

TABLE 29

S. aureus Kidney burden in antibody treated mice

| | median cfu/pair kidneys | standard deviation |
|---|---|---|
| Infected Control (PBS) | 1.8E+08 | 3.6E+07 |
| hIgG1*/* control (REGN4440) | 1.6E+08 | 1.1E+08 |
| anti-IsdB H1xH20295P2 hIgG1*/* | 2.9E+04 | 1.8E+04 |
| anti-IsdB H1xH20286P hIgG1*/* | 3.5E+03 | 1.6E+04 |
| anti-IsdA H1xH20207P hIgG1*/* | 1.8E+04 | 1.5E+04 |
| anti-Protein A H1xH15140P hIgG1*/* | 4.4E+04 | 1.4E+05 |

Example 21: Testing Anti-IsdA, Anti-IsdB, and Anti-Protein A hIgG1*/* Antibodies in Whole Blood Bacterial Survival Functional Assay S. aureus survival in whole human blood was assessed in an ex vivo assay to explore the role of complement and immune effector cells to induce S. aureus killing. See Thammavongsa et al., Staphylococcus aureus synthesizes adenosine to escape host immune responses. J Exp Med. 2009 Oct. 26; 206(11): 2417-27. The activity of anti-staphylococcal hIgG1*/* format monoclonal antibodies, anti-IsdB, anti-IsdA, and anti-Protein A antibodies, to promote antibody-induced killing of S. aureus Newman in whole blood was assessed at four hours post infection.

Fresh blood was obtained from five independent donors using sodium citrate as an anti-coagulant. In addition, prior to the experiment, an additional 500 nM dabigatran was added to prevent clot formation. A culture of S. aureus Newman was grown in phenol-free RPMI overnight, washed in PBS, and resuspended to a concentration of $1 \times 10^6$ colony forming units (CFU)/mL in PBS. A 100 uL master mix of bacteria and antibody was prepared by diluting the antibody in the bacterial suspension to 1 mg/mL. In triplicate, 10 uL master mix was added to 100 uL of human whole blood for a final concentration of 100 ug/mL of antibody and $1 \times 10^4$ CFU. The samples were incubated in 1.5 mL microcentrifuge tubes at 37° C. with shaking (600 rpm) for 4 hours. Following incubation, 100 uL of agglutination lysis buffer (PBS supplemented with 200 U Streptokinase and 5% saponin in PBS) was added to the samples, vigorously vortexed and incubated at 37 C and shaking for 5 minutes. S. aureus survival was enumerated by colony forming units through serial dilution and plating onto TSA.

Experiments were performed with blood from five independent donors. For each donor, treatment groups were normalized to the untreated control and expressed as percent S. aureus survival. Individual data points represent the median S. aureus survival from one donor.

Figure 10:
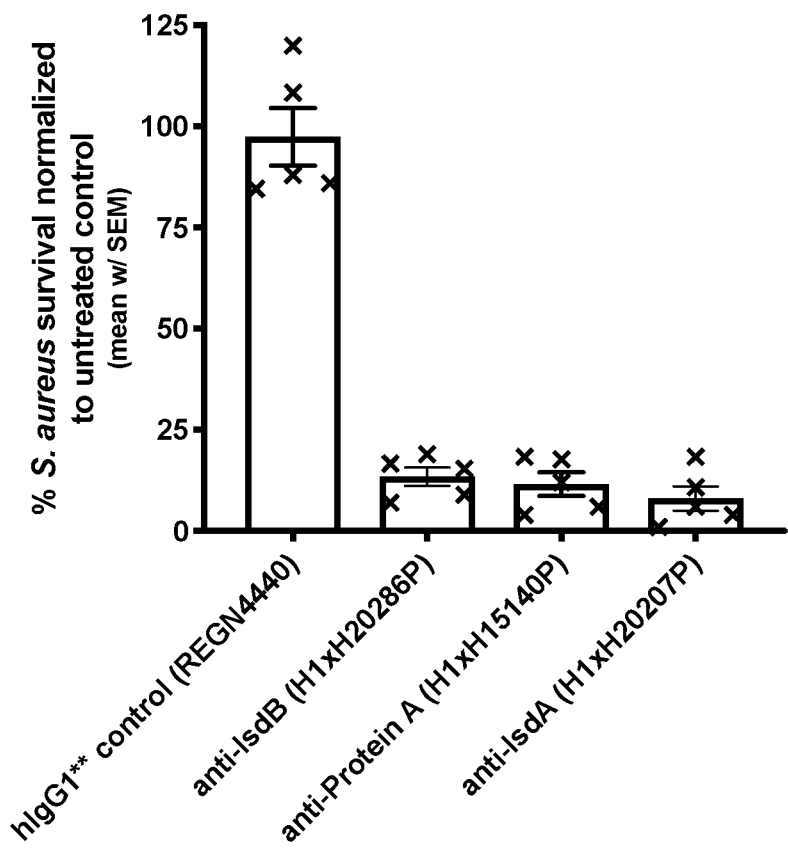

Results from five independent blood donors are shown in FIG. 10. The isotype control hIgG1*/* monoclonal antibody did not impact viability of S. aureus, however anti-Protein A, anti-IsdA and anti-IsdB hIgG1*/* monoclonal antibodies induced antibody-dependent killing of S. aureus in human blood.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. An isolated antibody or antigen-binding fragment thereof that specifically binds to *S. aureus* Protein A and comprises an HCVR/LCVR amino acid sequence pair as set forth in SEQ ID NOs: 18/26.

2. A pharmaceutical composition comprising an antibody of claim 1 and a pharmaceutically acceptable carrier or diluent.

3. The isolated antibody or antigen-binding fragment thereof of claim 1, wherein the antibody further comprises an hIgG1 Fc domain of SEQ ID NO: 58.

4. The isolated antibody or antigen-binding fragment thereof of claim 1, wherein the antibody or antigen-binding fragment thereof has attenuated IgG1 Fc binding to Protein A.

* * * * *

SEQUENCE LISTING

<160> NUMBER OF SEQ ID NOS: 137

<210> SEQ ID NO 1
<211> LENGTH: 369
<212> TYPE: DNA
<213> ORGANISM: Artificial Sequence
<220> FEATURE:
<223> OTHER INFORMATION: synthetic

<400> SEQUENCE: 1

```
gaagtgcagc tggtggagtc tgggggaggc ttggtacagc ctggcaggtc cctgagagtc      60
tcttgtgcag cctctggatt caccttttgat gattatgcca tgcactgggt ccggcaaatt     120
ccagggaagg gcctggagtg ggtctcaggt attagatgga atagtgacac tataggctat     180
gcggactctg tgaagggccg attcaccatt tccagagaca acgccaagaa ttttctatat     240
ctacaaatga acagtctgag aactgaagac acggccttat attactgtgt caaagatatg     300
agggttcggg gaattataat gtacggtatg gacgtctggg gccaagggac cacggtcacc     360
gtctcctca                                                              369
```

<210> SEQ ID NO 2
<211> LENGTH: 123
<212> TYPE: PRT
<213> ORGANISM: Artificial Sequence
<220> FEATURE:

<223> OTHER INFORMATION: synthetic

<400> SEQUENCE: 2

Glu Val Gln Leu Val Glu Ser Gly Gly Gly Leu Val Gln Pro Gly Arg
1               5                   10                  15

Ser Leu Arg Val Ser Cys Ala Ala Ser Gly Phe Thr Phe Asp Asp Tyr
            20                  25                  30

Ala Met His Trp Val Arg Gln Ile Pro Gly Lys Gly Leu Glu Trp Val
        35                  40                  45

Ser Gly Ile Arg Trp Asn Ser Asp Thr Ile Gly Tyr Ala Asp Ser Val
    50                  55                  60

Lys Gly Arg Phe Thr Ile Ser Arg Asp Asn Ala Lys Asn Phe Leu Tyr
65                  70                  75                  80

Leu Gln Met Asn Ser Leu Arg Thr Glu Asp Thr Ala Leu Tyr Tyr Cys
                85                  90                  95

Val Lys Asp Met Arg Val Arg Gly Ile Ile Met Tyr Gly Met Asp Val
            100                 105                 110

Trp Gly Gln Gly Thr Thr Val Thr Val Ser Ser
        115                 120

<210> SEQ ID NO 3
<211> LENGTH: 24
<212> TYPE: DNA
<213> ORGANISM: Artificial Sequence
<220> FEATURE:
<223> OTHER INFORMATION: synthetic

<400> SEQUENCE: 3
ggattcacct ttgatgatta tgcc                                          24

<210> SEQ ID NO 4
<211> LENGTH: 8
<212> TYPE: PRT
<213> ORGANISM: Artificial Sequence
<220> FEATURE:
<223> OTHER INFORMATION: synthetic

<400> SEQUENCE: 4

Gly Phe Thr Phe Asp Asp Tyr Ala
1               5

<210> SEQ ID NO 5
<211> LENGTH: 24
<212> TYPE: DNA
<213> ORGANISM: Artificial Sequence
<220> FEATURE:
<223> OTHER INFORMATION: synthetic

<400> SEQUENCE: 5
attagatgga atagtgacac tata                                          24

<210> SEQ ID NO 6
<211> LENGTH: 8
<212> TYPE: PRT
<213> ORGANISM: Artificial Sequence
<220> FEATURE:
<223> OTHER INFORMATION: synthetic

<400> SEQUENCE: 6

Ile Arg Trp Asn Ser Asp Thr Ile
1               5

<210> SEQ ID NO 7
<211> LENGTH: 48
<212> TYPE: DNA
<213> ORGANISM: Artificial Sequence
<220> FEATURE:
<223> OTHER INFORMATION: synthetic

<400> SEQUENCE: 7

```
gtcaaagata tgagggttcg gggaattata atgtacggta tggacgtc            48
```

<210> SEQ ID NO 8
<211> LENGTH: 16
<212> TYPE: PRT
<213> ORGANISM: Artificial Sequence
<220> FEATURE:
<223> OTHER INFORMATION: synthetic

<400> SEQUENCE: 8

Val Lys Asp Met Arg Val Arg Gly Ile Ile Met Tyr Gly Met Asp Val
1               5                   10                  15

<210> SEQ ID NO 9
<211> LENGTH: 324
<212> TYPE: DNA
<213> ORGANISM: Artificial Sequence
<220> FEATURE:
<223> OTHER INFORMATION: synthetic

<400> SEQUENCE: 9

```
gacatccaga tgacccagtc tccatcctcc ctgtctgcat ctgtaggaga cagagtcacc     60
atcacttgcc gggcaagtca gagcattagc agctatttaa attggtatca gcagaaacca    120
gggaaagccc ctaagctcct gatctatgct gcatccagtt tgcaaagtgg ggtcccgtca    180
aggttcagtg gcagtggatc tgggacagat ttcactctca ccatcagcag tctgcaacct    240
gaagattttg caacttacta ctgtcaacag agttacagta cccctccgat caccttcggc    300
caagggacac gactggagat taaa                                           324
```

<210> SEQ ID NO 10
<211> LENGTH: 108
<212> TYPE: PRT
<213> ORGANISM: Artificial Sequence
<220> FEATURE:
<223> OTHER INFORMATION: synthetic

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 11

```
<211> LENGTH: 18
<212> TYPE: DNA
<213> ORGANISM: Artificial Sequence
<220> FEATURE:
<223> OTHER INFORMATION: synthetic

<400> SEQUENCE: 11
cagagcatta gcagctat                                                 18

<210> SEQ ID NO 12
<211> LENGTH: 6
<212> TYPE: PRT
<213> ORGANISM: Artificial Sequence
<220> FEATURE:
<223> OTHER INFORMATION: synthetic

<400> SEQUENCE: 12

Gln Ser Ile Ser Ser Tyr
1               5

<210> SEQ ID NO 13
<211> LENGTH: 9
<212> TYPE: DNA
<213> ORGANISM: Artificial Sequence
<220> FEATURE:
<223> OTHER INFORMATION: synthetic

<400> SEQUENCE: 13 gctgcatcc                                                            9

<210> SEQ ID NO 14
<211> LENGTH: 3
<212> TYPE: PRT
<213> ORGANISM: Artificial Sequence
<220> FEATURE:
<223> OTHER INFORMATION: synthetic

<400> SEQUENCE: 14

Ala Ala Ser
1

<210> SEQ ID NO 15
<211> LENGTH: 30
<212> TYPE: DNA
<213> ORGANISM: Artificial Sequence
<220> FEATURE:
<223> OTHER INFORMATION: synthetic

<400> SEQUENCE: 15
caacagagtt acagtacccc tccgatcacc                                    30

<210> SEQ ID NO 16
<211> LENGTH: 10
<212> TYPE: PRT
<213> ORGANISM: Artificial Sequence
<220> FEATURE:
<223> OTHER INFORMATION: synthetic

<400> SEQUENCE: 16

Gln Gln Ser Tyr Ser Thr Pro Pro Ile Thr
1               5                   10

<210> SEQ ID NO 17
<211> LENGTH: 351
<212> TYPE: DNA
<213> ORGANISM: Artificial Sequence
<220> FEATURE:
```

<223> OTHER INFORMATION: synthetic

<400> SEQUENCE: 17

```
gaggtgcagc tggtggagtc tgggggaggc ttggtacagc ctggggggtc cctgacactc    60
tcctgtacag cctctggatt ctcctttagc agctatgtca tgagctgggt ccgccagtct   120
cctgggaagg ggctggagtg ggtctcagct attggtggta gtggtactag tacatactac   180
agagactccg tgaagggccg gttcaccatc tccagagaca attccaagaa cacactgaat   240
ctgcaaatga gcagcctgag agccgaggac acggccgtat attactgtgc gagagatggg   300
ctggggcacc gggactactg gggccaggga accctggtca ccgtctcctc a            351
```

<210> SEQ ID NO 18
<211> LENGTH: 117
<212> TYPE: PRT
<213> ORGANISM: Artificial Sequence
<220> FEATURE:
<223> OTHER INFORMATION: synthetic

<400> SEQUENCE: 18

```
Glu Val Gln Leu Val Glu Ser Gly Gly Gly Leu Val Gln Pro Gly Gly
1               5                   10                  15
Ser Leu Thr Leu Ser Cys Thr Ala Ser Gly Phe Ser Phe Ser Ser Tyr
            20                  25                  30
Val Met Ser Trp Val Arg Gln Ser Pro Gly Lys Gly Leu Glu Trp Val
        35                  40                  45
Ser Ala Ile Gly Gly Ser Gly Thr Ser Thr Tyr Tyr Arg Asp Ser Val
    50                  55                  60
Lys Gly Arg Phe Thr Ile Ser Arg Asp Asn Ser Lys Asn Thr Leu Asn
65                  70                  75                  80
Leu Gln Met Ser Ser Leu Arg Ala Glu Asp Thr Ala Val Tyr Tyr Cys
                85                  90                  95
Ala Arg Asp Gly Leu Gly His Arg Asp Tyr Trp Gly Gln Gly Thr Leu
            100                 105                 110
Val Thr Val Ser Ser
        115
```

<210> SEQ ID NO 19
<211> LENGTH: 24
<212> TYPE: DNA
<213> ORGANISM: Artificial Sequence
<220> FEATURE:
<223> OTHER INFORMATION: synthetic

<400> SEQUENCE: 19

```
ggattctcct ttagcagcta tgtc                                           24
```

<210> SEQ ID NO 20
<211> LENGTH: 8
<212> TYPE: PRT
<213> ORGANISM: Artificial Sequence
<220> FEATURE:
<223> OTHER INFORMATION: synthetic

<400> SEQUENCE: 20

```
Gly Phe Ser Phe Ser Ser Tyr Val
1               5
```

<210> SEQ ID NO 21
<211> LENGTH: 24
<212> TYPE: DNA

```
<213> ORGANISM: Artificial Sequence
<220> FEATURE:
<223> OTHER INFORMATION: synthetic

<400> SEQUENCE: 21
attggtggta gtggtactag taca                                              24

<210> SEQ ID NO 22
<211> LENGTH: 8
<212> TYPE: PRT
<213> ORGANISM: Artificial Sequence
<220> FEATURE:
<223> OTHER INFORMATION: synthetic

<400> SEQUENCE: 22

Ile Gly Gly Ser Gly Thr Ser Thr
1               5

<210> SEQ ID NO 23
<211> LENGTH: 30
<212> TYPE: DNA
<213> ORGANISM: Artificial Sequence
<220> FEATURE:
<223> OTHER INFORMATION: synthetic

<400> SEQUENCE: 23
gcgagagatg ggctggggca ccgggactac                                        30

<210> SEQ ID NO 24
<211> LENGTH: 10
<212> TYPE: PRT
<213> ORGANISM: Artificial Sequence
<220> FEATURE:
<223> OTHER INFORMATION: synthetic

<400> SEQUENCE: 24

Ala Arg Asp Gly Leu Gly His Arg Asp Tyr
1               5                   10

<210> SEQ ID NO 25
<211> LENGTH: 321
<212> TYPE: DNA
<213> ORGANISM: Artificial Sequence
<220> FEATURE:
<223> OTHER INFORMATION: synthetic

<400> SEQUENCE: 25
gacatccaga tgacccagtc tccatcttcc gtgtctgcat ctgtaggaga cagagtcacc       60
atcacttgtc gggcgagtca gggtattaac agctggttag cctggtatca gcagaaacca      120
gggaaagccc ctaaactcct gatctatgct gcatccagtt tacaaagtgg ggtcccatca      180
aggttcagcg gcagtggttc tgggacagat ttcactctca ccatcagcag cctccagcct      240
gaagattttg caacttacta ttgtcaacag gctaacagtt tcccattcac tttcggccct      300
gggaccaaag tggatatcaa a                                                321

<210> SEQ ID NO 26
<211> LENGTH: 107
<212> TYPE: PRT
<213> ORGANISM: Artificial Sequence
<220> FEATURE:
<223> OTHER INFORMATION: synthetic

<400> SEQUENCE: 26

Asp Ile Gln Met Thr Gln Ser Pro Ser Ser Val Ser Ala Ser Val Gly
```

```
              1               5                  10                 15
Asp Arg Val Thr Ile Thr Cys Arg Ala Ser Gln Gly Ile Asn Ser Trp
              20                 25                 30

Leu Ala Trp Tyr Gln Gln Lys Pro Gly Lys Ala Pro Lys Leu Leu Ile
              35                 40                 45

Tyr Ala Ala Ser Ser Leu Gln Ser Gly Val Pro Ser Arg Phe Ser Gly
              50                 55                 60

Ser Gly Ser Gly Thr Asp Phe Thr Leu Thr Ile Ser Ser Leu Gln Pro
 65                  70                 75                 80

Glu Asp Phe Ala Thr Tyr Tyr Cys Gln Gln Ala Asn Ser Phe Pro Phe
                 85                 90                 95

Thr Phe Gly Pro Gly Thr Lys Val Asp Ile Lys
             100                105
```

<210> SEQ ID NO 27
<211> LENGTH: 18
<212> TYPE: DNA
<213> ORGANISM: Artificial Sequence
<220> FEATURE:
<223> OTHER INFORMATION: synthetic

<400> SEQUENCE: 27
cagggtatta acagctgg    18

<210> SEQ ID NO 28
<211> LENGTH: 6
<212> TYPE: PRT
<213> ORGANISM: Artificial Sequence
<220> FEATURE:
<223> OTHER INFORMATION: synthetic

<400> SEQUENCE: 28

Gln Gly Ile Asn Ser Trp
1               5

<210> SEQ ID NO 29
<211> LENGTH: 9
<212> TYPE: DNA
<213> ORGANISM: Artificial Sequence
<220> FEATURE:
<223> OTHER INFORMATION: synthetic

<400> SEQUENCE: 29 gctgcatcc    9

<210> SEQ ID NO 30
<211> LENGTH: 3
<212> TYPE: PRT
<213> ORGANISM: Artificial Sequence
<220> FEATURE:
<223> OTHER INFORMATION: synthetic

<400> SEQUENCE: 30

Ala Ala Ser
1

<210> SEQ ID NO 31
<211> LENGTH: 27
<212> TYPE: DNA
<213> ORGANISM: Artificial Sequence
<220> FEATURE:
<223> OTHER INFORMATION: synthetic

<400> SEQUENCE: 31

```
caacaggcta acagtttccc attcact                                          27
```

<210> SEQ ID NO 32
<211> LENGTH: 9
<212> TYPE: PRT
<213> ORGANISM: Artificial Sequence
<220> FEATURE:
<223> OTHER INFORMATION: synthetic

<400> SEQUENCE: 32

```
Gln Gln Ala Asn Ser Phe Pro Phe Thr
1               5
```

<210> SEQ ID NO 33
<211> LENGTH: 375
<212> TYPE: DNA
<213> ORGANISM: Artificial Sequence
<220> FEATURE:
<223> OTHER INFORMATION: H1XH20295P2 HCVR NA

<400> SEQUENCE: 33

```
gaagtgcagc tggtggagtc tgggggaggt ctggtacagc ctggcaggtc cctgagactc       60
tcctgtacaa cctctggatt cacctttgat gattatgcca tgcactgggt ccggcaagtt      120
ccagggcagg gcctggagtg ggtcgcaggt cttagctgga acagtgatac cataggctat      180
gcggactctg tgaagggccg attcaccatc tccagagaca cgccaagaa ttccctgtat      240 ctgcaaatga aagtctgaa agctgaggac acggccttat attactgtac aaaagatttc      300
taccatagtt tgaataattg gaactactac tactttgact actggggcca gggaaccctg      360
gtcaccgtct cctca                                                       375
```

<210> SEQ ID NO 34
<211> LENGTH: 125
<212> TYPE: PRT
<213> ORGANISM: Artificial Sequence
<220> FEATURE:
<223> OTHER INFORMATION: H1XH20295P2 HCVR

<400> SEQUENCE: 34

```
Glu Val Gln Leu Val Glu Ser Gly Gly Gly Leu Val Gln Pro Gly Arg
1               5                   10                  15

Ser Leu Arg Leu Ser Cys Thr Thr Ser Gly Phe Thr Phe Asp Asp Tyr
            20                  25                  30

Ala Met His Trp Val Arg Gln Val Pro Gly Gln Gly Leu Glu Trp Val
        35                  40                  45

Ala Gly Leu Ser Trp Asn Ser Asp Thr Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Lys Ser Leu Lys Ala Glu Asp Thr Ala Leu Tyr Tyr Cys
                85                  90                  95

Thr Lys Asp Phe Tyr His Ser Leu Asn Asn Trp Asn Tyr Tyr Tyr Phe
            100                 105                 110

Asp Tyr Trp Gly Gln Gly Thr Leu Val Thr Val Ser Ser
        115                 120                 125
```

<210> SEQ ID NO 35
<211> LENGTH: 24
<212> TYPE: DNA
<213> ORGANISM: Artificial Sequence

<220> FEATURE:
<223> OTHER INFORMATION: H1XH20295P2 HCDR1 NA

<400> SEQUENCE: 35
ggattcacct ttgatgatta tgcc                                         24

<210> SEQ ID NO 36
<211> LENGTH: 8
<212> TYPE: PRT
<213> ORGANISM: Artificial Sequence
<220> FEATURE:
<223> OTHER INFORMATION: H1XH20295P2 HCDR1

<400> SEQUENCE: 36

Gly Phe Thr Phe Asp Asp Tyr Ala
1               5

<210> SEQ ID NO 37
<211> LENGTH: 24
<212> TYPE: DNA
<213> ORGANISM: Artificial Sequence
<220> FEATURE:
<223> OTHER INFORMATION: H1XH20295P2 HCDR2 NA

<400> SEQUENCE: 37
cttagctgga acagtgatac cata                                         24

<210> SEQ ID NO 38
<211> LENGTH: 8
<212> TYPE: PRT
<213> ORGANISM: Artificial Sequence
<220> FEATURE:
<223> OTHER INFORMATION: H1XH20295P2 HCDR2

<400> SEQUENCE: 38

Leu Ser Trp Asn Ser Asp Thr Ile
1               5

<210> SEQ ID NO 39
<211> LENGTH: 54
<212> TYPE: DNA
<213> ORGANISM: Artificial Sequence
<220> FEATURE:
<223> OTHER INFORMATION: H1XH20295P2 HCDR3 NA

<400> SEQUENCE: 39
acaaaagatt tctaccatag tttgaataat tggaactact actactttga ctac         54

<210> SEQ ID NO 40
<211> LENGTH: 18
<212> TYPE: PRT
<213> ORGANISM: Artificial Sequence
<220> FEATURE:
<223> OTHER INFORMATION: H1XH20295P2 HCDR3

<400> SEQUENCE: 40

Thr Lys Asp Phe Tyr His Ser Leu Asn Asn Trp Asn Tyr Tyr Tyr Phe
1               5                   10                  15

Asp Tyr

<210> SEQ ID NO 41
<211> LENGTH: 324
<212> TYPE: DNA
<213> ORGANISM: Artificial Sequence
<220> FEATURE:
<223> OTHER INFORMATION: H1XH20295P2 LCVR NA

<400> SEQUENCE: 41

```
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccgtca     180
aggttcagtg gcagtggatc tgggacagat ttcactctca ccatcagcag tctgcaacct     240
gaagattttg caacttacta ctgtcaacag agttacagta cccctccgat caccttcggc     300
caagggacac gactggagat taaa                                            324
```

<210> SEQ ID NO 42
<211> LENGTH: 108
<212> TYPE: PRT
<213> ORGANISM: Artificial Sequence
<220> FEATURE:
<223> OTHER INFORMATION: H1XH20295P2 LCVR

<400> SEQUENCE: 42

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
            20                  25                  30
Leu Asn Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Tyr Ser Thr Pro Pro
                85                  90                  95
Ile Thr Phe Gly Gln Gly Thr Arg Leu Glu Ile Lys
            100                 105
```

<210> SEQ ID NO 43
<211> LENGTH: 18
<212> TYPE: DNA
<213> ORGANISM: Artificial Sequence
<220> FEATURE:
<223> OTHER INFORMATION: H1XH20295P2 LCDR1 NA

<400> SEQUENCE: 43

```
cagagcatta gcagctat                                                    18
```

<210> SEQ ID NO 44
<211> LENGTH: 6
<212> TYPE: PRT
<213> ORGANISM: Artificial Sequence
<220> FEATURE:
<223> OTHER INFORMATION: H1XH20295P2 LCDR1

<400> SEQUENCE: 44

```
Gln Ser Ile Ser Ser Tyr
1               5
```

<210> SEQ ID NO 45
<211> LENGTH: 9
<212> TYPE: DNA
<213> ORGANISM: Artificial Sequence
<220> FEATURE:
<223> OTHER INFORMATION: H1XH20295P2 LCDR2 NA

<400> SEQUENCE: 45 gctgcatcc                                                                    9

<210> SEQ ID NO 46
<211> LENGTH: 3
<212> TYPE: PRT
<213> ORGANISM: Artificial Sequence
<220> FEATURE:
<223> OTHER INFORMATION: H1XH20295P2 LCDR2

<400> SEQUENCE: 46

Ala Ala Ser
1

<210> SEQ ID NO 47
<211> LENGTH: 30
<212> TYPE: DNA
<213> ORGANISM: Artificial Sequence
<220> FEATURE:
<223> OTHER INFORMATION: H1XH20295P2 LCDR3 NA

<400> SEQUENCE: 47
caacagagtt acagtaccccc tccgatcacc                                           30

<210> SEQ ID NO 48
<211> LENGTH: 10
<212> TYPE: PRT
<213> ORGANISM: Artificial Sequence
<220> FEATURE:
<223> OTHER INFORMATION: H1XH20295P2 LCDR3

<400> SEQUENCE: 48

Gln Gln Ser Tyr Ser Thr Pro Pro Ile Thr
1               5                   10

<210> SEQ ID NO 49
<211> LENGTH: 1365
<212> TYPE: DNA
<213> ORGANISM: Artificial Sequence
<220> FEATURE:
<223> OTHER INFORMATION: H1H20295P2-Full length heavy chain  NA

<400> SEQUENCE: 49
gaagtgcagc tggtggagtc tgggggaggt ctggtacagc ctggcaggtc cctgagactc           60
tcctgtacaa cctctggatt cacctttgat gattatgcca tgcactgggt ccggcaagtt          120
ccagggcagg gcctggagtg ggtcgcaggt cttagctgga acagtgatac cataggctat          180
gcggactctg tgaagggccg attcaccatc tccagagaca acgccaagaa ttccctgtat          240
ctgcaaatga aaagtctgaa agctgaggac acggccttat attactgtac aaaagatttc          300
taccatagtt tgaataattg gaactactac tactttgact actggggcca gggaaccctg          360
gtcaccgtct cctcagcctc caccaagggc ccatcggtct tccccctggc accctcctcc          420
aagagcacct ctgggggcac agcggccctg ggctgcctgg tcaaggacta cttccccgaa          480
ccggtgacgg tgtcgtggaa ctcaggcgcc ctgaccagcg gcgtgcacac cttcccggct          540
gtcctacagt cctcaggact ctactccctc agcagcgtgg tgaccgtgcc ctccagcagc          600
ttgggcaccc agacctacat ctgcaacgtg aatcacaagc ccagcaacac caaggtggac          660
aagaaagttg agcccaaatc ttgtgacaaa actcacacat gcccaccgtg cccagcacct          720
gaactcctgg ggggaccgtc agtcttcctc ttccccccaa aacccaagga caccctcatg          780
atctcccgga cccctgaggt cacatgcgtg gtggtggacg tgagccacga agaccctgag          840

```
gtcaagttca actggtacgt ggacggcgtg gaggtgcata atgccaagac aaagccgcgg    900
gaggagcagt acaacagcac gtaccgtgtg gtcagcgtcc tcaccgtcct gcaccaggac    960
tggctgaatg gcaaggagta caagtgcaag gtctccaaca agccctccca gcccccatc    1020 gagaaaacca tctccaaagc caagggcag ccccgagaac acaggtgta caccctgccc    1080 ccatcccggg atgagctgac caagaaccag gtcagcctga cctgcctggt caaaggcttc    1140
tatcccagcg acatcgccgt ggagtgggag agcaatgggc agccggagaa caactacaag    1200
accacgcctc ccgtgctgga ctccgacggc tccttcttcc tctacagcaa gctcaccgtg    1260
gacaagagca ggtggcagca ggggaacgtc ttctcatgct ccgtgatgca tgaggctctg    1320
cacaaccact acacgcagaa gtccctctcc ctgtctccgg gtaaa             1365
```

<210> SEQ ID NO 50
<211> LENGTH: 455
<212> TYPE: PRT
<213> ORGANISM: Artificial Sequence
<220> FEATURE:
<223> OTHER INFORMATION: H1H20295P2-Full length heavy chain

<400> SEQUENCE: 50

```
Glu Val Gln Leu Val Glu Ser Gly Gly Gly Leu Val Gln Pro Gly Arg
1               5                   10                  15

Ser Leu Arg Leu Ser Cys Thr Thr Ser Gly Phe Thr Phe Asp Asp Tyr
            20                  25                  30

Ala Met His Trp Val Arg Gln Val Pro Gly Gln Gly Leu Glu Trp Val
        35                  40                  45

Ala Gly Leu Ser Trp Asn Ser Asp Thr Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Lys Ser Leu Lys Ala Glu Asp Thr Ala Leu Tyr Tyr Cys
                85                  90                  95

Thr Lys Asp Phe Tyr His Ser Leu Asn Asn Trp Asn Tyr Tyr Tyr Phe
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270
```

-continued

Asp Val Ser His Glu Asp Pro Glu Val Lys Phe Asn Trp Tyr Val Asp
            275                 280                 285
Gly Val Glu Val His Asn Ala Lys Thr Lys Pro Arg Glu Glu Gln Tyr
        290                 295                 300
Asn Ser Thr Tyr Arg Val Val Ser Val Leu Thr Val Leu His Gln Asp
305                 310                 315                 320
Trp Leu Asn Gly Lys Glu Tyr Lys Cys Lys Val Ser Asn Lys Ala Leu
                325                 330                 335
Pro Ala Pro Ile Glu Lys Thr Ile Ser Lys Ala Lys Gly Gln Pro Arg
            340                 345                 350
Glu Pro Gln Val Tyr Thr Leu Pro Pro Ser Arg Asp Glu Leu Thr Lys
        355                 360                 365
Asn Gln Val Ser Leu Thr Cys Leu Val Lys Gly Phe Tyr Pro Ser Asp
370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Lys Ser Arg Trp Gln Gln Gly Asn Val Phe Ser
            420                 425                 430
Cys Ser Val Met His Glu Ala Leu His Asn His Tyr Thr Gln Lys Ser
        435                 440                 445
Leu Ser Leu Ser Pro Gly Lys
450                 455

<210> SEQ ID NO 51
<211> LENGTH: 645
<212> TYPE: DNA
<213> ORGANISM: Artificial Sequence
<220> FEATURE:
<223> OTHER INFORMATION: H1H20295P2-Full length light chain NA

<400> SEQUENCE: 51
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccgtca   180
aggttcagtg gcagtggatc tgggacagat ttcactctca ccatcagcag tctgcaacct   240
gaagattttg caacttacta ctgtcaacag agttacagta cccctccgat caccttcggc   300
caagggacac gactggagat taaacgaact gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
acgctgagca agcagactac gagaaacac aaagtctacg cctgcgaagt cacccatcag   600
ggcctgagct cgcccgtcac aaagagcttc aacaggggag agtgt              645

<210> SEQ ID NO 52
<211> LENGTH: 215
<212> TYPE: PRT
<213> ORGANISM: Artificial Sequence
<220> FEATURE:
<223> OTHER INFORMATION: H1H20295P2-Full length light chain

<400> SEQUENCE: 52

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Pro
                 85                  90                  95

Ile Thr Phe Gly Gln Gly Thr Arg Leu Glu Ile Lys Arg Thr Val Ala
             100                 105                 110

Ala Pro Ser Val Phe Ile Phe Pro Pro Ser Asp Glu Gln Leu Lys Ser
         115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                 165                 170                 175

Ser Ser Thr Leu Thr Leu Ser Lys Ala Asp Tyr Glu Lys His Lys Val
             180                 185                 190

Tyr Ala Cys Glu Val Thr His Gln Gly Leu Ser Ser Pro Val Thr Lys
         195                 200                 205

Ser Phe Asn Arg Gly Glu Cys
    210                 215

<210> SEQ ID NO 53
<211> LENGTH: 1365
<212> TYPE: DNA
<213> ORGANISM: Artificial Sequence
<220> FEATURE:
<223> OTHER INFORMATION: H1xH20295P2 Full length heavy chain (with */*
      mutation in IgG1 constant region) NA

<400> SEQUENCE: 53
gaagtgcagc tggtggagtc tgggggaggt ctggtacagc ctggcaggtc cctgagactc      60
tcctgtacaa cctctggatt cacctttgat gattatgcca tgcactgggt ccggcaagtt     120
ccagggcagg gcctggagtg ggtcgcaggt cttagctgga acagtgatac cataggctat     180
gcggactctg tgaagggccg attcaccatc tccagagaca acgccaagaa ttccctgtat     240
ctgcaaatga aaagtctgaa agctgaggac acggccttat attactgtac aaaagatttc     300
taccatagtt tgaataattg gaactactac tactttgact actggggcca gggaaccctg     360
gtcaccgtct cctcagcctc aactaagggc ccaagcgtct tccattggc tccatccagt      420 aaatcaactt caggggggac cgcagctctg ggtgcctcg tgaaggacta cttccctgaa      480
cctgtcacag tctcctggaa ctccggggct ctgaccagcg gagttcacac ctttcctgcc     540
gtgcttcagt cttccgggct gtactcattg agcagtgtcg ttactgtacc atcctcctcc     600
ctgggtactc aaacctacat ctgtaatgtg aaccacaagc cctccaacac caaggttgac     660
aaaaaggtgg aaccaaagag ttgtgataag actcatacct gcccccatg tcctgccccc      720 gagctgctgg gaggaccttc agtgttcttg ttccctccca aaccaaaga cactttgatg      780
```

```
atttcacgaa cccctgaagt gacctgtgtg gtggtcgatg tcagccacga agaccctgaa      840
gttaagttta actggtatgt ggatggcgta gaggttcaca acgctaagac taaacccaga      900
gaggagcaat ataatagtac ctatagggtc gtgtctgtgc tgacagtctt gcatcaggac      960
tggcttaacg gtaaggagta caagtgtaag gtgtcaaaca aggcactgcc tgcacctatc     1020
gagaagacca tctctaaggc caaaggtcaa ccaagggagc cccaggtata ctctttgcca     1080
ccctctcggg acgagctgac aaaaaatcag gtgagtctga cctgtctcgt gaaaggattt     1140
taccctagcg acatcgccgt ggagtgggag agtaatggcc agcccgagaa taactacaag     1200
accaccccac cagttctgga ctctgacggg tctttcttcc tttatagtaa gctgaccgta     1260
gataagtctc gctggcagca aggcaatgta ttctcttgca gtgtcatgca cgaggccctc     1320
cataaccgat tcacccaaaa atctctgtct ctgtctcctg gaaag                     1365
```

<210> SEQ ID NO 54
<211> LENGTH: 455
<212> TYPE: PRT
<213> ORGANISM: Artificial Sequence
<220> FEATURE:
<223> OTHER INFORMATION: H1xH20295P2 Full length heavy chain (with */*
     mutation in IgG1 constant region)

<400> SEQUENCE: 54

```
Glu Val Gln Leu Val Glu Ser Gly Gly Gly Leu Val Gln Pro Gly Arg
1               5                   10                  15

Ser Leu Arg Leu Ser Cys Thr Thr Ser Gly Phe Thr Phe Asp Asp Tyr
            20                  25                  30

Ala Met His Trp Val Arg Gln Val Pro Gly Gln Gly Leu Glu Trp Val
        35                  40                  45

Ala Gly Leu Ser Trp Asn Ser Asp Thr Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Lys Ser Leu Lys Ala Glu Asp Thr Ala Leu Tyr Tyr Cys
                85                  90                  95

Thr Lys Asp Phe Tyr His Ser Leu Asn Asn Trp Asn Tyr Tyr Tyr Phe
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255
```

```
Asp Thr Leu Met Ile Ser Arg Thr Pro Glu Val Thr Cys Val Val
            260                 265                 270
Asp Val Ser His Glu Asp Pro Glu Val Lys Phe Asn Trp Tyr Val Asp
        275                 280                 285
Gly Val Glu Val His Asn Ala Lys Thr Lys Pro Arg Glu Glu Gln Tyr
    290                 295                 300
Asn Ser Thr Tyr Arg Val Val Ser Val Leu Thr Val Leu His Gln Asp
305                 310                 315                 320
Trp Leu Asn Gly Lys Glu Tyr Lys Cys Lys Val Ser Asn Lys Ala Leu
                325                 330                 335
Pro Ala Pro Ile Glu Lys Thr Ile Ser Lys Ala Lys Gly Gln Pro Arg
            340                 345                 350
Glu Pro Gln Val Tyr Thr Leu Pro Pro Ser Arg Asp Glu Leu Thr Lys
        355                 360                 365
Asn Gln Val Ser Leu Thr Cys Leu Val Lys Gly Phe Tyr Pro Ser Asp
    370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Lys Ser Arg Trp Gln Gln Gly Asn Val Phe Ser
            420                 425                 430
Cys Ser Val Met His Glu Ala Leu His Asn Arg Phe Thr Gln Lys Ser
        435                 440                 445
Leu Ser Leu Ser Pro Gly Lys
    450                 455

<210> SEQ ID NO 55
<211> LENGTH: 990
<212> TYPE: DNA
<213> ORGANISM: Artificial Sequence
<220> FEATURE:
<223> OTHER INFORMATION: hIgG1 Heavy Chain (WT) NA

<400> SEQUENCE: 55
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctgggggga     360
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag gcagccccg agaaccacag gtgtacaccc tgcccccatc ccgggatgag     720
ctgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctac agcaagctca ccgtggacaa gagcaggtgg     900
```

-continued

```
cagcagggga acgtcttctc atgctccgtg atgcatgagg ctctgcacaa ccactacacg    960
cagaagtccc tctccctgtc tccgggtaaa                                     990
```

<210> SEQ ID NO 56
<211> LENGTH: 330
<212> TYPE: PRT
<213> ORGANISM: Artificial Sequence
<220> FEATURE:
<223> OTHER INFORMATION: hIgG1 Heavy Chain (WT)

<400> SEQUENCE: 56

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 57

```
<211> LENGTH: 990
<212> TYPE: DNA
<213> ORGANISM: Artificial Sequence
<220> FEATURE:
<223> OTHER INFORMATION: hIgG1 Heavy Chain */* Mutation NA

<400> SEQUENCE: 57
gcctcaacta agggcccaag cgtctttcca ttggctccat ccagtaaatc aacttcaggg      60
gggaccgcag ctctggggtg cctcgtgaag gactacttcc ctgaacctgt cacagtctcc     120
tggaactccg gggctctgac cagcggagtt cacacctttc ctgccgtgct tcagtcttcc     180
gggctgtact cattgagcag tgtcgttact gtaccatcct cctccctggg tactcaaacc     240
tacatctgta atgtgaacca caagccctcc aacaccaagg ttgacaaaaa ggtggaacca     300
aagagttgtg ataagactca tacctgcccc ccatgtcctg cccccgagct gctgggagga     360
ccttcagtgt tcttgttccc tcccaaacca aaagacactt tgatgatttc acgaacccct     420
gaagtgacct gtgtggtggt cgatgtcagc cacgaagacc ctgaagttaa gtttaactgg     480
tatgtggatg gcgtagaggt tcacaacgct aagactaaac ccagagagga gcaatataat     540
agtacctata gggtcgtgtc tgtgctgaca gtcttgcatc aggactggct taacggtaag     600
gagtacaagt gtaaggtgtc aaacaaggca ctgcctgcac ctatcgagaa gaccatctct     660
aaggccaaag gtcaaccaag ggagccccag gtatatactt tgccaccctc tcgggacgag     720
ctgacaaaaa atcaggtgag tctgacctgt ctcgtgaaaa gattttaccc tagcgacatc     780
gccgtggagt gggagagtaa tggccagccc gagaataact acaagaccac cccaccagtt     840
ctggactctg acgggtcttt cttcctttat agtaagctga ccgtagataa gtctcgctgg     900
cagcaaggca atgtattctc ttgcagtgtc atgcacgagg ccctccataa ccgattcacc     960
caaaaatctc tgtctctgtc tcctggaaag                                     990

<210> SEQ ID NO 58
<211> LENGTH: 330
<212> TYPE: PRT
<213> ORGANISM: Artificial Sequence
<220> FEATURE:
<223> OTHER INFORMATION: hIgG1  Heavy Chain */* Mutation (H435R,Y436F)

<400> SEQUENCE: 58

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140
```

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn Arg Phe Thr
305                 310                 315                 320

Gln Lys Ser Leu Ser Leu Ser Pro Gly Lys
                325                 330

<210> SEQ ID NO 59
<211> LENGTH: 378
<212> TYPE: DNA
<213> ORGANISM: Artificial Sequence
<220> FEATURE:
<223> OTHER INFORMATION: synthetic

<400> SEQUENCE: 59
caggtgcagc tggtggagtc tgggggaggc gtggtccagc ctggggaggtc cctgagactc     60
tcctgtgcag tgtctggact catcttcagt aactatggca tgcactgggt ccgccaggct    120
ccaggcaagg gctggagtg gtggcagtt atatggtatg atggaagtaa taaatactat      180
gtagactccg tgaagggccg cttcaccatc tccagagaca attccaagaa cacgctgtat    240
ctgcaaatga acagcctgag aggcgaggac acggctatat attactgtgc gagagatcgg    300
agagggctgg aactatttaa ctactactac cacggttttgg acgtctgggg ccaagggacc   360
acggtcaccg tctcctca                                                   378

<210> SEQ ID NO 60
<211> LENGTH: 126
<212> TYPE: PRT
<213> ORGANISM: Artificial Sequence
<220> FEATURE:
<223> OTHER INFORMATION: synthetic

<400> SEQUENCE: 60

Gln Val Gln Leu Val Glu Ser Gly Gly Gly Val Val Gln Pro Gly Arg
1               5                   10                  15

Ser Leu Arg Leu Ser Cys Ala Val Ser Gly Leu Ile Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Val Asp Ser Val
                50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Gly Glu Asp Thr Ala Ile Tyr Tyr Cys
                 85                  90                  95

Ala Arg Asp Arg Arg Gly Leu Glu Leu Phe Asn Tyr Tyr His Gly
                100                 105                 110

Leu Asp Val Trp Gly Gln Gly Thr Thr Val Thr Val Ser Ser
            115                 120                 125

<210> SEQ ID NO 61
<211> LENGTH: 24
<212> TYPE: DNA
<213> ORGANISM: Artificial Sequence
<220> FEATURE:
<223> OTHER INFORMATION: synthetic

<400> SEQUENCE: 61
ggactcatct tcagtaacta tggc                                    24

<210> SEQ ID NO 62
<211> LENGTH: 8
<212> TYPE: PRT
<213> ORGANISM: Artificial Sequence
<220> FEATURE:
<223> OTHER INFORMATION: synthetic

<400> SEQUENCE: 62

Gly Leu Ile Phe Ser Asn Tyr Gly
 1               5

<210> SEQ ID NO 63
<211> LENGTH: 24
<212> TYPE: DNA
<213> ORGANISM: Artificial Sequence
<220> FEATURE:
<223> OTHER INFORMATION: synthetic

<400> SEQUENCE: 63
atatggtatg atggaagtaa taaa                                    24

<210> SEQ ID NO 64
<211> LENGTH: 8
<212> TYPE: PRT
<213> ORGANISM: Artificial Sequence
<220> FEATURE:
<223> OTHER INFORMATION: synthetic

<400> SEQUENCE: 64

Ile Trp Tyr Asp Gly Ser Asn Lys
 1               5

<210> SEQ ID NO 65
<211> LENGTH: 57
<212> TYPE: DNA
<213> ORGANISM: Artificial Sequence
<220> FEATURE:
<223> OTHER INFORMATION: synthetic

<400> SEQUENCE: 65
gcgagagatc ggagagggct ggaactattt aactactact accacggttt ggacgtc    57

<210> SEQ ID NO 66

<211> LENGTH: 19
<212> TYPE: PRT
<213> ORGANISM: Artificial Sequence
<220> FEATURE:
<223> OTHER INFORMATION: synthetic

<400> SEQUENCE: 66

Ala Arg Asp Arg Arg Gly Leu Glu Leu Phe Asn Tyr Tyr Tyr His Gly
1               5                   10                  15

Leu Asp Val

<210> SEQ ID NO 67
<211> LENGTH: 321
<212> TYPE: DNA
<213> ORGANISM: Artificial Sequence
<220> FEATURE:
<223> OTHER INFORMATION: synthetic

<400> SEQUENCE: 67
gacatccaga tgacccagtc tccatcctca ctgtctgcat ctgtaggaga cagagtcacc      60
atcacttgtc gggcgagtca gggcattagc aattttttag cctggtttca gcagaaacca     120
gggaaagccc ctaagtccct gatctatgct gcatccagtt tgcaaagtgg ggtcccatca     180 agttcagcg gcagtggatc tgggacagat ttcactctca ccatcagcag cctgcagcct     240
gaagattttg caacttatta ctgccaacag tataatagtt acccattcac tttcggccct     300
gggaccaaag tggatatcaa a                                               321

<210> SEQ ID NO 68
<211> LENGTH: 107
<212> TYPE: PRT
<213> ORGANISM: Artificial Sequence
<220> FEATURE:
<223> OTHER INFORMATION: synthetic

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Phe
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Phe
                85                  90                  95

Thr Phe Gly Pro Gly Thr Lys Val Asp Ile Lys
            100                 105

<210> SEQ ID NO 69
<211> LENGTH: 18
<212> TYPE: DNA
<213> ORGANISM: Artificial Sequence
<220> FEATURE:
<223> OTHER INFORMATION: synthetic

<400> SEQUENCE: 69
cagggcatta gcaatttt                                                    18

```
<210> SEQ ID NO 70
<211> LENGTH: 6
<212> TYPE: PRT
<213> ORGANISM: Artificial Sequence
<220> FEATURE:
<223> OTHER INFORMATION: synthetic

<400> SEQUENCE: 70

Gln Gly Ile Ser Asn Phe
1               5

<210> SEQ ID NO 71
<211> LENGTH: 9
<212> TYPE: DNA
<213> ORGANISM: Artificial Sequence
<220> FEATURE:
<223> OTHER INFORMATION: synthetic

<400> SEQUENCE: 71 gctgcatcc                                                                  9

<210> SEQ ID NO 72
<211> LENGTH: 3
<212> TYPE: PRT
<213> ORGANISM: Artificial Sequence
<220> FEATURE:
<223> OTHER INFORMATION: synthetic

<400> SEQUENCE: 72

Ala Ala Ser
1

<210> SEQ ID NO 73
<211> LENGTH: 27
<212> TYPE: DNA
<213> ORGANISM: Artificial Sequence
<220> FEATURE:
<223> OTHER INFORMATION: synthetic

<400> SEQUENCE: 73
caacagtata atagttaccc attcact                                             27

<210> SEQ ID NO 74
<211> LENGTH: 9
<212> TYPE: PRT
<213> ORGANISM: Artificial Sequence
<220> FEATURE:
<223> OTHER INFORMATION: synthetic

<400> SEQUENCE: 74

Gln Gln Tyr Asn Ser Tyr Pro Phe Thr
1               5

<210> SEQ ID NO 75
<211> LENGTH: 1371
<212> TYPE: DNA
<213> ORGANISM: Artificial Sequence
<220> FEATURE:
<223> OTHER INFORMATION: synthetic

<400> SEQUENCE: 75
caggtgcagc tggtggagtc tgggggaggc gtggtccagc ctggagggtc cctgagactc         60
tcctgtgcag tgtctggact catcttcagt aactatggca tgcactgggt ccgccaggct        120
ccaggcaagg ggctggagtg ggtggcagtt atatggtatg atggaagtaa taatactat         180 gtagactccg tgaagggccg cttcaccatc tccagagaca attccaagaa cacgctgtat        240
```

-continued

```
ctgcaaatga acagcctgag aggcgaggac acggctatat attactgtgc gagagatcgg      300
agagggctgg aactatttaa ctactactac cacggtttgg acgtctgggg ccaagggacc      360
acggtcaccg tctcctcagc ctcaacaaaa ggtccctcag tctttcctct tgctccatcc      420
tccaaaagta catcaggagg taccgcagcc cttggatgcc tcgtcaagga ttattttccc      480
gaaccagtta ccgtttcctg gaactcaggc gctctcacct ctggagtaca tactttcct       540
gcagtcctcc aatcctctgg cctttactcc ctttctagcg tagtaaccgt accatcatca      600
tccctcggaa cccaaactta tatctgtaat gttaatcaca aacccagcaa caccaaagta      660
gacaaaaaag ttgaacctaa atcatgcgat aaaacccaca cttgccccc ctgtccagca       720
ccagaactcc ttggcggccc ctcagttttc cttttccac caaagcccaa agacaccctt       780
atgatctcca gaaccccga gttacatgc gtagtcgttg acgtttctca cgaagatcca        840
gaagtcaaat tcaattggta cgttgatggc gttgaagtcc ataatgcaaa acaaaaccc       900
cgagaagaac agtacaattc aacatatcga gtagttagcg tacttacagt tctgcaccaa      960
gattggctga acggaaaaga atataaatgt aaagtctcta acaaagcact ccctgcccca     1020
attgaaaaaa caatctcaaa agccaaaggc caacctcgcg aacctcaggt ttacacactt     1080
cccccctccc gcgacgaact gactaaaaac caggtttcct tgacatgcct tgtaaaaggt     1140
ttttacccct ccgatatcgc cgtagaatgg gaatctaatg gacaaccaga aaacaattac     1200
aaaactaccc ctcctgtgct cgattccgat ggctctttt tcctctattc taagctcacc      1260
gttgacaagt ctcgttggca gcagggaaac gtattcagtt gcagcgtcat gcacgaagcc     1320
cttcataata gattcaccca aaagtctctt tctctctctc ctggtaagta g              1371
```

<210> SEQ ID NO 76
<211> LENGTH: 456
<212> TYPE: PRT
<213> ORGANISM: Artificial Sequence
<220> FEATURE:
<223> OTHER INFORMATION: synthetic

<400> SEQUENCE: 76

```
Gln Val Gln Leu Val Glu Ser Gly Gly Gly Val Gln Pro Gly Arg
1               5                   10                  15

Ser Leu Arg Leu Ser Cys Ala Val Ser Gly Leu Ile Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Gly Glu Asp Thr Ala Ile Tyr Tyr Cys
                85                  90                  95

Ala Arg Asp Arg Arg Gly Leu Glu Leu Phe Asn Tyr Tyr Tyr His Gly
            100                 105                 110

Leu Asp Val Trp Gly Gln Gly Thr Thr Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160
```

```
Glu Pro Val Thr Val Ser Trp Asn Ser Gly Ala Leu Thr Ser Gly Val
                165                 170                 175
His Thr Phe Pro Ala Val Leu Gln Ser Ser Gly Leu Tyr Ser Leu Ser
            180                 185                 190
Ser Val Val Thr Val Pro Ser Ser Ser Leu Gly Thr Gln Thr Tyr Ile
        195                 200                 205
Cys Asn Val Asn His Lys Pro Ser Asn Thr Lys Val Asp Lys Lys Val
    210                 215                 220
Glu Pro Lys Ser Cys Asp Lys Thr His Thr Cys Pro Pro Cys Pro Ala
225                 230                 235                 240
Pro Glu Leu Leu Gly Gly Pro Ser Val Phe Leu Phe Pro Pro Lys Pro
                245                 250                 255
Lys Asp Thr Leu Met Ile Ser Arg Thr Pro Glu Val Thr Cys Val Val
            260                 265                 270
Val Asp Val Ser His Glu Asp Pro Glu Val Lys Phe Asn Trp Tyr Val
        275                 280                 285
Asp Gly Val Glu Val His Asn Ala Lys Thr Lys Pro Arg Glu Glu Gln
    290                 295                 300
Tyr Asn Ser Thr Tyr Arg Val Val Ser Val Leu Thr Val Leu His Gln
305                 310                 315                 320
Asp Trp Leu Asn Gly Lys Glu Tyr Lys Cys Lys Val Ser Asn Lys Ala
                325                 330                 335
Leu Pro Ala Pro Ile Glu Lys Thr Ile Ser Lys Ala Lys Gly Gln Pro
            340                 345                 350
Arg Glu Pro Gln Val Tyr Thr Leu Pro Pro Ser Arg Asp Glu Leu Thr
        355                 360                 365
Lys Asn Gln Val Ser Leu Thr Cys Leu Val Lys Gly Phe Tyr Pro Ser
    370                 375                 380
Asp Ile Ala Val Glu Trp Glu Ser Asn Gly Gln Pro Glu Asn Asn Tyr
385                 390                 395                 400
Lys Thr Thr Pro Pro Val Leu Asp Ser Asp Gly Ser Phe Phe Leu Tyr
                405                 410                 415
Ser Lys Leu Thr Val Asp Lys Ser Arg Trp Gln Gln Gly Asn Val Phe
            420                 425                 430
Ser Cys Ser Val Met His Glu Ala Leu His Asn Arg Phe Thr Gln Lys
        435                 440                 445
Ser Leu Ser Leu Ser Pro Gly Lys
    450                 455

<210> SEQ ID NO 77
<211> LENGTH: 645
<212> TYPE: DNA
<213> ORGANISM: Artificial Sequence
<220> FEATURE:
<223> OTHER INFORMATION: synthetic

<400> SEQUENCE: 77
gacatccaga tgacccagtc tccatcctca ctgtctgcat ctgtaggaga cagagtcacc      60
atcacttgtc gggcgagtca gggcattagc aatttttag cctggtttca gcagaaacca     120
gggaaagccc ctaagtccct gatctatgct gcatccagtt tgcaaagtgg ggtcccatca     180
aagttcagcg gcagtggatc tgggacagat ttcactctca ccatcagcag cctgcagcct     240
gaagattttg caacttatta ctgccaacag tataatagtt acccattcac tttcggccct     300
gggaccaaag tggatatcaa acgaactgtg gctgcaccat ctgtcttcat cttcccgcca     360
```

```
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                   645
```

<210> SEQ ID NO 78
<211> LENGTH: 214
<212> TYPE: PRT
<213> ORGANISM: Artificial Sequence
<220> FEATURE:
<223> OTHER INFORMATION: synthetic

<400> SEQUENCE: 78

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Phe
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 79
<211> LENGTH: 354
<212> TYPE: DNA
<213> ORGANISM: Artificial Sequence
<220> FEATURE:
<223> OTHER INFORMATION: synthetic

<400> SEQUENCE: 79

```
gaggtgcagc tggtggagtc tgggggaggc ctggtacagc ctggggggtc cctgagactc    60
tcctgtgcag cctctggatt cacctttaac agctatgcca tgagctggtt ccgccagact   120
ccagggaagg ggctggagtg gctctcagct atgactggta gtggtggtaa cacatactac   180
gcagactccg tgaagggccg gttcaccatc tccagagaca attccaagaa cacgctgtat   240
```
ctgcaaatga caacctgag agccgaggac acggccgtat attactgtgc ggtggataca    300
accatggccc actttgacta ctggggccag ggaaccctgg tcaccgtctc ctca    354

<210> SEQ ID NO 80
<211> LENGTH: 118
<212> TYPE: PRT
<213> ORGANISM: Artificial Sequence
<220> FEATURE:
<223> OTHER INFORMATION: synthetic

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Ser Tyr
            20                  25                  30

Ala Met Ser Trp Phe Arg Gln Thr Pro Gly Lys Gly Leu Glu Trp Leu
        35                  40                  45

Ser Ala Met Thr Gly Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Asn Leu Arg Ala Glu Asp Thr Ala Val Tyr Tyr Cys
                85                  90                  95

Ala Val Asp Thr Thr Met Ala His Phe Asp Tyr Trp Gly Gln Gly Thr
            100                 105                 110

Leu Val Thr Val Ser Ser
        115

<210> SEQ ID NO 81
<211> LENGTH: 24
<212> TYPE: DNA
<213> ORGANISM: Artificial Sequence
<220> FEATURE:
<223> OTHER INFORMATION: synthetic

<400> SEQUENCE: 81
ggattcacct ttaacagcta tgcc    24

<210> SEQ ID NO 82
<211> LENGTH: 8
<212> TYPE: PRT
<213> ORGANISM: Artificial Sequence
<220> FEATURE:
<223> OTHER INFORMATION: synthetic

<400> SEQUENCE: 82

Gly Phe Thr Phe Asn Ser Tyr Ala
1               5

<210> SEQ ID NO 83
<211> LENGTH: 24
<212> TYPE: DNA
<213> ORGANISM: Artificial Sequence
<220> FEATURE:
<223> OTHER INFORMATION: synthetic

<400> SEQUENCE: 83
atgactggta gtggtggtaa caca    24

<210> SEQ ID NO 84
<211> LENGTH: 8

```
<212> TYPE: PRT
<213> ORGANISM: Artificial Sequence
<220> FEATURE:
<223> OTHER INFORMATION: synthetic

<400> SEQUENCE: 84

Met Thr Gly Ser Gly Gly Asn Thr
1               5

<210> SEQ ID NO 85
<211> LENGTH: 33
<212> TYPE: DNA
<213> ORGANISM: Artificial Sequence
<220> FEATURE:
<223> OTHER INFORMATION: synthetic

<400> SEQUENCE: 85
gcggtggata caaccatggc ccactttgac tac                              33

<210> SEQ ID NO 86
<211> LENGTH: 11
<212> TYPE: PRT
<213> ORGANISM: Artificial Sequence
<220> FEATURE:
<223> OTHER INFORMATION: synthetic

<400> SEQUENCE: 86

Ala Val Asp Thr Thr Met Ala His Phe Asp Tyr
1               5                   10

<210> SEQ ID NO 87
<211> LENGTH: 321
<212> TYPE: DNA
<213> ORGANISM: Artificial Sequence
<220> FEATURE:
<223> OTHER INFORMATION: synthetic

<400> SEQUENCE: 87
gacatccaga tgacccagtc tccatcttcc gtgtctgcat ctgtaggaga cagagtcacc    60
atcacttgtc gggcgagtca gggtattagc agctggttag cctggtatca gcagaaacca   120
gggaaagccc ctaagctcct gatctatgct gcttccactt tacaaagtgg ggtcccatca   180
aggttcagtg gcagtggatc tgggacagat ttcactctca ccatcagcag cctgcagcct   240
gaagattttg caacttacta ttgtcaacgg attaacagtt tcccattcac tttcggccct   300
gggaccaaag tggatatcaa a                                            321

<210> SEQ ID NO 88
<211> LENGTH: 107
<212> TYPE: PRT
<213> ORGANISM: Artificial Sequence
<220> FEATURE:
<223> OTHER INFORMATION: synthetic

<400> SEQUENCE: 88

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Arg Ile Asn Ser Phe Pro Phe
            85                  90                  95

Thr Phe Gly Pro Gly Thr Lys Val Asp Ile Lys
            100                 105

<210> SEQ ID NO 89
<211> LENGTH: 18
<212> TYPE: DNA
<213> ORGANISM: Artificial Sequence
<220> FEATURE:
<223> OTHER INFORMATION: synthetic

<400> SEQUENCE: 89
cagggtatta gcagctgg                                                 18

<210> SEQ ID NO 90
<211> LENGTH: 6
<212> TYPE: PRT
<213> ORGANISM: Artificial Sequence
<220> FEATURE:
<223> OTHER INFORMATION: synthetic

<400> SEQUENCE: 90

Gln Gly Ile Ser Ser Trp
1               5

<210> SEQ ID NO 91
<211> LENGTH: 9
<212> TYPE: DNA
<213> ORGANISM: Artificial Sequence
<220> FEATURE:
<223> OTHER INFORMATION: synthetic

<400> SEQUENCE: 91 gctgcttcc                                                            9

<210> SEQ ID NO 92
<211> LENGTH: 27
<212> TYPE: DNA
<213> ORGANISM: Artificial Sequence
<220> FEATURE:
<223> OTHER INFORMATION: synthetic

<400> SEQUENCE: 92
caacggatta acagtttccc attcact                                       27

<210> SEQ ID NO 93
<211> LENGTH: 9
<212> TYPE: PRT
<213> ORGANISM: Artificial Sequence
<220> FEATURE:
<223> OTHER INFORMATION: synthetic

<400> SEQUENCE: 93

Gln Arg Ile Asn Ser Phe Pro Phe Thr
1               5

<210> SEQ ID NO 94
<211> LENGTH: 1347
<212> TYPE: DNA
<213> ORGANISM: Artificial Sequence
<220> FEATURE:
<223> OTHER INFORMATION: synthetic

<400> SEQUENCE: 94

```
gaggtgcagc tggtggagtc tgggggaggc ctggtacagc ctgggggtc cctgagactc      60
tcctgtgcag cctctggatt cacctttaac agctatgcca tgagctggtt ccgccagact     120
ccagggaagg gctggagtg ctctcagct atgactggta gtggtggtaa cacatactac       180
gcagactccg tgaagggccg gttcaccatc tccagagaca attccaagaa cacgctgtat     240
ctgcaaatga acaacctgag agccgaggac acggccgtat attactgtgc ggtggataca     300
accatggccc actttgacta ctggggccag ggaaccctgg tcaccgtctc ctcagcctca     360
acaaaaggtc cctcagtctt tcctcttgct ccatcctcca aaagtacatc aggaggtacc     420
gcagcccttg gatgcctcgt caaggattat tttcccgaac cagttaccgt ttcctggaac     480
tcaggcgctc tcacctctgg agtacatact tttcctgcag tcctccaatc tctggccttt    540
tactcccttt ctagcgtagt aaccgtacca tcatcatccc tcggaaccca aacttatatc     600
tgtaatgtta atcacaaacc cagcaacacc aaagtagaca aaaaagttga acctaaatca     660
tgcgataaaa cccacacttg cccccccgt ccagcaccag aactccttgg cggcccctca      720
gttttccttt ttccaccaaa gcccaaagac acccttatga tctccagaac ccccgaagtt     780
acatgcgtag tcgttgacgt ttctcacgaa gatccagaag tcaaattcaa ttggtacgtt     840
gatggcgttg aagtccataa tgcaaaaaca aaaccccgag aagaacagta caattcaaca     900
tatcgagtag ttagcgtact tacagttctg caccaagatt ggctgaacgg aaaagaatat     960
aaatgtaaag tctctaacaa agcactccct gccccaattg aaaaaacaat ctcaaaagcc    1020
aaaggccaac ctcgcgaacc tcaggtttac acacttcccc cctcccgcga cgaactgact    1080
aaaaaccagg tttccttgac atgccttgta aaaggttttt accctccga tatcgccgta     1140
gaatgggaat ctaatggaca accagaaaac aattacaaaa ctacccctcc tgtgctcgat    1200
tccgatggct ctttttttcct ctattctaag ctcaccgttg acaagtctcg ttggcagcag   1260
ggaaacgtat tcagttgcag cgtcatgcac gaagcccttc ataatagatt cacccaaaag   1320
tctctttctc tctctcctgg taagtag                                        1347
```

<210> SEQ ID NO 95
<211> LENGTH: 448
<212> TYPE: PRT
<213> ORGANISM: Artificial Sequence
<220> FEATURE:
<223> OTHER INFORMATION: synthetic

<400> SEQUENCE: 95

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Ser Tyr
            20                  25                  30

Ala Met Ser Trp Phe Arg Gln Thr Pro Gly Lys Gly Leu Glu Trp Leu
        35                  40                  45

Ser Ala Met Thr Gly Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Asn Leu Arg Ala Glu Asp Thr Ala Val Tyr Tyr Cys
                85                  90                  95

Ala Val Asp Thr Thr Met Ala His Phe Asp Tyr Trp Gly Gln Gly Thr
            100                 105                 110
```

Leu Val Thr Val Ser Ser Ala Ser Thr Lys Gly Pro Ser Val Phe Pro
             115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
             165                 170                 175

Ser Ser Gly Leu Tyr Ser Leu Ser Ser Val Val Thr Val Pro Ser Ser
             180                 185                 190

Ser Leu Gly Thr Gln Thr Tyr Ile Cys Asn Val Asn His Lys Pro Ser
             195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
             245                 250                 255

Thr Pro Glu Val Thr Cys Val Val Val Asp Val Ser His Glu Asp Pro
             260                 265                 270

Glu Val Lys Phe Asn Trp Tyr Val Asp Gly Val Glu Val His Asn Ala
             275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
             325                 330                 335

Ile Ser Lys Ala Lys Gly Gln Pro Arg Glu Pro Gln Val Tyr Thr Leu
             340                 345                 350

Pro Pro Ser Arg Asp Glu Leu Thr Lys Asn Gln Val Ser Leu Thr Cys
             355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
             405                 410                 415

Arg Trp Gln Gln Gly Asn Val Phe Ser Cys Ser Val Met His Glu Ala
             420                 425                 430

Leu His Asn Arg Phe Thr Gln Lys Ser Leu Ser Leu Ser Pro Gly Lys
             435                 440                 445

<210> SEQ ID NO 96
<211> LENGTH: 645
<212> TYPE: DNA
<213> ORGANISM: Artificial Sequence
<220> FEATURE:
<223> OTHER INFORMATION: synthetic

<400> SEQUENCE: 96
gacatccaga tgacccagtc tccatcttcc gtgtctgcat ctgtaggaga cagagtcacc      60
atcacttgtc gggcgagtca gggtattagc agctggttag cctggtatca gcagaaacca     120
gggaaagccc ctaagctcct gatctatgct gcttccactt tacaaagtgg ggtcccatca     180
aggttcagtg gcagtggatc tgggacagat tcactctca ccatcagcag cctgcagcct    240
gaagattttg caacttacta ttgtcaacgg attaacagtt tcccattcac tttcggccct    300
gggaccaaag tggatatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag    645

<210> SEQ ID NO 97
<211> LENGTH: 214
<212> TYPE: PRT
<213> ORGANISM: Artificial Sequence
<220> FEATURE:
<223> OTHER INFORMATION: synthetic

<400> SEQUENCE: 97

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Arg Ile Asn Ser Phe Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 98
<211> LENGTH: 363
<212> TYPE: DNA
<213> ORGANISM: Artificial Sequence
<220> FEATURE:
<223> OTHER INFORMATION: synthetic

<400> SEQUENCE: 98
gaggtgcagc tggtggagtc tgggggaggc ttggtacagc ctggagggtc cctgagactc    60

```
tcctgtatag cctctggatt caccttcagt gattatgaaa taaattgggt ccgccaggct    120
cccgggaagg ggctggaatg gatctcatat ataagtagta gtggtaaaac cacatattac    180
gcagactctg tgacgggccg attcaccatc tccagagaca acgccaataa accagtgtat    240
ctgcaaatga acagtctgag agtcgaggac acggctgttt attactgtgc gagatggaag    300
tgggactggg acaactacgg tatggacgtc tggggccaag ggaccacggt caccgtctcc    360
tca                                                                 363
```

<210> SEQ ID NO 99
<211> LENGTH: 121
<212> TYPE: PRT
<213> ORGANISM: Artificial Sequence
<220> FEATURE:
<223> OTHER INFORMATION: synthetic

<400> SEQUENCE: 99

```
Glu Val Gln Leu Val Glu Ser Gly Gly Gly Leu Val Gln Pro Gly Gly
1               5                   10                  15

Ser Leu Arg Leu Ser Cys Ile Ala Ser Gly Phe Thr Phe Ser Asp Tyr
            20                  25                  30

Glu Ile Asn Trp Val Arg Gln Ala Pro Gly Lys Gly Leu Glu Trp Ile
        35                  40                  45

Ser Tyr Ile Ser Ser Ser Gly Lys Thr Thr Tyr Tyr Ala Asp Ser Val
    50                  55                  60

Thr Gly Arg Phe Thr Ile Ser Arg Asp Asn Ala Asn Lys Pro Val Tyr
65                  70                  75                  80

Leu Gln Met Asn Ser Leu Arg Val Glu Asp Thr Ala Val Tyr Tyr Cys
                85                  90                  95

Ala Arg Trp Lys Trp Asp Trp Asp Asn Tyr Gly Met Asp Val Trp Gly
            100                 105                 110

Gln Gly Thr Thr Val Thr Val Ser Ser
        115                 120
```

<210> SEQ ID NO 100
<211> LENGTH: 24
<212> TYPE: DNA
<213> ORGANISM: Artificial Sequence
<220> FEATURE:
<223> OTHER INFORMATION: synthetic

<400> SEQUENCE: 100

```
ggattcacct tcagtgatta tgaa                                           24
```

<210> SEQ ID NO 101
<211> LENGTH: 8
<212> TYPE: PRT
<213> ORGANISM: Artificial Sequence
<220> FEATURE:
<223> OTHER INFORMATION: synthetic

<400> SEQUENCE: 101

```
Gly Phe Thr Phe Ser Asp Tyr Glu
1               5
```

<210> SEQ ID NO 102
<211> LENGTH: 24
<212> TYPE: DNA
<213> ORGANISM: Artificial Sequence
<220> FEATURE:
<223> OTHER INFORMATION: synthetic

<400> SEQUENCE: 102
ataagtagta gtggtaaaac caca                                          24

<210> SEQ ID NO 103
<211> LENGTH: 8
<212> TYPE: PRT
<213> ORGANISM: Artificial Sequence
<220> FEATURE:
<223> OTHER INFORMATION: synthetic

<400> SEQUENCE: 103

Ile Ser Ser Ser Gly Lys Thr Thr
1               5

<210> SEQ ID NO 104
<211> LENGTH: 42
<212> TYPE: DNA
<213> ORGANISM: Artificial Sequence
<220> FEATURE:
<223> OTHER INFORMATION: synthetic

<400> SEQUENCE: 104
gcgagatgga agtgggactg ggacaactac ggtatggacg tc                      42

<210> SEQ ID NO 105
<211> LENGTH: 14
<212> TYPE: PRT
<213> ORGANISM: Artificial Sequence
<220> FEATURE:
<223> OTHER INFORMATION: synthetic

<400> SEQUENCE: 105

Ala Arg Trp Lys Trp Asp Trp Asp Asn Tyr Gly Met Asp Val
1               5                   10

<210> SEQ ID NO 106
<211> LENGTH: 321
<212> TYPE: DNA
<213> ORGANISM: Artificial Sequence
<220> FEATURE:
<223> OTHER INFORMATION: synthetic

<400> SEQUENCE: 106
gacatccagt tgacccagtc tccatccttc ctgtctgcat ctgttggaga cagagtcacc    60
atcacttgct gggccagtca ggacaatagc aattatttag cctggtatca gcaaaaacca   120
gggaaagccc ctaacctcct gatctatact gcatccactt tgcagagtgg ggtcccatca   180
cggttcagcg gcagtggatc tgggacagag ttcactctca caatcagcag cctgcagcct   240
gaagattttg caactatta ctgtcaacaa cttaatactt acccattcac tttcggccct   300
gggaccaaag tggatatcaa a                                            321

<210> SEQ ID NO 107
<211> LENGTH: 107
<212> TYPE: PRT
<213> ORGANISM: Artificial Sequence
<220> FEATURE:
<223> OTHER INFORMATION: synthetic

<400> SEQUENCE: 107

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Asp Asn Ser Asn Tyr

```
            20                  25                  30
Leu Ala Trp Tyr Gln Gln Lys Pro Gly Lys Ala Pro Asn Leu Leu Ile
            35                  40                  45

Tyr Thr Ala Ser Thr Leu Gln Ser Gly Val Pro Ser Arg Phe Ser Gly
            50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Thr Tyr Pro Phe
                85                  90                  95

Thr Phe Gly Pro Gly Thr Lys Val Asp Ile Lys
                100                 105
```

<210> SEQ ID NO 108
<211> LENGTH: 18
<212> TYPE: DNA
<213> ORGANISM: Artificial Sequence
<220> FEATURE:
<223> OTHER INFORMATION: synthetic

<400> SEQUENCE: 108
caggacaata gcaattat                                                  18

<210> SEQ ID NO 109
<211> LENGTH: 6
<212> TYPE: PRT
<213> ORGANISM: Artificial Sequence
<220> FEATURE:
<223> OTHER INFORMATION: synthetic

<400> SEQUENCE: 109

```
Gln Asp Asn Ser Asn Tyr
1               5
```

<210> SEQ ID NO 110
<211> LENGTH: 9
<212> TYPE: DNA
<213> ORGANISM: Artificial Sequence
<220> FEATURE:
<223> OTHER INFORMATION: synthetic

<400> SEQUENCE: 110 actgcatcc                                                             9

<210> SEQ ID NO 111
<211> LENGTH: 3
<212> TYPE: PRT
<213> ORGANISM: Artificial Sequence
<220> FEATURE:
<223> OTHER INFORMATION: synthetic

<400> SEQUENCE: 111

```
Thr Ala Ser
1
```

<210> SEQ ID NO 112
<211> LENGTH: 27
<212> TYPE: DNA
<213> ORGANISM: Artificial Sequence
<220> FEATURE:
<223> OTHER INFORMATION: synthetic

<400> SEQUENCE: 112
caacaactta atacttaccc attcact                                         27

<210> SEQ ID NO 113
<211> LENGTH: 9
<212> TYPE: PRT
<213> ORGANISM: Artificial Sequence
<220> FEATURE:
<223> OTHER INFORMATION: synthetic

<400> SEQUENCE: 113

Gln Gln Leu Asn Thr Tyr Pro Phe Thr
1               5

<210> SEQ ID NO 114
<211> LENGTH: 1356
<212> TYPE: DNA
<213> ORGANISM: Artificial Sequence
<220> FEATURE:
<223> OTHER INFORMATION: synthetic

<400> SEQUENCE: 114
gaggtgcagc tggtggagtc tgggggaggc ttggtacagc ctggagggtc cctgagactc      60
tcctgtatag cctctggatt caccttcagt gattatgaaa taaattgggt ccgccaggct     120
cccgggaagg ggctggaatg gatctcatat ataagtagta gtggtaaaac cacatattac     180
gcagactctg tgacgggccg attcaccatc tccagagaca cgccaataa accagtgtat      240 ctgcaaatga acagtctgag agtcgaggac acggctgttt attactgtgc gagatggaag     300
tgggactggg acaactacgg tatggacgtc tggggccaag gaccacggt caccgtctcc      360 tcagcctcaa ctaagggccc aagcgtcttt ccattggctc catccagtaa atcaacttca     420 gggggggaccg cagctctggg gtgcctcgtg aaggactact ccctgaacc tgtcacagtc     480 tcctggaact ccggggctct gaccagcgga gttcacacct ttcctgccgt gcttcagtct     540
tccgggctgt actcattgag cagtgtcgtt actgtaccat cctcctccct gggtactcaa     600
acctacatct gtaatgtgaa ccacaagccc tccaacacca aggttgacaa aaaggtggaa     660
ccaaagagtt gtgataagac tcatacctgc cccccatgtc ctgcccccga gctgctggga     720
ggaccttcag tgttcttgtt ccctcccaaa ccaaaagaca cttttgatgat ttcacgaacc     780 cctgaagtga cctgtgtggt ggtcgatgtc agccacgaag accctgaagt taagtttaac     840
tggtatgtgg atggcgtaga ggttcacaac gctaagacta acccagaga ggagcaatat      900 aatagtacct atagggtcgt gtctgtgctg acagtcttgc atcaggactg gcttaacggt     960
aaggagtaca gtgtaaggt gtcaaacaag gcactgcctg cacctatcga gaagaccatc     1020
tctaaggcca aaggtcaacc aagggagccc caggtatata ctttgccacc ctctcgggac     1080
gagctgacaa aaaatcaggt gagtctgacc tgtctcgtga aggattttta ccctagcgac     1140
atcgccgtgg agtgggagag taatggccag cccgagaata actacaagac cacccccacca    1200 gttctggact ctgacgggtc tttcttcctt tatagtaagc tgaccgtaga taagtctcgc     1260
tggcagcaag gcaatgtatt ctcttgcagt gtcatgcacg aggccctcca taaccgattc     1320
acccaaaaat ctctgtctct gtctcctgga aagtga                              1356

<210> SEQ ID NO 115
<211> LENGTH: 451
<212> TYPE: PRT
<213> ORGANISM: Artificial Sequence
<220> FEATURE:
<223> OTHER INFORMATION: synthetic

<400> SEQUENCE: 115

-continued

```
Glu Val Gln Leu Val Glu Ser Gly Gly Gly Leu Val Gln Pro Gly Gly
1               5                   10                  15

Ser Leu Arg Leu Ser Cys Ile Ala Ser Gly Phe Thr Phe Ser Asp Tyr
            20                  25                  30

Glu Ile Asn Trp Val Arg Gln Ala Pro Gly Lys Gly Leu Glu Trp Ile
            35                  40                  45

Ser Tyr Ile Ser Ser Ser Gly Lys Thr Thr Tyr Tyr Ala Asp Ser Val
50                  55                  60

Thr Gly Arg Phe Thr Ile Ser Arg Asp Asn Ala Asn Lys Pro Val Tyr
65                  70                  75                  80

Leu Gln Met Asn Ser Leu Arg Val Glu Asp Thr Ala Val Tyr Tyr Cys
                85                  90                  95

Ala Arg Trp Lys Trp Asp Trp Asp Asn Tyr Gly Met Asp Val Trp Gly
            100                 105                 110

Gln Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
```

His Glu Ala Leu His Asn Arg Phe Thr Gln Lys Ser Leu Ser Leu Ser
            435                 440                 445
Pro Gly Lys
    450

<210> SEQ ID NO 116
<211> LENGTH: 645
<212> TYPE: DNA
<213> ORGANISM: Artificial Sequence
<220> FEATURE:
<223> OTHER INFORMATION: synthetic

<400> SEQUENCE: 116

```
gacatccagt tgacccagtc tccatccttc ctgtctgcat ctgttggaga cagagtcacc      60
atcacttgct gggccagtca ggacaatagc aattatttag cctggtatca gcaaaaacca     120
gggaaagccc ctaacctcct gatctatact gcatccactt tgcagagtgg ggtcccatca     180
cggttcagcg gcagtggatc tgggacagag ttcactctca caatcagcag cctgcagcct     240
gaagattttg caacttatta ctgtcaacaa cttaatactt acccattcac tttcggccct     300
gggaccaaag tggatatcaa acgaactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gttag                    645
```

<210> SEQ ID NO 117
<211> LENGTH: 214
<212> TYPE: PRT
<213> ORGANISM: Artificial Sequence
<220> FEATURE:
<223> OTHER INFORMATION: synthetic

<400> SEQUENCE: 117

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Asp Asn Ser Asn Tyr
            20                  25                  30

Leu Ala Trp Tyr Gln Gln Lys Pro Gly Lys Ala Pro Asn Leu Leu Ile
        35                  40                  45

Tyr Thr Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Thr Tyr Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 118
<211> LENGTH: 354
<212> TYPE: DNA
<213> ORGANISM: Artificial Sequence
<220> FEATURE:
<223> OTHER INFORMATION: synthetic

<400> SEQUENCE: 118

```
gaagtgcagc tggtggagtc tgggggaggc gtaatacagc ctgggggtc cctgagactc      60
tcctgtgcag cctctggatt caccttgat tattatgcca tgcactgggt ccgtcaagct     120
ccagggaagg gtctggagtg gtctctctt attagtgggg atggtggtag cacatattat     180
gcagactctg tgaagggccg attcaccatc tccagagaca cagcaaaag ctccctgtat     240
ctgcaaatga acagtctgag aattgaggac accgccttgt attattgtat aaagggggtt     300
cggggatacg gtatggacgt ctggggccaa gggaccacgg tcaccgtctc ctca           354
```

<210> SEQ ID NO 119
<211> LENGTH: 118
<212> TYPE: PRT
<213> ORGANISM: Artificial Sequence
<220> FEATURE:
<223> OTHER INFORMATION: synthetic

<400> SEQUENCE: 119

Glu Val Gln Leu Val Glu Ser Gly Gly Gly Val Ile Gln Pro Gly Gly
1               5                   10                  15

Ser Leu Arg Leu Ser Cys Ala Ala Ser Gly Phe Thr Leu Asp Tyr Tyr
            20                  25                  30

Ala Met His Trp Val Arg Gln Ala Pro Gly Lys Gly Leu Glu Trp Val
        35                  40                  45

Ser Leu Ile Ser Gly Asp Gly Gly Ser Thr Tyr Tyr Ala Asp Ser Val
    50                  55                  60

Lys Gly Arg Phe Thr Ile Ser Arg Asp Asn Ser Lys Ser Ser Leu Tyr
65                  70                  75                  80

Leu Gln Met Asn Ser Leu Arg Ile Glu Asp Thr Ala Leu Tyr Tyr Cys
            85                  90                  95

Ile Lys Gly Val Arg Gly Tyr Gly Met Asp Val Trp Gly Gln Gly Thr
            100                 105                 110

Thr Val Thr Val Ser Ser
        115

<210> SEQ ID NO 120
<211> LENGTH: 24
<212> TYPE: DNA
<213> ORGANISM: Artificial Sequence
<220> FEATURE:
<223> OTHER INFORMATION: synthetic

<400> SEQUENCE: 120
ggattcaccc ttgattatta tgcc                                              24

<210> SEQ ID NO 121
<211> LENGTH: 8
<212> TYPE: PRT
<213> ORGANISM: Artificial Sequence
<220> FEATURE:
<223> OTHER INFORMATION: synthetic

<400> SEQUENCE: 121

Gly Phe Thr Leu Asp Tyr Tyr Ala
1               5

<210> SEQ ID NO 122
<211> LENGTH: 24
<212> TYPE: DNA
<213> ORGANISM: Artificial Sequence
<220> FEATURE:
<223> OTHER INFORMATION: synthetic

<400> SEQUENCE: 122
attagtgggg atggtggtag caca                                              24

<210> SEQ ID NO 123
<211> LENGTH: 8
<212> TYPE: PRT
<213> ORGANISM: Artificial Sequence
<220> FEATURE:
<223> OTHER INFORMATION: synthetic

<400> SEQUENCE: 123

Ile Ser Gly Asp Gly Gly Ser Thr
1               5

<210> SEQ ID NO 124
<211> LENGTH: 33
<212> TYPE: DNA
<213> ORGANISM: Artificial Sequence
<220> FEATURE:
<223> OTHER INFORMATION: synthetic

<400> SEQUENCE: 124
ataaaggggg ttcgggata cggtatggac gtc                                     33

<210> SEQ ID NO 125
<211> LENGTH: 11
<212> TYPE: PRT
<213> ORGANISM: Artificial Sequence
<220> FEATURE:
<223> OTHER INFORMATION: synthetic

<400> SEQUENCE: 125

Ile Lys Gly Val Arg Gly Tyr Gly Met Asp Val
1               5                   10

<210> SEQ ID NO 126
<211> LENGTH: 321
<212> TYPE: DNA
<213> ORGANISM: Artificial Sequence
<220> FEATURE:
<223> OTHER INFORMATION: synthetic

<400> SEQUENCE: 126
gacatccaga tgacccagtc tccatcctcc ctgtctgcat ctgtaggaga cagaatcacc        60
atcacttgcc aggcgagtca ggacattagt aatcgtttaa attggtatca gcagaaaaca       120

```
gggagagccc ctaagctcct gatctacgat gcatccaatt tggaaacagg ggtcccatca    180
aggttcagtg gcagtggatc tgggacagat tttactttca ccatcagcaa cctgcagcct    240
gaagatatta caacatatta ctgtcaacat tataataata tcccgtacac ttttggccag    300
gggaccaagc tggagatcaa a                                              321
```

```
<210> SEQ ID NO 127
<211> LENGTH: 107
<212> TYPE: PRT
<213> ORGANISM: Artificial Sequence
<220> FEATURE:
<223> OTHER INFORMATION: synthetic

<400> SEQUENCE: 127
```

Asp Ile Gln Met Thr Gln Ser Pro Ser Leu Ser Ala Ser Val Gly
1               5                   10                  15

Asp Arg Ile Thr Ile Thr Cys Gln Ala Ser Gln Asp Ile Ser Asn Arg
            20                  25                  30

Leu Asn Trp Tyr Gln Gln Lys Thr Gly Arg Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Asn Leu Gln Pro
65                  70                  75                  80

Glu Asp Ile Thr Thr Tyr Tyr Cys Gln His Tyr Asn Asn Ile Pro Tyr
                85                  90                  95

Thr Phe Gly Gln Gly Thr Lys Leu Glu Ile Lys
            100                 105

```
<210> SEQ ID NO 128
<211> LENGTH: 18
<212> TYPE: DNA
<213> ORGANISM: Artificial Sequence
<220> FEATURE:
<223> OTHER INFORMATION: synthetic

<400> SEQUENCE: 128
caggacatta gtaatcgt                                                   18

<210> SEQ ID NO 129
<211> LENGTH: 6
<212> TYPE: PRT
<213> ORGANISM: Artificial Sequence
<220> FEATURE:
<223> OTHER INFORMATION: synthetic

<400> SEQUENCE: 129
```

Gln Asp Ile Ser Asn Arg
1               5

```
<210> SEQ ID NO 130
<211> LENGTH: 9
<212> TYPE: DNA
<213> ORGANISM: Artificial Sequence
<220> FEATURE:
<223> OTHER INFORMATION: synthetic

<400> SEQUENCE: 130 gatgcatcc                                                              9

<210> SEQ ID NO 131
<211> LENGTH: 3
```

```
<212> TYPE: PRT
<213> ORGANISM: Artificial Sequence
<220> FEATURE:
<223> OTHER INFORMATION: synthetic

<400> SEQUENCE: 131

Asp Ala Ser
1

<210> SEQ ID NO 132
<211> LENGTH: 27
<212> TYPE: DNA
<213> ORGANISM: Artificial Sequence
<220> FEATURE:
<223> OTHER INFORMATION: synthetic

<400> SEQUENCE: 132
caacattata ataatatccc gtacact                                          27

<210> SEQ ID NO 133
<211> LENGTH: 9
<212> TYPE: PRT
<213> ORGANISM: Artificial Sequence
<220> FEATURE:
<223> OTHER INFORMATION: synthetic

<400> SEQUENCE: 133

Gln His Tyr Asn Asn Ile Pro Tyr Thr
1               5

<210> SEQ ID NO 134
<211> LENGTH: 1347
<212> TYPE: DNA
<213> ORGANISM: Artificial Sequence
<220> FEATURE:
<223> OTHER INFORMATION: synthetic

<400> SEQUENCE: 134
gaagtgcagc tggtggagtc tgggggaggc gtaatacagc ctggggggtc cctgagactc      60
tcctgtgcag cctctggatt cacccttgat tattatgcca tgcactgggt ccgtcaagct     120
ccagggaagg gtctggagtg gtctctctct attagtgggg atggtggtag cacatattat     180
gcagactctg tgaagggccg attcaccatc tccagagaca acagcaaaag ctccctgtat     240
ctgcaaatga acagtctgag aattgaggac accgccttgt attattgtat aaaggggtt      300 cggggatacg gtatggacgt ctggggccaa gggaccacgg tcaccgtctc ctcagcctca     360
actaagggcc caagcgtctt tccattggct ccatccagta atcaacttc aggggggacc     420 gcagctctgg ggtgcctcgt gaaggactac ttccctgaac ctgtcacagt ctcctggaac     480 tccgggctc tgaccagcgg agttcacacc tttcctgccg tgcttcagtc ttccgggctg     540
tactcattga gcagtgtcgt tactgtacca tcctcctccc tgggtactca aacctacatc     600
tgtaatgtga accacaagcc ctccaacacc aaggttgaca aaaaggtgga ccaaagagt      660 tgtgataaga ctcatacctg ccccccatgt cctgcccccg agctgctggg aggaccttca     720
gtgttcttgt tccctcccaa accaaaagac actttgatga tttcacgaac ccctgaagtg     780
acctgtgtgg tggtcgatgt cagccacgaa gaccctgaag ttaagtttaa ctggtatgtg     840
gatggcgtag aggttcacaa cgctaagact aaacccagag aggagcaata taatagtacc     900
tatagggtcg tgtctgtgct gacagtcttg catcaggact ggcttaacgg taaggagtac     960
aagtgtaagg tgtcaaacaa ggcactgcct gcacctatcg agaagaccat ctctaaggcc    1020
```

```
aaaggtcaac caagggagcc ccaggtatat actttgccac cctctcggga cgagctgaca   1080
aaaaatcagg tgagtctgac ctgtctcgtg aaaggatttt accctagcga catcgccgtg   1140
gagtgggaga gtaatggcca gcccgagaat aactacaaga ccaccccacc agttctggac   1200
tctgacgggt cttttcttcct ttatagtaag ctgaccgtag ataagtctcg ctggcagcaa   1260
ggcaatgtat tctcttgcag tgtcatgcac gaggccctcc ataaccgatt cacccaaaaa   1320
tctctgtctc tgtctcctgg aaagtga                                       1347
```

<210> SEQ ID NO 135
<211> LENGTH: 448
<212> TYPE: PRT
<213> ORGANISM: Artificial Sequence
<220> FEATURE:
<223> OTHER INFORMATION: synthetic
<400> SEQUENCE: 135

```
Glu Val Gln Leu Val Glu Ser Gly Gly Gly Val Ile Gln Pro Gly Gly
1               5                   10                  15

Ser Leu Arg Leu Ser Cys Ala Ala Ser Gly Phe Thr Leu Asp Tyr Tyr
            20                  25                  30

Ala Met His Trp Val Arg Gln Ala Pro Gly Lys Gly Leu Glu Trp Val
        35                  40                  45

Ser Leu Ile Ser Gly Asp Gly Gly Ser Thr Tyr Tyr Ala Asp Ser Val
    50                  55                  60

Lys Gly Arg Phe Thr Ile Ser Arg Asp Asn Ser Lys Ser Ser Leu Tyr
65                  70                  75                  80

Leu Gln Met Asn Ser Leu Arg Ile Glu Asp Thr Ala Leu Tyr Tyr Cys
                85                  90                  95

Ile Lys Gly Val Arg Gly Tyr Gly Met Asp Val Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300
```

```
Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn Arg Phe Thr Gln Lys Ser Leu Ser Leu Ser Pro Gly Lys
        435                 440                 445

<210> SEQ ID NO 136
<211> LENGTH: 645
<212> TYPE: DNA
<213> ORGANISM: Artificial Sequence
<220> FEATURE:
<223> OTHER INFORMATION: synthetic

<400> SEQUENCE: 136
gacatccaga tgacccagtc tccatcctcc ctgtctgcat ctgtaggaga cagaatcacc     60
atcacttgcc aggcgagtca ggacattagt aatcgtttaa attggtatca gcagaaaaca    120
gggagagccc ctaagctcct gatctacgat gcatccaatt tggaaacagg ggtcccatca    180
aggttcagtg gcagtggatc tgggacagat tttactttca ccatcagcaa cctgcagcct    240
gaagatatta acatatta ctgtcaacat tataataata tcccgtacac ttttggccag    300
gggaccaagc tggagatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                    645

<210> SEQ ID NO 137
<211> LENGTH: 214
<212> TYPE: PRT
<213> ORGANISM: Artificial Sequence
<220> FEATURE:
<223> OTHER INFORMATION: synthetic

<400> SEQUENCE: 137

Asp Ile Gln Met Thr Gln Ser Pro Ser Ser Leu Ser Ala Ser Val Gly
1               5                   10                  15

Asp Arg Ile Thr Ile Thr Cys Gln Ala Ser Gln Asp Ile Ser Asn Arg
            20                  25                  30

Leu Asn Trp Tyr Gln Gln Lys Thr Gly Arg Ala Pro Lys Leu Leu Ile
        35                  40                  45

Tyr Asp Ala Ser Asn Leu Glu Thr Gly Val Pro Ser Arg Phe Ser Gly
```

```
                    50                  55                  60
Ser Gly Ser Gly Thr Asp Phe Thr Phe Thr Ile Ser Asn Leu Gln Pro
 65                  70                  75                  80

Glu Asp Ile Thr Thr Tyr Tyr Cys Gln His Tyr Asn Asn Ile Pro Tyr
                 85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
210
```